(12) United States Patent
Hayes et al.

(10) Patent No.: US 12,053,498 B2
(45) Date of Patent: *Aug. 6, 2024

(54) FRUIT AND VEGETABLE POMACE COMPOSITION AND USE AS BLOOD GLUCOSE MODULATOR AND ANTI-DIABETIC AGENT

(71) Applicant: BRANDEIS UNIVERSITY, Waltham, MA (US)

(72) Inventors: Kenneth C. Hayes, Wellesley Hills, MA (US); Daniel Perlman, Arlington, MA (US)

(73) Assignee: Brandeis University, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/899,752

(22) Filed: Aug. 31, 2022

(65) Prior Publication Data

US 2023/0033446 A1 Feb. 2, 2023

Related U.S. Application Data

(60) Continuation of application No. 16/783,962, filed on Feb. 6, 2020, now Pat. No. 11,464,820, which is a division of application No. 15/770,298, filed as application No. PCT/US2016/058904 on Oct. 26, 2016, now Pat. No. 10,596,213.

(60) Provisional application No. 62/345,332, filed on Jun. 3, 2016, provisional application No. 62/246,419, filed on Oct. 26, 2015.

(51) Int. Cl.
*A61K 36/23* (2006.01)
*A23L 33/22* (2016.01)
*A61P 3/00* (2006.01)
*A61P 3/10* (2006.01)

(52) U.S. Cl.
CPC .............. *A61K 36/23* (2013.01); *A23L 33/22* (2016.08); *A61P 3/00* (2018.01); *A61P 3/10* (2018.01); *A61K 2236/00* (2013.01)

(58) Field of Classification Search
CPC ...................................................... A61K 36/23
See application file for complete search history.

(56) References Cited

PUBLICATIONS

Sharma et al., Chemical composition, functional properties and processing of carrot—a review, J Food Sci Technol 49(1):22-32, 2012.*

Houben et al., "Thermal and high-pressure stability of pectin-converting enzymes in broccoli and carrot puree: towards the creation of specific endogenous enzyme populations through processing," Food Bioprocess Technol 7:1713-1724, 2014.*

* cited by examiner

*Primary Examiner* — Rosanne Kosson
(74) *Attorney, Agent, or Firm* — Troutman Pepper Hamilton Sanders LLP

(57) ABSTRACT

Methods of improving mammalian carbohydrate metabolism and treating, preventing, or halting the progression of type 2 diabetes mellitus involve the consumption of a nutritional composition containing fruit or vegetable pomace. The pomace is produced from native plant tissue and contains a mixture of soluble and insoluble fiber. Periodic consumption of the composition normalizes blood glucose concentration and controls body weight.

29 Claims, 11 Drawing Sheets

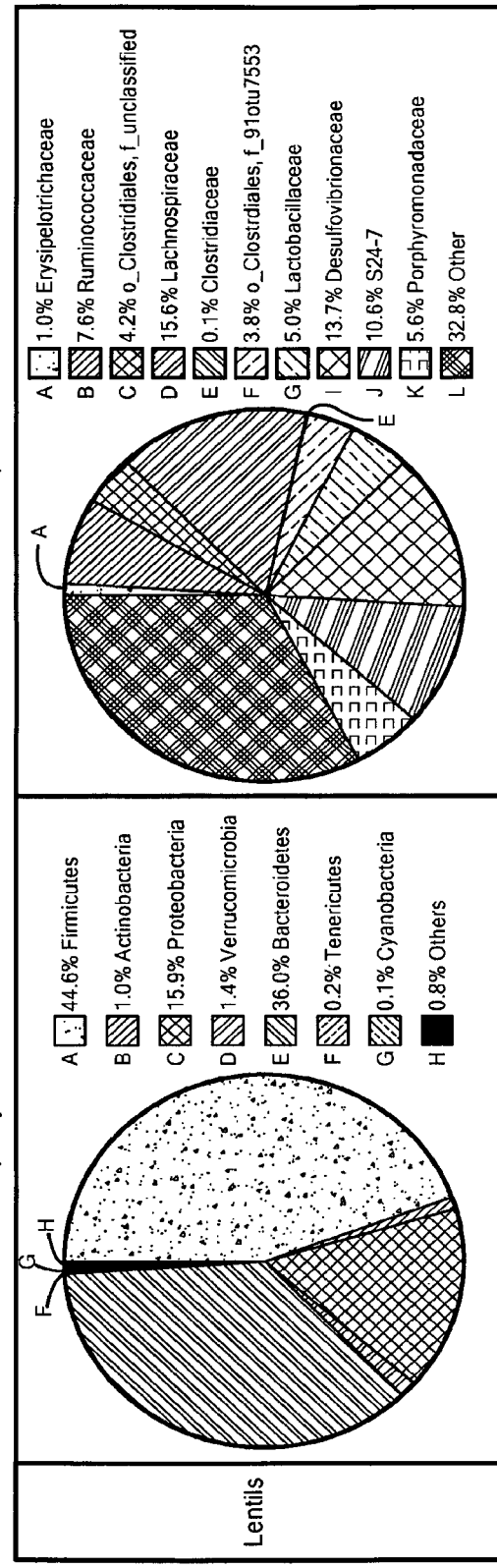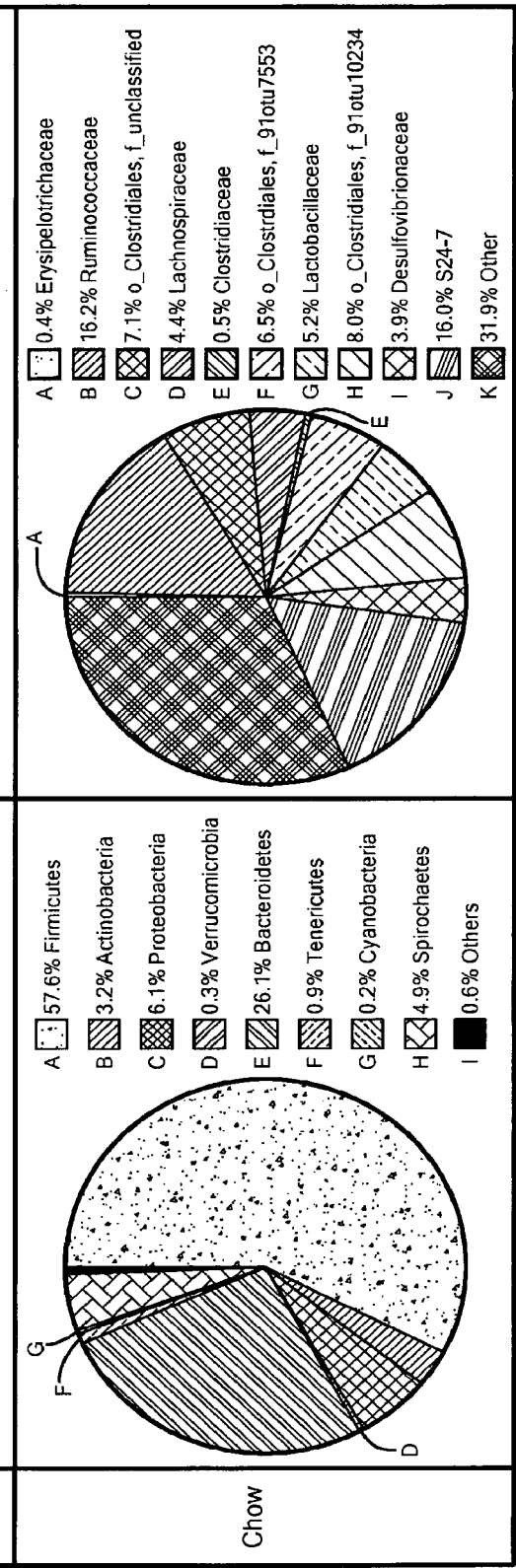
FIG. 3A  Lentils  Top Phyla
FIG. 3B  Top 10 Families
FIG. 4A  Chow
FIG. 4B

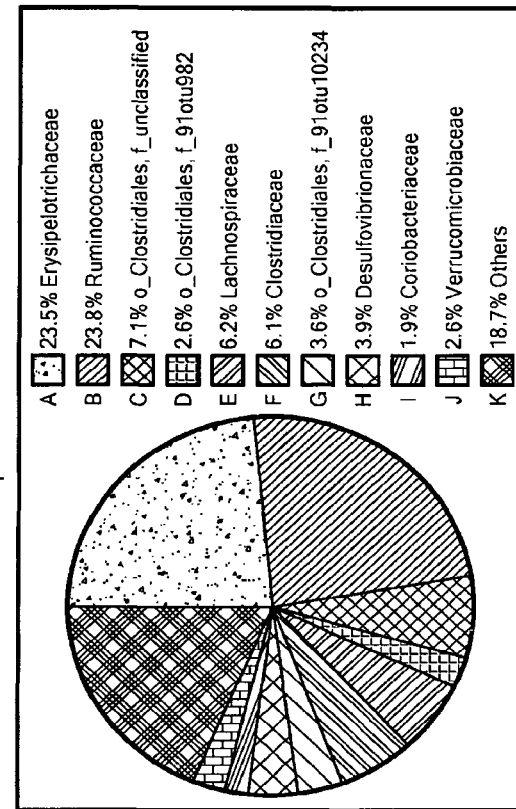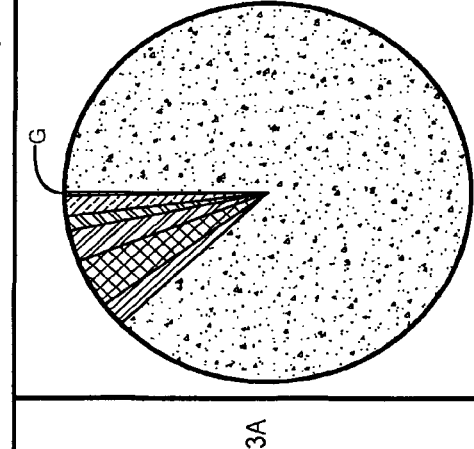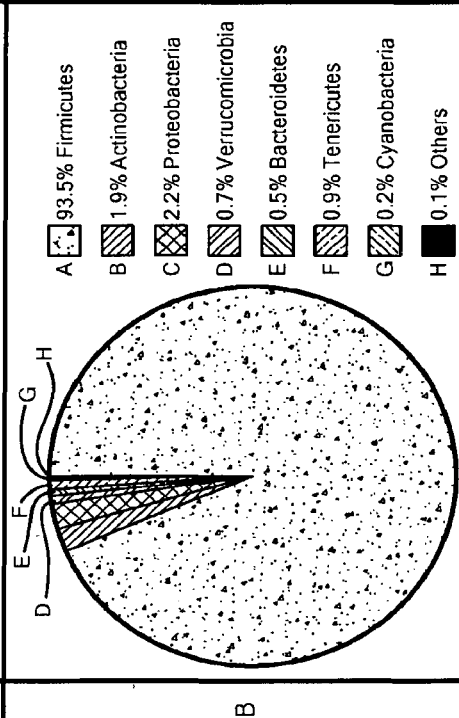
FIG. 5A  FIG. 5B  FIG. 6A  FIG. 6B

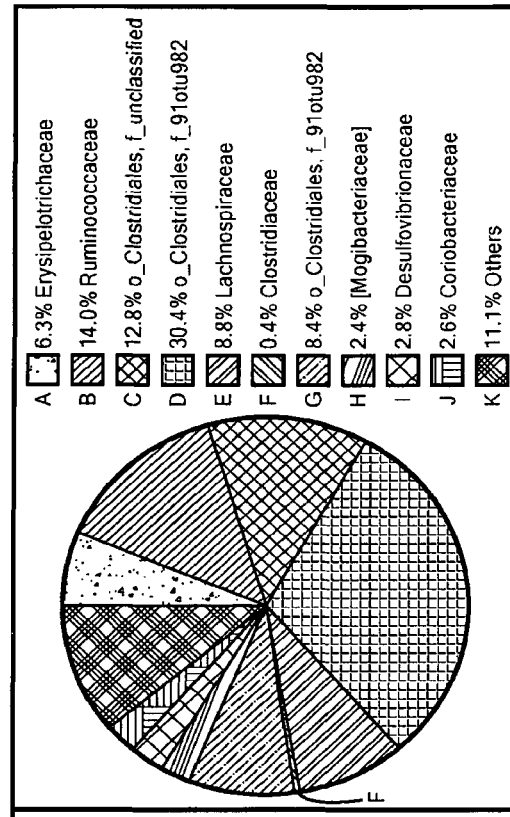
FIG. 7A  Top Phyla
FIG. 7B  Top 10 Families
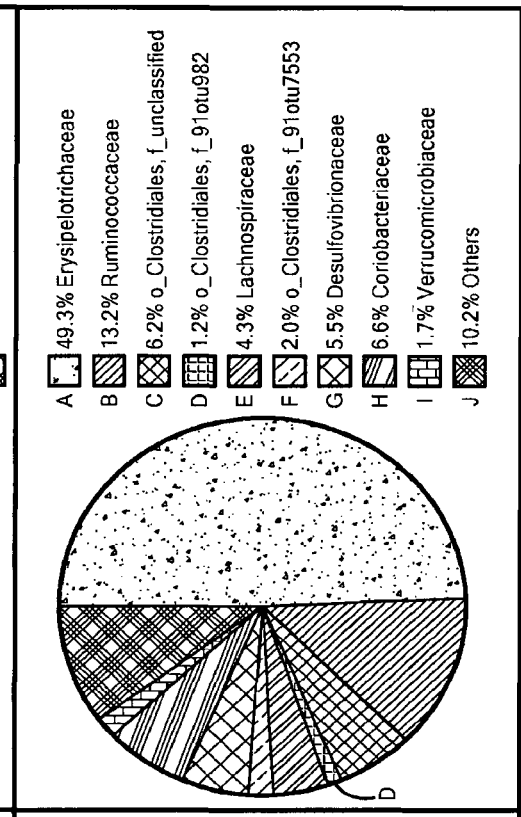
FIG. 8A
FIG. 8B

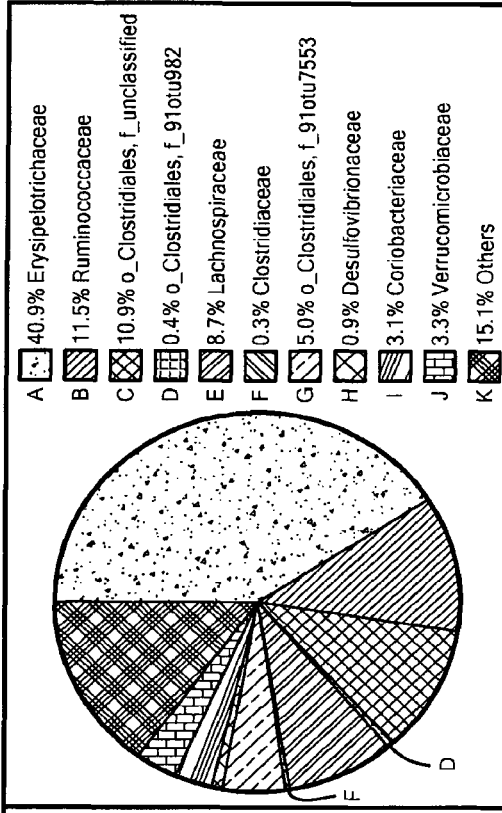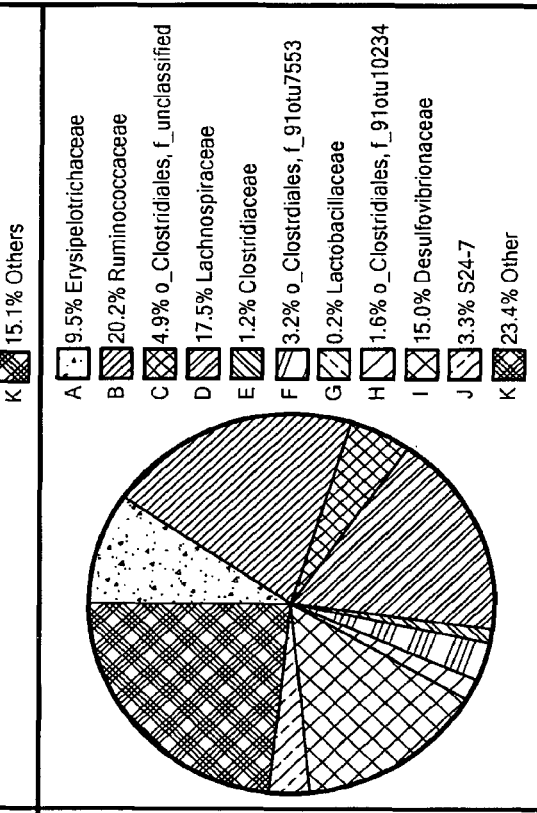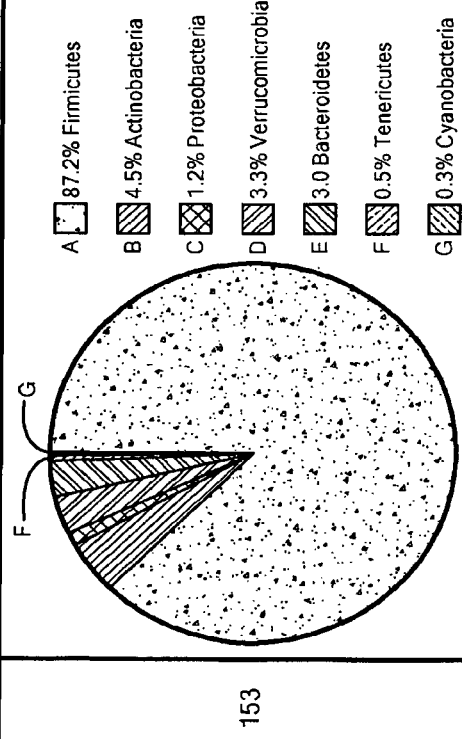
FIG. 9A  FIG. 9B  FIG. 10A  FIG. 10B

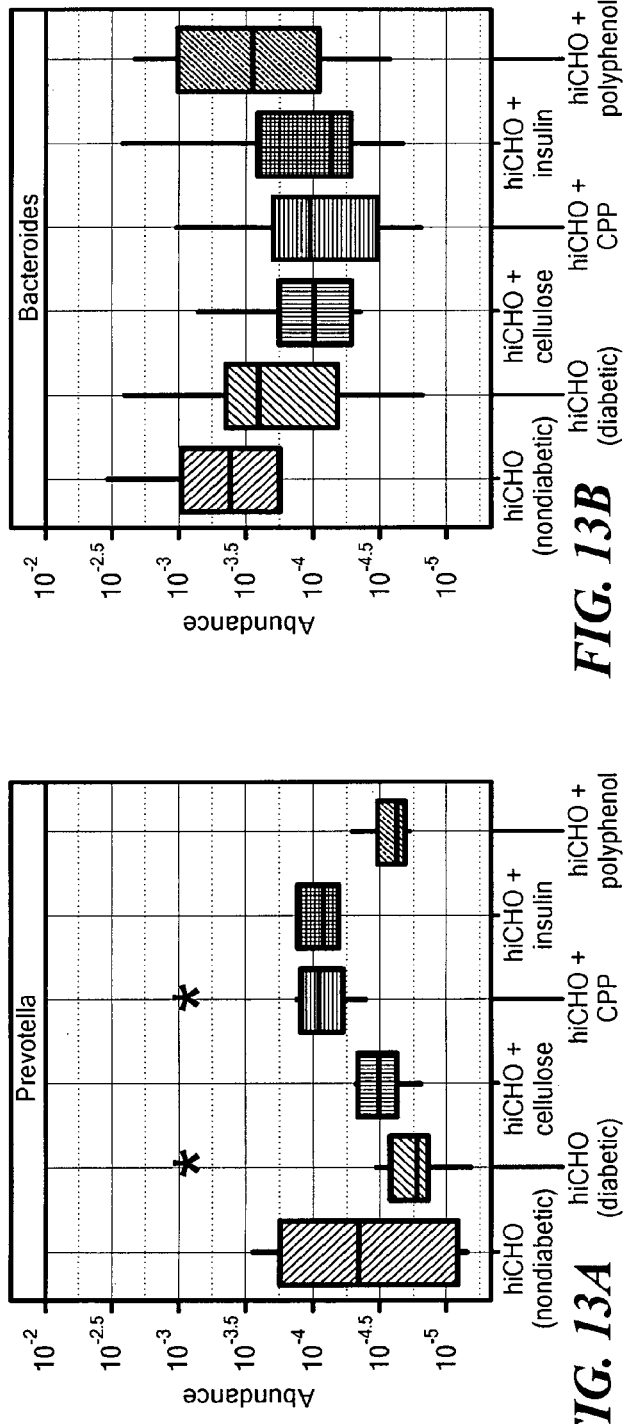
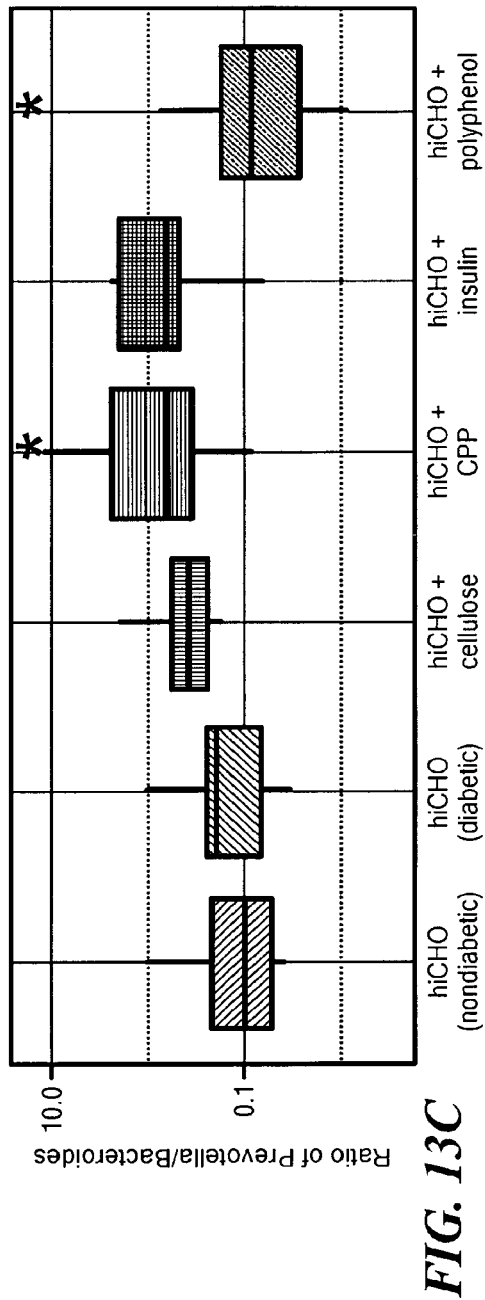
FIG. 13A
FIG. 13B
FIG. 13C

FRUIT AND VEGETABLE POMACE COMPOSITION AND USE AS BLOOD GLUCOSE MODULATOR AND ANTI-DIABETIC AGENT

CROSS REFERENCE TO RELATED APPLICATIONS

The present application is a continuation application under 35 U.S.C. § 121 of U.S. patent application Ser. No. 16/783,962, filed Feb. 6, 2020, which is a divisional application under 35 U.S.C. § 121 of U.S. patent application Ser. No. 15/770,298, filed Apr. 23, 2018, now issued as U.S. Pat. No. 10,596,213 on Mar. 24, 2020, which is a national stage application under 35 U.S.C. § 371 of PCT Application No. PCT/US2016/058904, filed Oct. 26, 2016, which claims the priority of U.S. Provisional Application No. 62/246,419, filed Oct. 26, 2015, and U.S. Provisional Application No. 62/345,332, filed Jun. 3, 2015, all of which are hereby incorporated by reference in their entirety.

BACKGROUND

The increasing worldwide prevalence of carbohydrate-related metabolic diseases including diabetes, obesity, metabolic syndrome, and their related long-term consequences, continues to pose a challenge to health care systems (1). Poor and unbalanced diet is considered a major environmental insult contributing to the increase in metabolic disease incidence, especially in younger individuals.

Animal models exist that mimic most features of human diabetes. Such models are useful for better understanding the connection between diet and disease, and for developing dietary guidelines and improving management of the disease (2). The male Nile rat is an effective model for the study of type-2 diabetes mellitus and metabolic syndrome due to the animal's natural genetic susceptibility to these diseases and to alteration of the progression and outcome of these diseases by diet. The pathogenesis, as well as the animal's response to nutritional manipulation, conforms to the human disease (3-6). Studies with the Nile rat have demonstrated that neutralizing the glycemic load of a standard high carbohydrate diet by adding acarbose (a drug used to treat type-2 diabetes) or enhancing insulin sensitivity by supplementing metformin (another drug for type-2 diabetes) exerted significant antidiabetic effects, demonstrating the similarities between NR and human metabolism (K. C. Hayes, unpublished results, 2014). Even as new classes of oral anti-diabetic drugs are being developed and designed (7), establishing a diet-based approach to delay or completely prevent the need for such anti-diabetic medication would be a useful adjunct for individuals suffering from type-2 diabetes mellitus or impaired glucose tolerance.

Reducing the glycemic index and/or glycemic load may reduce the risk for type-2 diabetes in humans (8-10). A recent meta-analysis of 14 studies suggests that glycemic index and glycemic load of foods are meaningful predictors of type-2 diabetes risk in younger subjects if the diet glycemic load data are updated periodically (10). This concept reportedly works as well for cardiovascular risk (11). Dietary fiber has generally proven beneficial in clinical trials focused on fruit and legume intake that improved blood glucose levels and other metabolic parameters (12-16).

Biyani et al. in U.S. Pat. No. 6,361,818 describe a low fat, high fiber carrot product containing 20-50% by weight dietary fiber in which insoluble fiber substantially exceeds soluble fiber. The product is made by combining carrot juice from crushed carrots with a variety of ingredients, concentrating the mixture, adding the concentrate to a carrot pomace, and drying the mixture under vacuum. The resulting high fiber granules are also high in sugars from the added juice. Ingestion of the granules increases satiety, decreases food consumption, and promotes weight loss.

Didden in U.S. Patent Appl. No. 2014/0127297 describes a nutraceutical composition for limiting the absorption of dietary lipids for inducing weight loss. The composition contains a high fiber carrot extract combined with insoluble fiber from apple and/or oat. The resulting compositions when orally administrated decrease absorption of dietary lipids and promote weight loss in mammals including humans.

There remains a need for nutritional compositions and methods for treating and/or preventing type-2 diabetes and its progression.

SUMMARY OF THE INVENTION

The invention provides compositions and methods for dietary modulation useful in the prevention and management of metabolic syndrome, type 2 diabetes mellitus (T2DM), and other diseases related to carbohydrate metabolism. The compositions include a dietary fiber product such as that generally known as carrot pomace (one form of which is carrot pomace powder, or CPP), which is the solid residue remaining after the commercial juicing of carrots. The methods include administering fruit or vegetable pomace, such as carrot pomace, or a food or beverage composition containing fruit or vegetable pomace to a subject, whereby the dietary fiber mixture beneficially alters carbohydrate uptake in the gastrointestinal (GI) system of the subject (and may also beneficially alter the microflora and their metabolic products released in the large intestine) and prevents, controls, or treats diseases or conditions related to carbohydrate digestion and absorption and its subsequent metabolism.

Fruit or vegetable pomace for use in the present invention is a composition that contains a mixture of soluble fiber and insoluble fiber obtained from the edible portion of fruits or vegetables, preferably in a weight ratio of soluble fiber to insoluble fiber of about 0.6 to about 1.4. While pomace such as carrot pomace is often a by-product or residue from juicing, pomace for use in the invention need not be obtained from a commercial juicing operation, but can be obtained by other methods. The insoluble fiber is selected from the group consisting of cellulose, hemicellulose, lignin, and combinations thereof, and the soluble fiber includes pectin. In preferred embodiments, the fruit or vegetable pomace is produced by a method including heat treatment, juice extraction, drying, and grinding of the residue. In preferred embodiments, the heat treatment is sufficient to raise the fruit or vegetable tissue to a temperature in the range from about 100° F. to about 200° F. In preferred embodiments, the pomace is produced by a method including the release and removal of at least 40% of the weight as juice, and the juice contains at least 3.5 wt % sugar. In certain embodiments, the pomace is produced by a method that does not include alkaline treatment, bleach treatment, extraction with hot water, or heat treatment to an extent that would denature the dietary fiber, such as heat treatment that would degrade or destroy quaternary structure of associated fiber complexes, such as soluble-insoluble fiber complexes. Excessive grinding of the pomace is also to be avoided, so as to avoid denaturation of naturally occurring soluble fiber-insoluble fiber complexes, e.g., pectin-cellulose type complexes. A pomace particle size of 60 mesh or less is preferred.

One aspect of the invention is a method of maintaining or achieving normal blood glucose concentration in response to a diabetogenic diet in a mammalian subject. The method includes periodically administering to a mammalian subject, that is consuming a diabetogenic diet, a nutritional composition comprising fruit or vegetable pomace. As a result, the subject's blood glucose concentration is maintained within a normal range or achieves a value within a normal range.

Another aspect of the invention is a method to aid in treating or preventing a disease or condition related to carbohydrate metabolism. The method includes periodically administering to a subject in need thereof a nutritional composition comprising fruit or vegetable pomace. As a result, at least one symptom of the disease or condition is reduced, or the onset or progression of the disease or condition is delayed or prevented. In embodiments of the method, the disease or condition is type 1 diabetes mellitus (also referred to herein as type 1 diabetes), type 2 diabetes mellitus (also referred to herein as type 2 diabetes), gestational diabetes mellitus, prediabetes, metabolic syndrome, or obesity.

Yet another aspect of the invention is a nutritional composition comprising fruit or vegetable pomace for use in maintaining or achieving normal blood glucose concentration in response to a diabetogenic diet in a mammalian subject.

Still another aspect of the invention is a nutritional composition comprising fruit or vegetable pomace for use in treating or preventing a disease or condition related to carbohydrate metabolism in a subject.

Even another aspect is the use of fruit or vegetable pomace to reduce weight gain, especially fat accumulation, without significantly altering normal food intake and without deterring linear growth or body weight (muscle and bone structure).

Another aspect of the invention is a nutritional composition prepared by supplementation of a food, beverage, or dietary composition with fruit or vegetable pomace. In preferred embodiments, the pomace is unbleached, pectinase-free, and sugar-reduced, i.e., containing a reduced fraction of sugars, or containing a reduced dry weight ratio of sugars to dietary fiber, compared to native plant tissue. In preferred embodiments, the pomace is in the form of small particles that do not leave a gritty mouth feel after incorporation into foods or beverages, and that form a stable aqueous suspension. When the composition is administered periodically to a mammalian subject in need thereof, the subject maintains or achieves normal blood glucose concentration. In embodiments the nutritional composition contains about 2-5 wt %, about 3-5 wt %, about 4-7 wt %, about 5-8 wt %, about 5-10 wt %, about 8-12 wt %, about 10-15 wt %, about 10-20 wt %, or at least about 3, 5, 7, 10, 12, 15, or 20 wt %, on a dry weight basis, of the pomace. In certain embodiments, the nutritional corn position is formulated as a dietary formulation containing an amount of pomace sufficient to provide at least 20% of the required daily intake of dietary fiber for the subject.

Yet another aspect of the invention is a method of maintaining or improving a health-promoting intestinal microbiome in response to a diabetogenic diet in a mammalian subject. The method includes periodically administering to the mammalian subject, who is consuming a diabetogenic diet, a nutritional composition containing a fruit or vegetable pomace, such as carrot pomace, whereby the subject's intestinal microbiome is adapted to the presence of a fiber component of said carrot pomace composition, such as by fermentation of the fiber component. In embodiments of the method, administering the carrot pomace composition alters the intestinal microbiome compared to an intestinal microbiome of the subject without administering the carrot pomace composition. In embodiments of the method, bacteria of the *Prevotella* genus increase as a percentage of the microbiome and the *Bacteroides* genus decreases. Ideally the *Prevotella/Bacteroides* ratio increases. Without intending to limit the invention to any particular mechanism, it is believed that the beneficial health effects of the method can result at least in part from increased fermentation of plant fiber and protein to enhance short chain fatty acid production, which in turn exert beneficial effects on gut mucosal metabolism, liver glucose and lipid metabolism, enhanced bile acid turnover and appetite control via the central nervous system. In addition, deposition of adipose tissue is decreased and body weight better regulated.

The present invention utilizes fruit or vegetable pomace as a source of dietary fiber for modulating blood glucose. "Dietary fiber" as used herein refers to the indigestible portion of food materials derived from plants. Dietary fiber is the sum of soluble fiber and insoluble fiber.

The term "fruit or vegetable pomace" as used herein refers to the solid or semi-solid residue from a juice extraction process of an edible fruit or vegetable material. Suitable fruit or vegetable materials include, but are not limited to, carrot, orange, grapefruit, apple, beet, turnip, parsnip, tomato, beans and other legumes, celery, spinach, lettuce, parsley, watercress, and mixtures thereof. Table 1 below summarizes the composition of some exemplary fruit and vegetable pomaces (all values in wt %). Carrot pomace and orange pomace are particularly preferred because of their favorably high ratio of soluble to insoluble fiber. Carrots for use in the invention include all varieties and subspecies of *Daucus carrota*, such as *Daucus carrota sativus*. The carrots can have any color, such as orange, red, yellow, purple, or white. Carrots used to prepare carrot pomace for use in the invention can be devoid of the upper leafy portion of the carrot plant (the "greens") or can include the greens or a portion of the greens, such as a portion of the greens at the top of the carrot which is embedded in the lower portion of the carrot.

A pomace for use in the invention preferably contains from about 40 wt % to about 75 wt % total dietary fiber, preferably from about 45 wt % to about 55 wt % total dietary fiber, including from about 10 wt % to about 50 wt % soluble fiber, preferably from about 15 wt % to about 30 wt % soluble fiber, with the rest of the total dietary fiber being insoluble fiber. Preferably, the pomace has a weight ratio of soluble to insoluble fiber of from about 0.25 to about 2, more preferably from about 0.3 to about 1.5, even more preferably from about 0.6 to about 1.4. Fruit or vegetable pomace for use in the invention can be in the form of dry granules or dry powder, having particles of any desired size range, or can be provided in the form of a mash with high water content, or as an aqueous suspension.

TABLE 1

Composition of Fruit and Vegetable Pomaces.

| Component | Carrot Pomace Carrot Pomace Powder (CPP)[1] | Carrot Pomace Pectin-depleted Hydro bind ™[2] | Orange Pomace Citri-fi ®100[3] | Apple Pomace FruitSmart ® Apple Fiber[4] |
|---|---|---|---|---|
| Total dietary fiber | 55.6 | 92.0 | 68.2 | 44.1 |
| Soluble Fiber | 22.6 | 14.0 | 33.3 | 11.9 |
| Insoluble Fiber | 31 | 78.0 | 34.9 | 32.2 |
| Sugar | 21.4 | | 7.36 | 32.2 |
| Protein | 6.9 | | 8.15 | 3.8 |
| Total Fat | 0.5 | | 1.05 | 1.6 |
| Ash | 5 | 5.3 | 2.65 | 1.8 |
| Moisture | 10 | 10.0 max | 7.42 | |

[1]Transimpex GmbH, Neustadter Str. 1a, 67245 Lambsheim, Germany.
[2]Wm. Bolthouse Farms Europe, 43 Lake Crest Circle, Atlanta, GA 30024.
[3]Fiberstar, Inc., 713 St. Croix St., River Falls, WI 54022.
[4]FruitSmart, 201 Euclid Rd., Grandview, WA 98930

A fruit or vegetable pomace for use in the invention is a fiber preparation containing both soluble and insoluble fiber in a ratio that is substantially similar to that in native plant tissue. One form of fruit or vegetable pomace is carrot pomace powder (CPP), which is a by-product of a commercial carrot juicing operation. Carrot pomace for use in the invention contains dietary fiber as a major component (from about 45 wt % to about 55 wt % dietary fiber, or from about 45 wt % to about 60 wt %, or in some embodiments from about 50 to about 60 wt % dietary fiber, based on dry weight), which includes both soluble fiber and insoluble fiber. Fruit or vegetable pomace for use in the invention may include additional minor components, such as water, sugars, glycoproteins, proteins, peptides, fats, carrotenes, phytosterols, phenols, other biomolecules, minerals, and electrolytes.

A "whole fruit or vegetable powder" as used herein refers to a solid material obtained from a fruit or vegetable material, or mixture of fruit and vegetable materials, by a process including dehydration without prior removal of the juice present in the fruit or vegetable material.

As used herein, "soluble fiber" refers to the water soluble or gel-forming fiber fraction of plant material, and especially of carrot fiber, which can be broken down and typically fermented to produce short chain fatty acids by large bowel flora in the mammalian GI system. Soluble fiber includes polysaccharides such as pectin, inulin, alginate, raffinose, and vegetable bean gums (e.g., guar gum and locust bean gum). Preferred soluble fiber is pectin, which is a group of heteropolysaccharides that originate from plant cell walls and are rich in galacturonic acid. Four species are common: homogalacturonan (HGA, a linear polymer), rhamnogalacturonans I and II (RGI and RGII, highly branched polymers), and xylogalacturonan (XGA). The pectin backbone contains branched or unbranched polymer of galacturonic acid with additional sugars, including xylose, apiose, rhamnose, galactose, and arabinose, which may be included in the backbone or appended to the backbone. Many of the galacturonic acid residues in pectin are esterified, but some remain in the acidic form. The molecular weight of pectin polymers ranges from 60-130,000 g/mol.

"Insoluble fiber" as used herein refers to the water insoluble fiber fraction of plant material, and especially of carrot fiber, which is not broken down for glucose absorption by the mammalian small intestine and typically is not fermented by the large bowel flora. Insoluble fiber includes plant cell wall polysaccharides such as cellulose, hemicellulose, lignin. chitin, and xanthan. Lignin is composed of aromatic alcohol subunits, and is more hydrophobic than cellulose, hemicellulose and pectin.

Methods for determining the amounts of soluble and insoluble fiber in a plant-based food material, such as a pomace, are known. For example, American Association for Clinical Chemistry (AACC) approved gravimetric and liquid chromatography-based methods are reviewed in B. C. McLeary, et al., Cereal Foods World 56, 238-247 (2011).

As used herein, "normal blood glucose concentration" refers to the concentration of glucose in blood present in a normal individual, i.e., an individual who does not have any form of diabetes or other diseases of glucose physiology. It is understood that even in a normal subject the blood glucose concentration fluctuates according to physiological condition and recent consumption of food.

Tests exist which take such fluctuations into account and are capable of determining whether a subject's blood glucose concentration or its fluctuation is normal. Such tests are, for example, the oral glucose tolerance test (OGTT), random blood glucose (RBG) assessment. and fasting blood glucose (FBG) test. Any of these tests can be used to detect, for example, a normal blood glucose concentration indicating the absence of diabetes (non-diabetic profile), or an elevated blood glucose concentration that can indicate a form of diabetes. By "achieving" a normal blood glucose concentration is meant the conversion of abnormal blood glucose concentration, measured using the above-mentioned or other accepted blood glucose measurements, to normal blood glucose concentration over time as the result of a treatment according to the invention. For example, a mammal having a form of diabetes (elevated blood glucose) is treated and then attains a normal blood glucose concentration. By "maintaining" normal blood glucose concentration is meant that a mammalian subject having normal blood glucose continues to have normal blood glucose over time, especially where a subject, such as a prediabetic subject, is expected to develop abnormal blood glucose when not treated according to the invention.

A "diabetogenic diet" is a diet that is likely to lead to the development of a form of diabetes, such as type 2 diabetes, over time by continued consumption of the diet. If the same subject does not consume the diabetogenic diet, but consumes a non-diabetogenic diet rendered as such by simultaneous treatment with a fruit or vegetable pomace such as carrot pomace, then the subject will not develop diabetes over time. A diabetogenic diet can be, for example, a high carbohydrate diet, especially a diet rich in processed, rapidly released and quickly absorbed carbohydrates, which leads to the development of glucose intolerance if consumed in sufficient quantity over sufficient time.

The term "carbohydrate-rich diet" or "high carbohydrate diet" refers to a diet in which the carbohydrate calories represent at least 40% of the total energy consumed, and more typically 50% or 60% or even 70% of the total energy consumed. The percentage of the total dietary energy (kilocalories) provided by carbohydrates is calculated for a diet in which total dietary energy includes energy (calories) from carbohydrate, fat, and protein. For the purposes of defining "carbohydrate-rich" only those carbohydrates are counted that are either energy-generating monosaccharides or polysaccharides that are digested to such energy-generating monosaccharides.

The term "diet" refers to food and beverage intake averaged over a period of time, i.e., more than 7 days, i.e., 10, 15, 20, 25 or 30 days or more than one month, i.e., 2, 3, or 4 months. The terms "solid formula diet," "liquid formula diet," and "meal replacement" refer herein to pre-made, commercially prepared and packaged, nutritional compositions that serve as either substitutes or supplements to meals. The primary function of formula diets and meal replacements is weight loss without needing to count dietary calories. Liquid formula diets and meal replacements are typically protein-based and used in combination with a low-calorie diet in which a dieter may consume on the order of 1000 kcal per day.

The term "nutritional composition" as used herein refers to any composition of matter suitable for consumption as a food or beverage by a mammalian subject. Generally, the term refers to a prepared food or beverage composition that contains two or more natural ingredients, purified ingredients, or synthetic ingredients, and provides some measure of nutrition for the subject when consumed. A "dietary composition" is a nutritional composition that is intended to serve as a complete source of nutrition for the subject that consumes it for a period of time. A nutritional composition or dietary composition is administered "periodically" if it is administered at regular or irregular intervals over a period of time, such as daily, several times a day, or several times a week, over at least one week, preferably over 2-4 weeks, more preferably over at least 4 weeks, or at least 6 weeks, 8 weeks, 10 weeks, 12 weeks, or 4 months, 5 months, or 6 months. In a preferred embodiment, a nutritional or dietary composition of the invention is administered together with, or just before or after, a meal, such as a high carbohydrate meal. In preferred embodiments, nutritional or dietary compositions of the invention are liquid.

A "subject" according to the invention is a mammal, such as a human, house pet, or livestock animal, that receives and consumes a composition according to the invention.

A "disease or condition related to carbohydrate metabolism" as referred to herein is a disease or medical condition involving an abnormality of carbohydrate metabolism. The term "carbohydrate metabolism" refers to one or more of the biochemical pathways by which ingested carbohydrates, including digestible and non-digestible carbohydrates such as sugars, starches, celluloses and numerous other polysaccharides, are either absorbed into the bloodstream and metabolized or not absorbed into the bloodstream and passed into the large intestine where they are utilized by microbial flora or not utilized and are eliminated in the feces.

The term "prediabetic" refers herein to the status of a subject, based on the subject's blood glucose concentration, as transitioning from normal to a diabetic condition. Prediabetic subjects are a sub-group within the larger status group of "diabetic" subjects. The prediabetic status can be used to detect impending diabetes and is defined by blood glucose threshold levels measured using either FBG, RBG, or OGTT tests, or preferably measured using RBG together with OGTT, or more preferably all three tests together, in milligrams glucose per deciliter of blood (mg/dl) for humans and other mammals, including the Nile rat. For the normal Nile rat, FBG ranges from 40-60 mg/dl, while the normal RBG measured value remains below the prediabetic threshold of 75 mg/dl. Finally the OGTT value measured 30 min after glucose administration does not exceed the prediabetic value of 150 mg/dl in the Nile rat. For prediabetic humans, the FBG ranges from 100 to 124 mg/dl, while RBG remains below the diabetic threshold value of 150 mg/dl, whereas the OGTT measured value does not exceed the 175 mg/dl diabetic threshold. The coupled FBG, RBG, and OGTT measurements are diagnostic for detecting the prediabetic condition, with the OGTT measurement being more sensitive for early detection of type 2 diabetes than RGB, and both are more sensitive than FBG, which provides a strong but delayed signal.

The term "diabetic" refers herein to a disease or condition of carbohydrate metabolism characterized by the blood glucose status of a mammal. The diabetic state is defined by a blood glucose threshold level, measured in milligrams of glucose per deciliter of blood (mg/dl), that exceeds a defined threshold value for any one (or more) of the following measurements: OGTT, RBG and FBG (see Table 2). These threshold values are approximately 2-fold lower for Nile rats than for humans (except for the OGTT). The Nile rat evolved to survive in a carbohydrate-poor desert environment, and when subjected to a carbohydrate-rich diet develops T2DM much more readily and with blood glucose levels that are lower than for humans. Comparative threshold values are provided below in Table 2 for: (a) fasting blood glucose (FBG), (b) random blood glucose (RBG), and (c) oral glucose tolerance test (OGTT).

TABLE 2

Threshold Blood Glucose Levels for Diagnosis of Type 2 Diabetes

| Test Method | | Nile Rats (mg/dl) | Humans (mg/dl) |
|---|---|---|---|
| FBG | Healthy | ≤60 | ≤125 |
| | Diabetic | >60 | >125 |
| RBG | Healthy | ≤75 | ≤150 |
| | Diabetic | >75 | >150 |
| OGTT | Healthy | ≤150 | ≤175 |
| (30 min) | Diabetic | >150 | >175 |

"Treating" a disease or condition related to carbohydrate metabolism means that, in response to a method or composition of the invention, some measure of improvement is obtained in the subject's disease or condition, as measurable by at least one health index related to the disease or condition, such as blood glucose concentration, incidence, attainment, or progression of type 2 diabetes, body weight gain, fatty liver, enlarged kidneys, or the like. Treatment of a disease or condition of carbohydrate metabolism can be synonymous with "controlling" the disease or condition; control, such as by dietary intervention, provides effective treatment, but only for as long as the intervention is continued. "Preventing" such a disease or condition refers to any measure of delay of onset of the disease or condition, up to and including, but not requiring, completely preventing the disease or condition from occurring. Preventing may also include averting the occurrence of one or more aspects of the disease or condition, but not necessarily averting other aspects or all aspects of the disease or condition from occurring. Preventing may also refer to avoiding the worsening or development of a disease or condition.

The invention can be further summarized by the following list of embodiments.

1. A method of maintaining or achieving normal blood glucose concentration in response to a diabetogenic diet in a mammalian subject, the method comprising periodically administering to a mammalian subject consuming a diabetogenic diet a nutritional composition comprising fruit or vegetable pomace, whereby the subject's blood glucose concentration is maintained within a normal range or achieves a value within a normal range.

1a. The method of embodiment 1, wherein said pomace is a pomace obtained from a fruit or vegetable selected from the group consisting of carrot, orange, grapefruit, apple, beet, tomato, beans and other legumes, celery, spinach, lettuce, parsley, watercress, and mixtures thereof.

1b. The method of embodiment 1a, wherein said pomace is carrot pomace.

2. The method of any of embodiments 1, 1a, and 1b, wherein said pomace provides at least 20% of the recommended daily intake of dietary fiber for the subject.

3. The method of any of the previous embodiments, wherein said diabetogenic diet provides at least 40% of the subject's dietary energy in the form of carbohydrate.

4. The method of any of the previous embodiments, wherein the pomace comprises a mixture of soluble fiber and insoluble fiber.

5. The method of embodiment 4, wherein the weight ratio of soluble to insoluble fiber in the carrot pomace is from about 0.6 to about 1.4.

6. The method of any of embodiments 4-5, wherein the insoluble fiber is selected from the group consisting of cellulose, hemicellulose, lignin, and combinations thereof.

7. The method of any of embodiments 4-6, wherein the soluble fiber comprises pectin.

8. The method of any of the previous embodiments, wherein the pomace is carrot pomace which is produced by a method comprising heat treatment and juice extraction of carrots, and drying and comminution of the residue.

9. The method of embodiment 8, wherein the carrot pomace is produced by a method comprising heat treatment sufficient to raise the carrot tissue to a temperature in the range from about 120° F. to about 200° F.

10. The method of any of embodiments 8-9, wherein the carrot pomace is produced by a method comprising release of at least 40% of the carrot weight as juice, the juice containing at least 3.5 wt % sugar.

11. The method of any of embodiments 8-10, wherein the carrot pomace is produced by a method that does not include alkaline treatment, bleach treatment, or fiber-denaturing heat treatment.

12. The method of any of the previous embodiments, wherein said maintaining normal blood glucose is determined using a random blood glucose test.

13. The method of any of embodiments 1-11, wherein said maintaining normal blood glucose is determined using an oral glucose tolerance test.

14. The method of any of embodiments 1-11, wherein said maintaining normal blood glucose is determined using a fasting blood glucose test.

15. The method of any of the previous embodiments, wherein normal blood glucose is more effectively maintained compared to periodic administering of an equivalent amount of cellulose or inulin dietary fiber.

16. The method of any of the previous embodiments, wherein the nutritional composition is selected from the group consisting of foods, beverages, dietary supplements, nutraceuticals, and dietary formulations.

17. The method of embodiment 16, wherein the nutritional composition is pet food.

18. The method of embodiment 16, wherein the nutritional composition is a reduced carbohydrate food, beverage, or dietary formulation.

19. The method of any of embodiments 1-16 and 18, wherein the subject is human.

20. The method of embodiment 19, wherein the human has or is at risk of developing type 2 diabetes or obesity.

21. The method of any of the previous embodiments, wherein the subject experiences weight loss.

22. The method of any of the previous embodiments, wherein the progression or onset of diabetes in the subject is delayed or halted.

23. The method of any of embodiments 1-18 and 21-22, wherein the subject is a house pet or livestock animal.

24. The method of any of the previous embodiments, wherein from about 40% to about 70% of the subject's caloric intake is provided by carbohydrate.

25. The method of any of the previous embodiments, wherein the nutritional composition is administered daily over a period of at least four weeks.

26. A method to aid in treating or preventing a disease or condition related to carbohydrate metabolism, the method comprising periodically administering to a subject in need thereof a nutritional composition comprising fruit or vegetable pomace, whereby at least one symptom of the disease or condition is reduced or the onset or progression of the disease or condition is delayed or prevented.

27. The method of embodiment 26, wherein said pomace is a pomace obtained from a fruit or vegetable selected from the group consisting of carrot, orange, grapefruit, apple, beet, tomato, beans and other legumes, celery, spinach, lettuce, parsley, watercress, and mixtures thereof.

28. The method of embodiment 27, wherein said pomace is carrot pomace.

29. The method of any of embodiments 26-28, wherein the disease or condition is selected from the group consisting of type 1 diabetes mellitus, type 2 diabetes mellitus, gestational diabetes mellitus, prediabetes, metabolic syndrome, and obesity.

30. The method of embodiment 29, wherein the disease or condition is type 2 diabetes mellitus.

31. The method of any of embodiments 26-30, wherein the onset or progression is delayed or prevented.

32. The method of any of embodiments 26-31, wherein the subject is prediabetic, and the onset of type 2 diabetes mellitus is delayed or prevented.

33. The method of any of embodiments 26-32, wherein the subject has type 2 diabetes mellitus, and the progression of the diabetes is halted.

34. The method of any of embodiments 26-33, wherein the subject is obese and experiences weight loss.

35. The method of any of embodiments 26-34, wherein said pomace provides at least 20% of the recommended daily intake of dietary fiber for the subject.

36. The method of any of embodiments 26-35, wherein the pomace comprises a mixture of soluble fiber and insoluble fiber.

37. The method of embodiment 36, wherein the weight ratio of soluble to insoluble fiber is from about 0.6 to about 1.4.

38. The method of embodiment 36 or 37, wherein the insoluble fiber is selected from the group consisting of cellulose, hemicellulose, lignin, and combinations thereof.
39. The method of any of embodiments 36-38, wherein the soluble fiber comprises pectin.
40. The method of any of embodiments 26-39, wherein the pomace is carrot pomace which is produced by a method comprising heat treatment, juice extraction, drying, and comminution.
41. The method of embodiment 40, wherein the carrot pomace is produced by a method comprising heat treatment sufficient to raise the carrot tissue to a temperature in the range from about 120° F. to about 200° F.
42. The method of any of embodiments 40-41, wherein the carrot pomace is produced by a method comprising release of at least 40% of the carrot weight as juice, the juice containing at least 3.5 wt % sugar.
43. The method of any of embodiments 40-42, wherein the carrot pomace is produced by a method that does not include alkaline treatment, bleach treatment, or fiber-denaturing heat treatment.
44. The method of any of embodiments 26-43, further comprising measuring blood glucose using a random blood glucose test.
45. The method of any of embodiments 26-43, further comprising measuring blood glucose using an oral glucose tolerance test.
46. The method of any of embodiments 26-43, further comprising measuring blood glucose using a fasting blood glucose test.
47. The method of any of embodiments 26-46, wherein said disease or condition is more effectively treated or prevented compared to periodic administering of an equivalent amount of cellulose or inulin dietary fiber.
48. The method of any of embodiments 26-47, wherein the nutritional composition is selected from the group consisting of foods, beverages, dietary supplements, nutraceuticals, and dietary formulations.
49. The method of embodiment 48, wherein the nutritional composition is pet food.
50. The method of any of embodiments 48-49, wherein the nutritional composition is a reduced carbohydrate food, beverage, or dietary formulation.
51. The method of embodiment any of embodiments 26-50, wherein the subject is human.
52. The method of any of embodiments 26-50, wherein the subject is a house pet or livestock animal.
53. The method of any of embodiments 26-52, wherein from about 40% to about 70% of the subject's caloric intake is provided by carbohydrate.
54. The method of any of embodiments 26-53, wherein the nutritional composition is administered daily over a period of at least four weeks.
55. The method of any of embodiments 26-54, wherein the subject's total plasma cholesterol and/or plasma triglycerides are reduced.
56. The method of any of embodiments 26-55, wherein the subject has hyperlipidemia, hypercholesterolemia, and/or elevated triglycerides.
57. A nutritional composition comprising fruit or vegetable pomace for use in maintaining or achieving normal blood glucose concentration in response to a diabetogenic diet in a mammalian subject.
58. The nutritional composition of embodiment 57, wherein said pomace is a pomace obtained from a fruit or vegetable selected from the group consisting of carrot, orange, grapefruit, apple, beet, tomato, beans and other legumes, celery, spinach, lettuce, parsley, watercress, and mixtures thereof.
59. The nutritional composition of embodiment 58, wherein said pomace is carrot pomace.
60. The nutritional composition of any of embodiments 57-59, wherein said diabetogenic diet provides at least 40% of the subject's dietary energy in the form of carbohydrate.
61. The nutritional composition of any of embodiments 57-60, wherein the pomace comprises a mixture of soluble fiber and insoluble fiber.
62. The nutritional composition of embodiment 61, wherein the weight ratio of soluble to insoluble fiber in the pomace is from about 0.6 to about 1.4.
63. The nutritional composition of any of embodiments 61-62, wherein the insoluble fiber is selected from the group consisting of cellulose, hemicellulose, lignin, and combinations thereof.
64. The nutritional composition of any of embodiments 61-63, wherein the soluble fiber comprises pectin.
65. The nutritional composition of any of embodiments 57-64, wherein the pomace is carrot pomace which is produced by a method comprising heat treatment and juice extraction of carrots, and drying and comminution of the residue.
66. The nutritional composition of embodiment 65, wherein the carrot pomace is produced by a method comprising heat treatment sufficient to raise the carrot tissue to a temperature in the range from about 120° F. to about 200° F.
67. The nutritional composition of any of embodiments 65-66, wherein the carrot pomace is produced by a method comprising release of at least 40% of the carrot weight as juice, the juice containing at least 3.5 wt % sugar.
68. The nutritional composition of any of embodiments 65-67, wherein the carrot pomace is produced by a method that does not include alkaline treatment, bleach treatment, or fiber-denaturing heat treatment.
69. The nutritional composition of any of embodiments 57-68, wherein the nutritional composition is selected from the group consisting of foods, beverages, dietary supplements, nutraceuticals, and dietary formulations.
70. The nutritional composition of embodiment 69, wherein the nutritional composition is pet food.
71. The nutritional composition of any of embodiments 69-70, wherein the nutritional composition is a reduced carbohydrate food, beverage, or dietary formulation.
72. The nutritional composition of any of embodiments 57-69 and 71, wherein the subject is human.
73. The nutritional composition of embodiment 72, wherein the human has or is at risk of developing type 2 diabetes or obesity.
74. The nutritional composition of any of embodiments 57-73, which is also for use in promoting weight loss in the subject.
75. The nutritional composition of any of embodiments 73-74, which is also for use in delaying or halting the progression or onset of diabetes in the subject.
76. The nutritional composition of any of embodiments 57-75, which is also for use in lowering plasma cholesterol and/or plasma triglycerides.
77. The nutritional composition of any of embodiments 57-76, wherein the subject has or is at risk of developing hyperlipidemia, hypercholesterolemia, and/or elevated triglycerides.
78. The nutritional composition of any of embodiments 57-71 and 74-75, wherein the subject is a house pet or livestock animal.

79. The nutritional composition of any of embodiments 57-78, wherein from about 40% to about 70% of the subject's caloric intake is provided by carbohydrate.

80. The nutritional composition of any of embodiments 57-79, wherein said use comprises administration daily over a period of at least four weeks.

81. A nutritional composition comprising fruit or vegetable pomace for use in treating or preventing a disease or condition related to carbohydrate metabolism in a subject.

82. The nutritional composition of embodiment 81, wherein said pomace is a pomace obtained from a fruit or vegetable selected from the group consisting of carrot, orange, grapefruit, apple, beet, tomato, beans and other legumes, celery, spinach, lettuce, parsley, watercress, and mixtures thereof.

83. The nutritional composition of claim 82, wherein said pomace is carrot pomace.

84. The nutritional composition of any of embodiments 81-83, wherein said use results in at least one symptom of the disease or condition being reduced or the onset or progression of the disease or condition being delayed or prevented.

85. The nutritional composition of any of embodiments 81-84, wherein the disease or condition is selected from the group consisting of type 1 diabetes mellitus, type 2 diabetes mellitus, gestational diabetes mellitus, prediabetes, metabolic syndrome, and obesity.

86. The nutritional composition of any of embodiments 81-85, wherein the subject is prediabetic, and the onset of type 2 diabetes mellitus is delayed or prevented.

87. The nutritional composition of any of embodiments 81-86, wherein the subject has type 2 diabetes mellitus, and the progression of the diabetes is halted.

88. The nutritional composition of any of embodiments 81-87, wherein the pomace comprises a mixture of soluble fiber and insoluble fiber.

89. The nutritional composition of any of embodiments 81-88, wherein the weight ratio of soluble to insoluble fiber in the pomace is from about 0.6 to about 1.4.

90. The nutritional composition of any of embodiments 88-89, wherein the insoluble fiber is selected from the group consisting of cellulose, hemicellulose, lignin, and combinations thereof.

91. The nutritional composition of any of embodiments 88-90, wherein the soluble fiber comprises pectin.

92. The nutritional composition of any of embodiments 81-91, wherein the pomace is carrot pomace which is produced by a method comprising heat treatment and juice extraction of carrots, and drying and comminution of the residue.

93. The nutritional composition of embodiment 92, wherein the carrot pomace is produced by a method comprising heat treatment sufficient to raise the carrot tissue to a temperature in the range from about 120° F. to about 200° F.

94. The nutritional composition of any of embodiments 92-93, wherein the carrot pomace is produced by a method comprising release of at least 40% of the carrot weight as juice, the juice containing at least 3.5 wt % sugar.

95. The nutritional composition of any of embodiments 92-94, wherein the carrot pomace is produced by a method that does not include alkaline treatment, bleach treatment, or fiber-denaturing heat treatment.

96. The nutritional composition of any of embodiments 81-95, wherein the nutritional composition is selected from the group consisting of foods, beverages, dietary supplements, nutraceuticals, and dietary formulations.

97. The nutritional composition of embodiment 96, wherein the nutritional composition is pet food.

98. The nutritional composition of any of embodiments 96-97, wherein the nutritional composition is a reduced carbohydrate food, beverage, or dietary formulation.

99. The nutritional composition of any of embodiments 81-98, wherein the subject is human.

100. The nutritional composition of any of embodiments 81-98, wherein the subject is a house pet or livestock animal.

101. The nutritional composition of any of embodiments 81-98, wherein said use comprises administration daily over a period of at least four weeks.

102. A nutritional composition prepared by supplementation of a food, beverage, or dietary composition with fruit or vegetable pomace, wherein the pomace is unbleached, pectinase-free, and sugar-reduced; and wherein periodic administration of the nutritional composition to a mammalian subject in need thereof maintains or achieves normal blood glucose concentration of the subject.

103. The nutritional composition of embodiment 102, wherein said pomace is a pomace obtained from a fruit or vegetable selected from the group consisting of carrot, orange, grapefruit, apple, beet, tomato, beans and other legumes, celery, spinach, lettuce, parsley, watercress, and mixtures thereof.

104. The nutritional composition of embodiment 103, wherein said pomace is carrot pomace.

105. The nutritional composition of any of embodiments 102-104 which is formulated as a food product, beverage, nutritional supplement, nutraceutical, or dietary formulation.

106. The nutritional composition of any of embodiments 102-105, wherein the pomace comprises a mixture of soluble fiber and insoluble fiber.

107. The nutritional composition of embodiment 106, wherein the weight ratio of soluble to insoluble fiber is from about 0.6 to about 1.4.

108. The nutritional composition of any of embodiments 106-107, wherein the insoluble fiber is selected from the group consisting of cellulose, hemicellulose, lignin, and combinations thereof.

109. The nutritional composition of any of embodiments 106-108, wherein the soluble fiber comprises pectin.

110. The nutritional composition of any of embodiments 102-109, wherein the pomace is carrot pomace which is produced by a method comprising heat treatment, juice extraction, drying, and comminution.

111. The nutritional composition of embodiment 110, wherein the carrot pomace is produced by a method comprising heat treatment sufficient to raise the carrot tissue to a temperature in the range from about 120° F. to about 200° F.

112. The nutritional composition of any of embodiment 110-111, wherein the carrot pomace is produced by a method comprising release of at least 40% of the carrot weight as juice, the juice containing at least 3.5 wt % sugar.

113. The nutritional composition of any of embodiments 110-112, wherein the carrot pomace is produced by a method that does not include alkaline treatment, bleach treatment, or fiber-denaturing heat treatment.

114. The nutritional composition of any of embodiments 102-113 that comprises at least 10 wt %, on a dry weight basis, of pomace.

115. The nutritional composition of any of embodiments 102-114 that comprises 2-5 wt %, on a dry weight basis, of pomace.

116. The nutritional composition of any of embodiments 102-115 that is formulated as a dietary formulation, wherein the formulation comprises an amount of pomace sufficient to provide at least 20% of the required daily intake of dietary fiber for the subject.

117. The method of any of embodiments 1-56, wherein a ratio of *Prevotella* bacteria to *Bacteroides* bacteria is increased in the subject's intestinal microbiome.

118. The method of any of embodiments 1-56 or 117, wherein bacteria of the genus *Lactobacillus* are decreased as a percentage of the subject's intestinal microbiome.

119. The method of any of embodiments 1-56 or any of embodiments 117-118, wherein the subject's postprandial blood glucose level, measured as the area under the curve (AUC) at two hours in an oral glucose tolerance test, is lowered.

120. The method of embodiment 119, wherein the subject is human and consumes at least 10 g of carrot pomace per day, and wherein the subject's glucose AUC at two hours in an oral glucose tolerance test is reduced by at least about 25% compared to without consumption of carrot pomace.

121. The nutritional composition of any of embodiments 57-116, wherein said use increases bacteria of the Erysipelotrichaceae family as a percentage of the subject's intestinal microbiome.

122. The nutritional composition of any of embodiments 57-116 and 121, wherein said use increases a ratio of *Prevotella* bacteria to *Bacteroides* bacteria in the subject's intestinal microbiome.

123. The nutritional composition of any of embodiments 57-116 and 121-122, wherein said use decreases bacteria of the genus *Lactobacillus* as a percentage of the subject's intestinal microbiome.

BRIEF DESCRIPTION OF THE DRAWINGS

FIGS. 3A and 3B show the top phyla (FIG. 3A) and top 10 families (FIG. 3B) of bacteria found in Nile rat feces after consumption of the Lentils Diet.

FIGS. 4A and 4B show the top phyla (FIG. 4A) and top 10 families (FIG. 4B) of bacteria found in Nile rat feces after consumption of the Chow Diet.

FIGS. 5A and 5B show the top phyla (FIG. 5A) and top 10 families (FIG. 5B) of bacteria found in Nile rat feces after consumption of Diet 133A.

FIGS. 6A and 6B show the top phyla (FIG. 6A) and top 10 families (FIG. 6B) of bacteria found in Nile rat feces after consumption of Diet 133B.

FIGS. 7A and 7B show the top phyla (FIG. 7A) and top 10 families (FIG. 7B) of bacteria found in Nile rat feces after consumption of Diet 151.

FIGS. 8A and 8B show the top phyla (FIG. 8A) and top 10 families (FIG. 8B) of bacteria found in Nile rat feces after consumption of Diet 152.

FIGS. 9A and 9B show the top phyla (FIG. 9A) and top 10 families (FIG. 9B) of bacteria found in Nile rat feces after consumption of Diet 153.

FIGS. 10A and 10B show the top phyla (FIG. 10A) and top 10 families (FIG. 10B) of bacteria found in Nile rat feces after consumption of Diet 73MBS+PFJ.

FIGS. 13A-13C show the changes in *Prevotella* and *Bacteroides* bacteria in the microbiota of Nile rats fed the indicated diets as described in Example 7. The order of the diets from left to right is the same in FIGS. 13A, 13B, and 13C.

DETAILED DESCRIPTION OF THE INVENTION

Figures 1A, 1B, 2A, 2B:
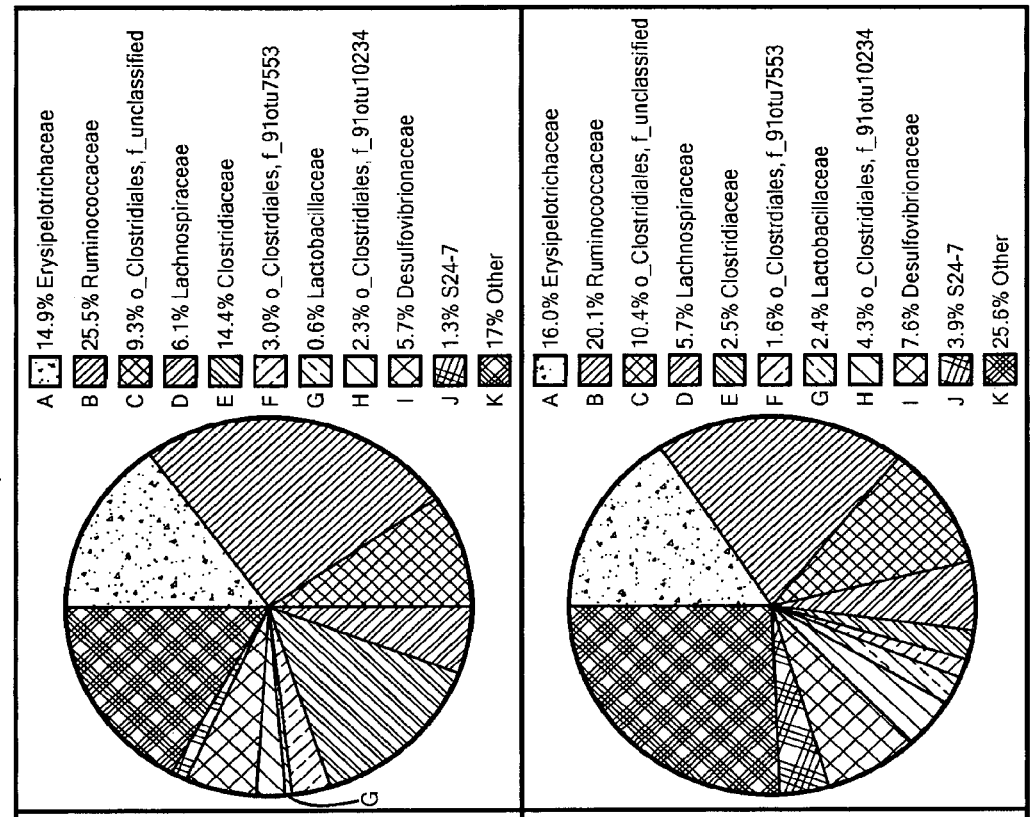
FIGS. 1A and 1B show the top phyla (FIG. 1A) and top 10 families (FIG. 1B) of bacteria found in Nile rat feces after consumption of Diet 73MBS.
FIGS. 2A and 2B show the top phyla (FIG. 2A) and top 10 families (FIG. 2B) of bacteria found in Nile rat feces after consumption of Diet 133.

The invention provides compositions and methods for dietary modulation useful to prevent and control metabolic syndrome, type 2 diabetes mellitus, and other diseases related to carbohydrate metabolism. The present inventors have discovered that administration of nutritional compositions including fruit or vegetable pomace to a mammalian subject surprisingly can reduce the subject's blood glucose levels and effectively control or treat type 2 diabetes in the subject, or even prevent the development of type 2 diabetes from developing from prediabetes, as well as control body weight gain or lead to weight loss.

The present invention goes beyond just increasing dietary fiber content. Certain fiber preparations such as fruit or vegetable pomace have been shown to have unique and useful properties, which are believed due to their fiber composition, and in particular due to the complex of soluble and insoluble fiber components found therein. As described below, the composition and structure of fruit or vegetable tissue can be modified to provide the presently described functionalities. For example, carrot tissue contains only approximately 5% by weight of solids, and moist carrot pomace derived from the juicing of carrots still contains only approximately 10% solids by weight. By comparison, the dried carrot pomace used in the invention is 20-fold concentrated compared to native carrots. Therefore, if 5% by weight CPP is included in a nutritional composition, such as a can of pet food for example, the pet food contains the equivalent of 100% full strength carrots in terms of fiber, while the remaining 95% of the food product can be formulated according to any pre-planned recipe. It would be impossible to add a sufficient amount of fresh or cooked carrots (containing approximately 2.5% by weight dietary fiber) to provide a meaningful amount of dietary fiber in a processed food product. On the other hand, with the dietary supplements, processed medicinal foods, meal replacements, and liquid formula diets of the present invention, which are supplemented with fruit or vegetable pomace, it is feasible and practical to formulate and provide 20% or more of the current RDI (recommended daily intake) of dietary fiber using such a pomace. A calculation shows that at 20% of the RDI of dietary fiber (25 g per day and 5 g fiber, respectively), the 5 g quantity of fiber needed can be provided by 10 g of carrot pomace. This amount of carrot pomace can be easily integrated into a meal in the form of baked goods (breads, muffins, cakes, crackers, cold cereals), hot cereals, soups, stews, mashed vegetables, hummus-type spreads, nut butters, beverages such as tomato juice, milk, and the like.

Fruit or vegetable pomace can be used to maintain or achieve normal blood glucose, and therefore can be used to treat or prevent a variety of diseases or medical conditions of carbohydrate metabolism, such as type 2 diabetes. Further, because there is a relationship between consumption of high glycemic foods and cardiac disease, as well as related conditions such as hyperlipidemia, hypercholesterolemia, and elevated triglycerides (31), the use of dietary fiber sources according to the invention also can be used to treat or prevent these diseases and conditions, and to lower plasma cholesterol and plasma triglycerides.

Fruit and Vegetable Fiber Compositions

A fiber composition for use in the present invention can be a pomace material obtained from the juicing of any fruit or vegetable matter. Preferably, the fruit or vegetable matter is first heated, then juice is extracted from the material, following which the remaining pomace is dried and ground or comminuted. The fiber composition contains a mixture of soluble and insoluble fiber, which can originate from the same fruit or vegetable matter, or from a combination of different fruit or vegetable materials, or from an artificial, synthetic, or purified natural fiber source.

While the use of fruit or vegetable pomace as the source of dietary fiber in the invention is preferred, a less preferred alternative is to use whole fruit or vegetable powder, such as for example, dried whole carrot powder, which can be mixed into foods and beverages and administered to a mammal in need thereof, just as a pomace can. Such whole fruit or vegetable powders are less preferred because they are a less concentrated source of dietary fiber than pomace, and because they have a higher sugar content. For example, whole carrot powder contains 26.4 wt % dietary fiber and 38.8 wt % sugars (see nutritiondata.self.com/facts/vegetables-and-vegetable-products/7365/2), compared to CPP which contains 55.6 wt % dietary fiber and 21.4 wt % sugars (Table 1 above).

Certain physical and chemical changes occur in plant tissue in the process of making fruit or vegetable pomace. For example, pomace can be obtained from a process of juicing fruits or vegetables in which the tissue of fresh fruit or vegetable matter is exposed one or more times to heat supplied as radiant heat, hot air, hot water (including boiling water), steam, microwave radiation, solar radiation, infrared radiation, or laser energy, for example. The heat source can be applied using a heat exchanger apparatus, a rotating drum, a kettle, a conveyor belt, an irradiation source, or another method. Heat treatment causes important physical expansion of the cellulosic portion of the fiber matrix of plant material. Heat treatment also can inactivate enzymes found in plant tissue, such as pectinase, peroxidase, lipoxygenase, and phenolase. Heat treatment can apply a temperature to the plant material of, for example, 40° C., 50° C., 60° C., 70° C., 80° C., 90° C., 100° C., 110° C., 120° C., 130° C., 140° C., 150° C., 200° C., or even 250° C.; the heat can be applied for a time ranging from seconds to minutes, such as 10 s, 20 s, 30 s, 40 s, 50 s, 1 min, 2 min, 3 min, 4 min, 5 min, 6 min, 7 min, 8 min, 9 min 10 min 12 min, 15 min, or 20 min. The combination of time and temperature can be selected to denature selected enzymes found in the fruit or vegetable material, such as one or more of pectinase, peroxidase, lipoxygenase, and phenolase, and/or to achieve desired physical or chemical changes in the material, such as fiber expansion. Fiber expansion can be coupled with the equally important removal of large amounts of dissolved solids, particularly sugars, from the plant material during the juicing process that precedes drying of the pomace. Reduction in sugar content enables the fiber-rich pomace moving through the GI tract to modulate (i.e., reduce and/or retard) the absorption of nutrients such as sugars into the bloodstream.

When administered to a subject who is consuming a high carbohydrate diet, plant fiber materials such as carrot pomace have the ability to modulate blood glucose levels. The carrot pomace is representative of most fruit and vegetable matter in that its fiber matrix structure includes cellulose, hemicellulose, glycoprotein, and lignin molecules (considered "insoluble fiber") as well as the multiple varieties of pectin polymers (considered "soluble fiber") as described by Harholt et al. (Plant Physiology, June 2010, Vol. 153, pp. 384-395).

Without intending to limit the invention to a particular mechanism, the structure of fruit or vegetable pomace fiber is believed to be a multi-polysaccharide structure analogous to the quaternary structure of multi-polypeptide protein complexes. Complex polysaccharide molecules such as pectin assume a three dimensional tertiary structure, and just as multi-subunit proteins assemble to form higher order quaternary structures, multiple pectinic polysaccharide polymers are believed to assemble onto a core of hemicellulose and cellulose polysaccharides to form quaternary polysaccharide complexes found in carrot pomace fiber. These polysaccharide complexes likely involve hydrogen bonding among pectinic polymer molecules, as well as hydrogen bonding between pectin molecules and hemicellulose and cellulose molecules that form cell wall microfibril structures within carrot tissue. Such higher order hybrid dietary fiber structures (containing both soluble and insoluble fibers) are believed to be more effective in the GI tract for modulating nutrient uptake into the bloodstream than either isolated insoluble fiber (e.g., cellulose) or isolated soluble fiber (e.g., inulin or pectin).

Support for such quaternary structure is provided by Wang et al., Biochemistry 51, 9846-9856 (2012). Using NMR Wang et al. showed that in the intact cell wall, the RGI and HGA pectins in particular form direct connections with approximately 25-50% of the cellulosic chains comprising the surface cellulose of the microfibrils. The interaction between hemicellulose and microfibril cellulose as measured by the NMR cross-peaks between xyloglucan and cellulose appeared weak. Likewise, the protein-cellulose cross-peak signals were weak. The authors presented a model in which the two major classes of insoluble cell wall polysaccharides, i.e., cellulose and hemicellulose, interact with the soluble cell wall polysaccharides, i.e., pectins, to form a defined cell wall structure. In this structure, the cellulose and hemicellulose lie at the interior of the cellulose microfibrils, while the pectins are bound to and decorate the exterior surface of the microfibrils.

An exemplary method of making carrot pomace for use in the invention is as follows. Native carrots, stripped of their greens, are sorted and washed. Whole pieces of carrot or crushed or ground carrot are then blanched, which opens and expands the carrot tissue and facilitates release of carrot juice; for purposes of the present invention, it also at least partially denatures enzymes in the carrot tissue, and preserves the fiber content of the pomace product. This treatment also releases endogenously bound carotenes, including alpha- and beta-carotene, which improves the bioavailability of alpha- and beta-carotenes when carrot pomace is added to foods. The heat treatment also volatilizes undesirable flavors including aldehydes and ketones. Approximately 2" long pieces of hot carrots are then passed through a grinder The resulting hot carrot mash is fed into a high speed centrifuge. In an exemplary commercial process, the centrifuge consists of a substantially horizontal stainless steel pipe with a diameter of approximately 2 feet and a length of approximately 20 feet, which is spinning at about 10,000 rpm. Centrifugation removes carrot juice, which represents from about 40% to about 70% by weight of the carrot mash (typically approximately 50% by weight). The juice contains approximately 4 wt % sugar, including principally sucrose, with additionally some glucose and fructose. Sugar removal from the carrot material is considered not only beneficial but essential for carrot pomace production in order to achieve reduction of blood glucose and control of diabetes. The remaining 50% by weight of the moist carrot mash material is hot pomace mash, which contains approximately 10% by weight solids (dry weight) and 90% by weight trapped moisture and carrot juice. To enable drying, the pomace mash is extruded through a die with approximately ¼ inch holes, yielding a coarse spaghetti-like material with a high surface area that facilitates drying. The extruded material can be placed, for example, on a long stainless steel open mesh (e.g., woven or webbed) belt where hot air is forced through the material until it is dry. The drying conditions preferably should avoid conditions that would denature the fiber quaternary structure.

Dried pomace can be passed through a grinding mill to produce comminuted particles suitably sized for use in a particular nutritional composition, or can be comminuted by other methods. For example, small particles are preferred for some beverage use (e.g., 120 to 130 mesh), while somewhat larger particles (e.g., 30 to 60 mesh) are preferred for dietary supplement use or for addition to solid processed foods for humans and for animals, e.g., bakery batters and doughs, breads, muffins, soups, stews, mashed potatoes and other vegetables, hummus-type spreads, and pet foods.

There are at least two important differences in composition that distinguish dry comminuted carrot pomace particles from dried, comminuted native carrots and dried, comminuted boiled carrots. First, with carrot pomace production, the centrifugation step removes at least 50% of the sugar content of carrots (sucrose, glucose and fructose) in the form of juice. This sugar reduction is important for the antidiabetic use of CPP. Second, limited use of heat and grinding, as well as the absence of washing and extraction with heated water during pomace processing, prevents the loss of pectins that are soluble and otherwise would be extracted from the carrot material. Retaining a high native pectin content, which is believed to bind to the insoluble hemicellulosic/cellulosic microfibrils in carrot fiber, is important for maintaining the biological functionality and activity of carrot pomace in the gastrointestinal tract. By contrast, and as shown in the examples below, administration of separated soluble and insoluble dietary fibers provide poor functionality in controlling blood glucose levels and type 2 diabetes development.

Nile Rat Studies

The Nile rat, like humans, responds favorably to increased fiber consumption and reduction in the dietary glycemic index and glycemic load. With experiments in which different dietary fibers were added at a level of 10% by weight of the diet, carrot fiber provided as carrot pomace powder (CPP) uniquely prevented, delayed, and/or reduced the severity of type 2 diabetes in the Nile rat mammalian model. See Examples 1 and 3 below. The beneficial effects of CPP were unexpectedly greater than for inulin, a favored soluble fiber, and for cellulose, a favored insoluble fiber. Surprisingly, CPP greatly reduced the incidence and even prevented type 2 diabetes disease in these animals based on blood glucose values and necropsy data, while cellulose and inulin often failed. Additionally, with older animals already suffering from type 2 diabetes defined by threshold blood glucose levels being exceeded (see Tables 3, 4 and 5), CPP was able to halt any further progression of the disease. With regard to the results presented in Table 4, it is evident that the diabetic threshold values for the Nile rat are lower than for humans, summarized in Table 2. These differences reflect the much greater sensitivity of the Nile rat to glucose being released and too rapidly absorbed from a carbohydrate-rich diet and can be understood from the animal's survival and genetic evolution in a desert environment largely devoid of rapidly digestible carbohydrate.

Activity of Fruit or Vegetable Pomace

It is widely understood that plant cell wall porosity to metabolites and ionic species is modulated by the variety of different pectin polymer molecules bound to cellulose microfibrils and lignin within the cell wall matrix. In view of evidence that pectins bind to the outer surface of cellulosic microfibrils, and in view of the effects of carrot fiber containing pectin and insoluble fiber on animal model of type 2 diabetes observed herein, it is hypothesized that cellulose microfibril-bound pectins in a quaternary multi-subunit structure can function in the mammalian GI tract to modulate diffusion and transport of glucose. Accordingly, in the mammalian GI tract, the diffusion and absorption of glucose released from digestible carbohydrate-containing foods may be modulated by pectins bound to non-digestible hemicellulose and cellulose. In addition to modulating the glucose absorption rate, the special nature of the CPP fiber has an important bearing on the microbiome activity in the large bowel and the bioactive production of their metabolites affecting the host metabolism of energy once absorbed. As evidenced in the Nile rat Studies 122 and 131 presented in the Examples below, the regular (e.g., daily) ingestion of suitable amounts of carrot fiber containing pectin, believed to be bound to cellulose microfibrils, results in improved control of blood glucose levels and reduced incidence of type 2 diabetes. By comparison, a relatively pure soluble dietary fiber such as pectin or inulin when provided free and unbound to cellulose, is less effective at modulating glucose metabolism or absorption and diabetes control. It appears that pectin in association with cellulose microfibrils forms a complex, as found in carrot pomace, that is effective in modulating sugar absorption in the GI tract. This finding indicates that a diet including a sufficient amount of native forms of dietary fiber, specifically those retaining a naturally occurring complex of soluble and insoluble fiber such as found in suitably prepared fruit or vegetable pomace, can surprisingly restore glycemic control even in the presence of a high carbohydrate, diabetogenic diet. While it may be unsurprising that a whole food, plant-based diet is associated with normal glycemic control, it is surprising that the inclusion of relatively low amounts of a specific dietary fiber in a native configuration can counter the diabetogenic effects of a high carbohydrate diet and can maintain normal glycemic control to the extent that type 2 diabetes and related conditions are avoided, or their progression halted, or their pathophysiological effects averted.

EXAMPLES

Example 1. Effect of Carrot Fiber Diet on Incidence and Severity of Type 2 Diabetes Clinical trials have shown that different dietary fibers isolated from a variety of fruit and legume species are beneficial to varying degrees in decreasing plasma cholesterol while lowering blood glucose very modestly and improving other metabolic parameters. Both rodent and human studies have suggested a cholesterol-lowering effect of carrot fiber (17,18). Carrots also provide phytosterols and polyphenols (19), bioactive agents known to exert additional beneficial effects on plasma lipids and energy metabolism (20-22). In the present study, CPP was tested as a food ingredient for its ability to either prevent or mitigate type 2 diabetes in the Nile rat model. CPP was prepared by drying and milling carrot pomace residue obtained from juicing whole carrots. All studies and procedures were approved by the Brandeis IACUC for the ethical use of animals.

Calculations and Measurements

Food efficiency. Food efficiency was calculated by dividing body weight gain (in g) per day by caloric intake (daily food intake in kcal/day) and multiplying the result by 1,000. Results represent the grams of body weight gained per 1,000 kcal consumed. Thus, greater food efficiency represents greater weight gained per calorie.

Glycemic index. Dietary GI was calculated as defined in the literature (23-30), based on the respective sources of CHO in each diet (dextrose, cornstarch, and sucrose).

Glycemic Load. After obtaining the GI of the various dietary ingredients published in the literature (23-30), Glycemic Load was calculated for each diet using the CHO content in each ingredient with the following formula: Glycemic Load/kg of diet in Table 4=sum of net CHO in each ingredient x the GI of that CHO. Amounts were converted to Glycemic Load per 2,000 kcal to approximate the human equivalent.

Blood glucose. Blood glucose was measured in 50/50 $O_2/CO_2$ anesthetized rats from a drop of tail blood, obtained by lancet puncture of the lateral tail vein using a Bayer Contour glucometer (Bayer Co., Elhart, IN). Random blood glucose was assessed in nonfasted rats at 9-10 a.m. on non-feeding days (semipurified diets provided 3x/week). The rationale for using this parameter for diabetes assessment has been presented previously (5). Fasting blood glucose was measured at 9-10 a.m. after 16 h overnight food deprivation.

Oral Glucose Tolerance Test (OGTT). Rats were fasted for 16 h overnight. After assessment of body weight and fasting blood glucose, they were dosed with 1.75 g/kg BW of dextrose solution (10.5 g in 6 ml distilled water) by means of oral gavage, and blood glucose was typically assessed at 30 min after gavage. Diabetic status determined by OGTT was determined by any one or more blood glucose measurements made between 15 min and 2 hr following dextrose administration, e.g., at 30 min. Alternatively, OGTT status may be determined by the area under the curve (AUC) for multiple measurements over the 2 hr period.

Plasma triglycerides and total cholesterol. Plasma triglyceride (TG) and total cholesterol (TC) are determined spectrophotometrically using Infinity™ kits (Thermo Fisher Scientific Inc., Middletown, VA, TG ref #TR22421, TC ref #TR13421).

Insulin Enzyme-Linked Immunosorbent Assay for insulin (ELISA). Plasma insulin was determined with an enzyme-linked immunosorbent assay (ELISA) kit for rat/mouse insulin (Linco Research, Millipore, Billerica, MA, cat. #EZRMI-13K), according to the manufacturers' protocol.

Fecal fat analysis. 1 gram of combined feces from rats fed each diet was ground to a powder and extracted with 10 mL hexane:isopropanol 3:2 v/v with 0.005% 2,6-di-tert-butyl-4-methyl phenol. 5 mL of extract was collected into a preweighed vial and dried under $N_2$. The vial with extracted fat was weighed again for fat content. The residual feces were then extracted the same process a second time to ensure complete fat recovery.

Statistical analysis. Statistical analysis was performed using SPSS version 22.0 (SPSS, Inc., Chicago, IL). Student's t-test (p<0.05) was conducted where appropriate to the study design.

Experimental Protocol and Results

In Experiment 1 (NR Study 122), a total of 72 male wild-type Nile rats (5 diets×18 rats/group) from the Brandeis University breeding colony were fed four special diets incorporating three different fibers at a level of 10% by weight. Control Diet 133 provided (as a percent of energy) carbohydrate, fat and protein in a ratio of 60:20:20. Diet 133 is a standard high carbohydrate diabetes-inducing (i.e., diabetogenic) diet without any fiber added. Three different fibers were compared by adding 10% (w/w) of each fiber to Diet 133. The three test diets were Diet 151 with 10% cellulose, an insoluble fiber, Diet 153 with 10% inulin, a soluble fiber (obtained from chicory root), and Diet 152 with 10% carrot fiber (CPP milled to a 60 mesh particle size). The carrot fiber contained nearly equal amounts of insoluble cellulose fiber and soluble pectin fiber. The three test diets controlled nutritional parameters such as macronutrient composition (% energy from carbohydrate:fat:protein), caloric density (kcal/g), fiber content, and glycemic load. Diet descriptions and details of formulation are provided in Table 3.

In Experiment 2 (NR Study 130), the same 4 diets were again fed to 40 male wild type Nile rats (n=10). Two additional diets (20 more rats) based on Diet 133 were fed, one containing 10% by wt of CPP milled to 120-mesh, while the second diet contained a carrot pomace in which the soluble fiber component was removed, commercially sold as Hydrobind™. Ten male rats per group were fed these 6 diets for a total of 60 rats in Experiment 2. In addition to measuring of blood glucose for 10 wks as described for Experiment 1, the rats in the second experiment were necropsied and various organ weights and terminal plasma lipids were used to further document the degree of diabetes. Combining results for the first 4 diets in the two experiments (Studies 122+130) generated an n=28 per diet group (Table 4).

In both experiments, metabolic effects were assessed by measurements of random blood glucose (RBG), fasting blood glucose (FBG), and an oral glucose tolerance test (OGTT, at 0 and 30 min following an overnight fast). Nile rats with a starting age of 3 weeks (weanling rats) were evaluated after 6 weeks and 10 weeks. All experiments and procedures were approved by the Brandeis University Institutional Animal Care and Use Committee (IACUC). The combined results of Experiments 1 and 2 for food intake, growth, and blood glucose are shown in Table 4, and the results of Experiment 2 alone with added necropsy data are shown in Table 5.

The results in Table 4 emphasize the RBG value of 75 mg/l, which was selected to best denote the incidence of diabetes among the 28 Nile rats in each group as either resistant or susceptible to diabetes when below or above 75 mg/dl, respectively. When followed over time, the RBG is the most reliable predictor of the terminal degree of type 2 diabetes (T2DM) observed at necropsy in relatively short studies such as these. RBG is a reliable measure of the average daily exposure of tissues to chronically elevated circulating blood glucose beyond the fasting condition. In over 500 male Nile rats to date, this test described the strongest blood glucose relationship to tissue damage induced during several weeks of diet challenge, i.e. it represents what the tissues have experienced from being exposed to blood glucose above 75 mg/dl for several weeks to months. Furthermore, in all rats studied to date those having normal tissues at necropsy have revealed RBG<75 mg/dl. Above that value tissue damage becomes progressively worse, with pathologies increasing rapidly above 100 mg/dl. Thus, this cutoff point in RBG was the preferred value of 3 blood glucose measures used to establish the percent incidence of diabetes in each group (Table 4). A second more sensitive index of early diabetes was the 30 min OGTT test with cutoff at <150 mg/dl. This test was administered during the 10th week on the respective diets to determine whether or not the diabetic condition was only in an early stage. Finally, the overnight fasting glucose (FBG) was recorded as the 0 min time in the OGTT and provided the third, least sensitive index of diabetes. Although the last to rise, progressive increase in FBG above 60 mg/dl indicates that severe diabetes is present. This was supported at necropsy by enlarged (fatty) liver, swollen kidneys with nephritis, and severe wasting of fat depots accompanied by ketosis.

In combined data from Experiments 1 (NR Study 122) and 2 (NR Study 130) (combined results for growth, food intake, and blood glucose shown in Table 4) where the 4 diets were fed and the replicate data pooled, the first diet group with 0% fiber (high CHO control Diet 133) revealed 12/28 rats with RBG>75 mg/dl to yield a 43% incidence of diabetes susceptibility. On the other hand, 18/28 (64%) revealed 30 min OGTT>150 mg/dl to suggest early diabetes was affecting an additional 6 rats, but only 6/28 (21%) had elevated FBG>60 mg/dl. These comparative responses in blood glucose make the point that the FBG, while valuable as an end-stage index (when elevated diabetes is severe), it occurs too late in the sequence to be helpful in relatively short studies such as these. The OGTT is, by contrast, too sensitive and tedious to apply throughout a short study. Only the RBG is consistently predictive and easiest to apply on short notice. With 10% cellulose in the diet, the incidence of diabetes by all 3 blood glucose values was similar to the values noted in control rats, e.g. note that 43% also registered as diabetic by RBG, but 71% were in early diabetes by the 30 min OGTT. Only 14% were designated as diabetic by FBG. By contrast, with the 10% inulin diet, the incidence by RBG was reduced to 30%, while the 30 min OGTT revealed a 44% incidence of T2DM, with FBG dropping to 15% incidence. Finally, and quite surprisingly, with the 10% carrot fiber diet, the type 2 diabetes incidence based on RBG was 0/28 or 0%, but the more sensitive 30 min OGTT registered only 32% incidence, and the least sensitive FBG again being 0/28 for 0%. In other words, all of their RBG values from rats fed CPP were less than 75 mg/dl, suggesting that carrot pomace fiber prevented any end stage pathology associated with type 2 diabetes.

TABLE 3

Diet Composition (NR Studies 122, 130, and 131)

| | Diet | | | | | |
|---|---|---|---|---|---|---|
| | 133 | 151 | 153 | 152 | 152a | 152b |
| INGREDIENT | 0 fiber | 10% cellulose | 10% inulin | 10% carrot fiber | 10% carrot fiber 120 mesh | 10% Hydrobind ™ carrot fiber |
| CHO:Fat:Prot % E | 60:20:20 | 60:20:20 | 60:20:20 | 60:20:20 | 60:20:20 | 60:20:20 |
| (Fat/Prot % E ratio) | (1.0) | (1.0) | (1.0) | (1.0) | (1.0) | (1.0) |
| kcal/g | 4.2 | 3.8 | 3.8 | 3.7 | 3.7 | 3.8 |
| GL/2000 kcal | 224 | 200 | 200 | 208 | 208 | 201 |
| | | | g/Kg | | | |
| Casein | 106 | 96 | 96 | 87 | 87 | 95 |
| Lactalbumin | 106 | 96 | 96 | 87 | 87 | 95 |
| Dextrose | 186 | 167 | 167 | 144 | 144 | 166 |
| Sucrose | 186 | 167 | 167 | 144 | 144 | 166 |
| Cornstarch | 200 (+60 gel) | 174 (+60 gel) | 174 (+60 gel) | 145 (+60 gel) | 145 (+60 gel) | 169 (+60 gel) |
| Cellulose | 0 | 100 | 0 | 0 | 0 | 0 |
| Carrot powder (pomace**, 60 mesh) | 0 | 0 | 0 | 200 | 0 | 0 |
| Carrot powder (pomace**, 120 mesh) | 0 | 0 | 0 | 0 | 200 | 0 |
| Inulin | 0 | 0 | 100 | 0 | 0 | 0 |
| Hydrobind ™ (insoluble carrot fiber) | 0 | 0 | 0 | 0 | 0 | 110 |
| Fat: | | | | | | |
| Margarine B (80% fat) | 118 (94 fat) | 106 (85 fat) | 106 (85 fat) | 98 (78 fat) | 98 (78 fat) | 105 (84) |
| Mineral mix (Ausman - Hayes) | 46 | 41 | 41 | 41 | 41 | 41 |
| Vitamin mix (Hayes - Cathcart) | 12 | 11 | 11 | 11 | 11 | 11 |
| Choline chloride | 3 | 3 | 3 | 3 | 3 | 3 |
| Cholesterol | 0.6 | 0.6 | 0.6 | 0.6 | 0.6 | 0.6 |

* 60 g cornstarch added to 800 mL(diet 133, 151 and 153) and 1200 ml (diet 152 and 152a) water to form gel
**Pomace composition per 200 g (58 g net CHO, 98 g fiber, 14 g PRO, 4 g FAT)

TABLE 4

Diabetic assessment of 3 week old male Nile rats fed high CHO diets with 0% or 10% of three fiber types for 10 weeks (NR Studies 122 + 130, pooled replicates)

| | Diet | | | |
|---|---|---|---|---|
| | 133<br>0% Fiber | 151<br>10% cellulose<br>(insoluble fiber) | 153<br>10% inulin<br>(soluble fiber) | 152<br>10% carrot fiber<br>(insoluble/soluble) |
| CHO:Fat:Protein (% en) | 60:20:20 | 60:20:20 | 60:20:20 | 60:20:20 |
| Kcal/g | 4.2<br>(n = 28) | 3.8<br>(n = 28) | 3.8<br>(n = 27) | 3.7<br>(n = 28) |
| FBG T2DM (% incidence)* | 22/6 (21%) | 24/4 (14%) | 23/4 (15%) | 28/0 (0%) |
| OGTT T2DM (% incidence)** | 10/18 (64%) | 8/20 (71%) | 15/12 (44%) | 19/9 (32%) |
| RBG T2DM (% incidence)*** | 16/12 (43%) | 16/12 (43%) | 19/8 (30%) | 28/0 (0%) |
| OR (95% CI)**** | 1.00 | (0.54, 1.83) | (0.34, 1.44) | (0.01, 0.04) $p < 0.05$ |
| ave % incidence<br>(FBG, OGTT-30 min, RBG) | 43% | 43% | 30% | 11% |
| Body weight (g) | | | | |
| Initial (3 wks of age) | 31 ± 5 | 30 ± 5 | 29 ± 6 | 31 ± 6 |
| After 6 wks | 83 ± 8$^a$ | 87 ± 10$^{bc}$ | 79 ± 10$^c$ | 75 ± 9$^{ab}$ |
| After 10 wks | 94 ± 11$^a$ | 99 ± 11$^b$ | 94 ± 14$^c$ | 86 ± 11$^{abc}$ |
| Body weight gain per day (g/d) | 0.81 ± 0.16$^{ab}$ | 0.90 ± 0.15$^{ac}$ | 0.84 ± 0.17$^d$ | 0.69 ± 0.12$^{bcd}$ |
| Food intake | | | | |
| g/d | 9.0 ± 1.8 | 9.6 ± 1.2$^a$ | 8.8 ± 1.2$^a$ | 9.4 ± 1.7 |
| kcal/d | 38 ± 8$^{ab}$ | 37 ± 5$^c$ | 33 ± 5$^{ac}$ | 35 ± 6$^b$ |
| Food efficiency<br>(g BW gained/1000 kcal) | 22 ± 5$^{ab}$ | 25 ± 3$^{ac}$ | 25 ± 5$^{bd}$ | 20 ± 4$^{cd}$ |
| Random blood glucose (mg/dl) | | | | |
| After 6 wks | 170 ± 192$^{abc}$ | 88 ± 64$^{ad}$ | 60 ± 11$^c$ | 66 ± 12$^{bd}$ |
| After 10 wks | 202 ± 225$^{abc}$ | 130 ± 132$^{ad}$ | 67 ± 24$^c$ | 56 ± 7$^{bd}$ |
| OGTT (BG mg/dl)<br>After 10 wks | | | | |
| Fasting blood glucose, 0 min | 57 ± 40$^a$ | 50 ± 18 | 46 ± 14 | 44 ± 8$^a$ |
| 30 min | 236 ± 164$^{ab}$ | 222 ± 105$^{cd}$ | 163 ± 77$^{bd}$ | 135 ± 57$^{ac}$ |

Values are mean ± SD (n = 28-27)
$^{a,b,c}$Means in a row sharing a common superscript differ (p < 0.05) by one-way ANOVA and Fisher's PLSD.
*% Incidence based on FBG <60 mg/dl> after 10 wk on diet.
**% Incidence based on OGTT 30' <150 mg/dl> after 10 wk on diet.
***% Incidence based on RBG <75 mg/dl> after 10 wk on diet.
****Odds Ratio statistic using % incidence based on RBG <75 mg/dl> after 10 wk on diet. Only 10% Carrot fiber fiber differs from 0% Fiber

TABLE 5

Diabetic assessment of 3 week old male Nile rats fed high CHO diets with 0% or 10% of five fiber types for 10 weeks (NR Study 130)

| | Diet | | | | | |
|---|---|---|---|---|---|---|
| | 133 | 151 | 153 | 152 | 152A | 152B |
| INGREDIENT | 0% fiber | 10%<br>cellulose | 10%<br>inulin | 10% carrot<br>fiber,<br>60 mesh | 10% carrot<br>fiber,<br>120 mesh | 10%<br>Hydrobind |
| CHO:Fat:Prot % E | 60:20:20 | 60:20:20 | 60:20:20 | 60:20:20 | 60:20:20 | 60:20:20 |
| (Fat/Prot % E ratio) | (1.0) | (1.0) | (1.0) | (1.0) | (1.0) | (1.0) |
| kcal/g | 4.2 | 3.8 | 3.8 | 3.7 | 3.7 | 3.8 |
| GL/2000 kcal | 224 | 200 | 200 | 208 | 208 | 201 |
| | n = 10 | n = 10 | n = 9 | n = 10 | n = 10 | n = 9 |
| FBG <60> T2DM<br>(% incidence) | 7/3 (30%) | 8/2 (20%) | 7/2 (22%) | 10/0 (0%) | 9/1 (10%) | 7/2 (22%) |
| OGTT <150> T2DM<br>(% incidence) | 4/6 (60%) | 3/7 (70%) | 5/4 (44%) | 5/5 (50%) | 6/4 (40%) | 3/6 (67%) |
| RBG <75> T2DM<br>(% incidence) | 5/5 (50%) | 5/5 (50%) | 5/4 (44%) | 10/0 (0%) | 8/2 (20%) | 6/3 (33%) |

TABLE 5-continued

Diabetic assessment of 3 week old male Nile rats fed high CHO diets
with 0% or 10% of five fiber types for 10 weeks (NR Study 130)

| | Diet | | | | | |
|---|---|---|---|---|---|---|
| | 133 | 151 | 153 | 152 | 152A | 152B |
| | INGREDIENT | | | | | |
| | 0% fiber | 10% cellulose | 10% inulin | 10% carrot fiber, 60 mesh | 10% carrot fiber, 120 mesh | 10% Hydrobind |
| OR (95% CI) | 1.00 | 1.00 (0.42, 2.40) | 0.88 (0.38, 2.02) | 0.00 (0.01, 0.03) $p < 0.05$ | 0.40 (0.10, 1.60) | 0.66 (0.22, 2.00) |
| Average % incidence | 47% | 47% | 37% | 17% | 23% | 41% |
| Body weight (g) | | | | | | |
| Initial (3 wk of age) | 31 ± 6 | 31 ± 6 | 31 ± 6 | 31 ± 5 | 31 ± 5 | 31 ± 5 |
| After 6 wks | 82 ± 8$^a$ | 84 ± 12$^b$ | 82 ± 7$^c$ | 74 ± 8$^{abcd}$ | 81 ± 6 | 84 ± 9$^d$ |
| After 10 wks | 91 ± 9 | 98 ± 12$^a$ | 96 ± 11 | 86 ± 10$^{ab}$ | 93 ± 8 | 97 + 15$^b$ |
| Body weight gain per day (g/d) | 0.74 ± 0.12 | 0.82 ± 0.12 | 0.81 ± 0.18 | 0.69 ± 0.15 | 0.76 ± 0.13 | 0.81 ± 0.21 |
| Food intake | | | | | | |
| g/d | 8.9 ± 2.6$^a$ | 8.5 ± 1.1 | 7.5 ± 0.5$^{ac}$ | 7.7 ± 0.4$^b$ | 8.5 ± 0.8 | 9.1 ± 1.8$^{bc}$ |
| kcal/d | 38 ± 11$^{abcd}$ | 32 ± 4$^a$ | 29 ± 2$^{cf}$ | 29 ± 2$^{be}$ | 32 ± 3$^d$ | 34 ± 7$^{ef}$ |
| Food efficiency (g BW gain/1000 kcal) | 21 ± 6$^{ab}$ | 26 ± 3$^a$ | 28 ± 5$^b$ | 24 ± 5 | 24 ± 4 | 24 ± 7 |
| Random blood glucose (mg/dl) | | | | | | |
| After 6 wks | 253 ± 222$^{abcd}$ | 104 ± 100$^a$ | 62 + 14$^b$ | 60 ± 13$^c$ | 111 ± 143$^d$ | 159 ± 179 |
| After 10 wks | 306 + 271$^{abc}$ | 204 ± 192 | 68 ± 13$^a$ | 54 ± 10$^b$ | 134 ± 176$^c$ | 181 ± 234 |
| OGTT (BG mg/dl) After 6 wks | | | | | | |
| Fasting blood glucose, 0 min | 52 ± 18 | 57 ± 15 | 51 ± 15 | 49 ± 18 | 61 ± 20 | 60 ± 23 |
| 30 min | 253 ± 151$^a$ | 214 + 116 | 150 ± 57 | 130 + 59$^{ab}$ | 206 ± 124 | 252 ± 145$^b$ |
| After 10 wks | | | | | | |
| Fasting blood glucose, 0 min | 58 ± 23 | 48 ± 19$^a$ | 50 ± 18$^c$ | 45 ± 8$^b$ | 44 ± 12$^d$ | 81 ± 71$^{abcd}$ |
| 30 min | 279 ± 196 | 249 ± 134 | 151 ± 37 | 145 ± 64 | 230 ± 178 | 267 ± 196 |
| Organ weight (% BW) | | | | | | |
| Liver | 5.28 ± 1.3$^{abcde}$ | 3.84 ± 0.7$^a$ | 3.21 ± 0.3$^c$ | 3.18 ± 0.2$^b$ | 3.61 ± 0.8$^d$ | 3.99 ± 1.5$^e$ |
| Kidney | 1.57 ± 2.0$^{abcd}$ | 0.77 ± 0.1$^a$ | 0.64 ± 0.1$^c$ | 0.66 ± 0.1$^b$ | 0.71 ± 0.1$^d$ | 0.79 ± 0.3 |
| Cecum | 1.65 ± 1.0$^{abc}$ | 1.27 ± 0.3$^{defg}$ | 2.25 ± 0.6$^{be}$ | 2.42 ± 0.3$^{ad}$ | 2.40 ± 0.3$^{cf}$ | 2.08 ± 0.9$^g$ |
| Adipose | | | | | | |
| Epididymal | 2.45 ± 1.1$^a$ | 3.33 ± 0.5$^a$ | 2.83 ± 0.7 | 2.67 ± 0.5 | 2.92 ± 0.7 | 2.76 ± 1.1 |
| Perirenal | 0.91 ± 0.5$^{ab}$ | 1.38 ± 0.5$^a$ | 1.30 ± 0.3 | 1.01 ± 0.5$^c$ | 1.04 ± 0.5$^d$ | 1.54 ± 0.5$^{bcd}$ |
| Brown fat | 1.44 ± 0.6$^a$ | 1.80 ± 0.6 | 1.94 ± 0.5 | 1.45 ± 0.5$^b$ | 1.57 ± 0.5 | 2.00 ± 0.7$^{ab}$ |
| Total fat | 4.82 ± 2.1$^{ab}$ | 6.52 ± 1.1$^a$ | 6.07 ± 1.3 | 5.14 ± 1.2 | 5.52 ± 1.4 | 6.30 ± 2.0$^b$ |
| Carcass | 72 ± 2$^a$ | 73 ± 2 | 74 ± 2$^c$ | 74 ± 2$^{ab}$ | 73 ± 1 | 71 ± 2$^{bc}$ |
| Body length (cm) | 13.6 ± 0.8 | 13.8 ± 0.5 | 13.9 ± 0.7 | 13.5 ± 0.5 | 13.5 ± 0.7 | 13.5 ± 0.9 |
| Plasma | | | | | | |
| TC (mg/dl) | 232 ± 189$^{abcd}$ | 127 ± 42$^a$ | 134 + 26$^b$ | 116 ± 18$^c$ | 140 ± 45$^d$ | 156 ± 53 (n = 8) |
| TG (mg/dl) | 132 ± 180$^{abcd}$ | 76 ± 24$^a$ | 54 ± 17$^b$ | 52 ± 21$^c$ | 50 ± 21$^d$ | 58 ± 19 (n = 8) |

Values are mean ± SD (n = 9-10)
$^{a,b,c}$Means in a row sharing a common superscript differ ($p < 0.05$) by one-way ANOVA and Fisher's PLSD test
* Odds Ratio statistic using % incidence based on RBG <75 mg/dl> after 10 wk on diet.
Only 10% Carrot fiber-60 mesh differs from 0% fiber.

Example 2. Effect of Carrot Fiber Diet on Body Weight Gain

Together with the beneficial reduction in blood glucose levels (best measured by RBG and to a lesser extent as 30 min-OGTT—see Table 4) when animals were fed diets high in carbohydrate accompanied by carrot fiber in the form of CPP-60 mesh, another remarkable finding evident in Table 4 is a statistically significant reduction in body weight gain (measured in g/d) by CPP rats compared to the same diet lacking fiber (or containing alternative fibers of either cellulose or inulin). This was due in part to the fact that the diabetic subgroups in other diets (i.e., non-CPP diets) gained the most weight to increase group averages (data not shown). Remarkably, food consumption as measured both by mass (g/d) and by energy intake (kcal/d) remained relatively constant among the four diet groups, except for extra calories consumed by the 0% fiber group as they developed the most diabetes. However, animals consuming the carrot fiber diet maintained an average of 11% lower (8%-12% range) body weight than the other groups and their rate of body weight gain (g/d) over the 10 week interval was only 0.69 g/d versus an average of 0.85 g/d for the other groups, or approximately a 20% lower rate of weight gain, even though their energy consumption in kcal/day remained about the same as that of the other groups. Note that the food efficiency data showed this parameter to be lowest for the CPP-fed group, i.e., calories consumed failed to appear as weight gain, most likely disappearing as fermentation by gut flora. In addition, the growth data from Experiment 2 (Table 5) revealed that all groups maintained similar linear growth (body length) and carcass weight (organs removed). Therefore, carrot fiber addition to the mammalian diet may be helpful in maintaining a healthy, but lower body weight and/or reducing excessive weight gain when a mammal consumes a diet that is rich in carbohydrates. The low total fat pool of the control rats (Diet 133) was due entirely to the diabetic subgroup with the most advanced diabetes, showing the effect of chronic ketosis on accelerated fat burn in that subgroup (data not shown). In the diets described in Table 3 and operative in Tables 4 and 5, 60% of the dietary energy was provided by carbohydrates.

Example 3. Effect of Pectin-Free Carrot Fiber Diet on Type 2 Diabetes

Male Nile rats were fed a diet similar to Diet 152 (Study 130, Diet 152a and 152b), but containing 10% CPP-120 mesh or Hydrobind™ instead of 10% carrot pomace powder-60 mesh (CPP). See Table 1 for a comparison of the CPP-120 mesh and Hydrobind™ with CPP 60 mesh carrot pomace composition. Hydrobind™ has a much lower ratio of soluble to insoluble fiber than CPP-60 while CPP-120 is ground twice as fine as CPP-60. Additional groups of rats were fed the CPP-60 mesh as Diet 152 and control (diabetogenic) Diet 133, as well as the original 10% cellulose fiber (Diet 151) and 10% inulin fiber (Diet 153). The original 4 diets were repeated for a second 10 wks in order to gain tissue results at necropsy, not captured by the initial Study 122 design.

The results shown in Table 5 reveal that control (0% fiber), 10% cellulose, 10% inulin, and Hydrobind™ groups showed about 40-50% incidence of type 2 diabetes based on the combined glucose measures, while the 60 mesh CPP showed the lowest incidence of type 2 diabetes, particularly in reference to RBG>75 mg/dl (0/10) and FBG (0/10), but also showing only a 17% incidence of type 2 diabetes based on all three blood glucose tests averaged. The 120 mesh CPP diet provided intermediate results. After 10 weeks, the CPP 60 mesh diet showed the lowest weight gain, which was significantly lower than the 10% cellulose 10% Hydrobind diets, with CPP-120 again providing intermediate results; the body weight gain/day reflects a similar trend. Similarly, the energy (kcal) intake was lowest for CPP-60 and Inulin. These results suggest that one role of soluble fiber is to enhance gut flora fermentation, which plays a role in preventing type 2 diabetes.

Necropsy data showed that liver and kidneys were enlarged with advanced diabetes (control diet) and were the smallest with CPP-60, with slight liver increases (due to fatty liver development) in the 10% cellulose, CPP-120, and Hydrobind™ groups. The protective effect of an enlarged cecum against type 2 diabetes also reflects the fermentation of ingested soluble fiber by the large bowel gut flora (especially CPP-60+CPP-120 mesh and to a lesser extent inulin), but not insoluble, non-fermentable fiber (10% cellulose). The latter surprisingly had the smallest cecum, even though those rats excreted 2× the volume of feces (Tables 5, 6). As the literature would suggest, the soluble fiber volume is presumably consumed when fermented by gut flora, producing the short chain fatty acids that, in turn, exert their protective role against diabetes (Arora and Backhed, 2016). Insoluble fiber does not work. In addition, terminal plasma lipids (total cholesterol and triglycerides) reflected the degree of type 2 diabetes at necropsy, including blood glucose values and tissue pathology.

The results thus point to an important role for the inclusion of a sufficient amount of soluble fiber together with insoluble fiber and ground to correct mesh size (CPP-60) in order to maintain healthy blood glucose concentration. Without intending to limit the invention to any particular theory or mechanism, it appears that soluble fiber in naturally occurring complexes of soluble fiber and insoluble fiber play an important role in maintaining naturally occurring fiber structure (e.g., by forming a sheath of soluble fiber around insoluble fiber, resulting in a tertiary and/or quaternary structure), and that removal of soluble fiber, e.g., by pectinase treatment (Hydrobind™) or excessive use of heat or grinding (which produces heat in generating a smaller mesh size, CP-120), denatures the fiber structure with consequent loss of function in terms of preventing type 2 diabetes.

Example 4. Fecal Fat Analysis

Feces were collected from individual rat cages set aside for 24 h during the last week of Study 130. All pellets were gathered from each cage, weighed 'wet', then air dried in a forced hot-air drying apparatus. The dried pellets were then weighed and the results are reported as the 24 h dried fecal output for each rat and averaged for each diet group (see Table 6).

The most dramatic difference among the groups was the 10% cellulose group, which excreted 2-3 times the fecal volume of all other groups; the other groups were all similar, with inulin, CPP-60, and Hydrobind™ groups excreting the least. Adjusting the data according to dry food intake (%) (i.e., indirectly adjusting for calorie intake) revealed that the cellulose group excreted twice the percentage recorded for the rest, but the CPP-60 group was lowest, being about 20% lower than the 10% inulin group. Although the fecal volume was much greater in the 10% cellulose group, the fecal fat content of that group was about half that of other diets. Thus, the measured total fecal fat (in mg/d) appeared about the same across groups and unrelated to dietary fiber type. The data do not support the concept that carrot fiber lowers blood lipids and reduces weight gain by binding and excreting fat from the intestine. In addition, adjusting the data to the percent fat excreted per g fat consumed, all groups appeared even more comparable to each other, i.e., they showed that 1.4% to 1.8% of daily fat consumed ended up in feces across the groups. Thus, for all diets more than 98% of the triglycerides consumed each day was absorbed, similar to normal human fat absorption. In summary, no evidence was found for fat malabsorption as the explanation for carrot fiber function, in contrast to claims by others (see published patent application US2014/0127297) who studied different forms of diet fiber, including carrot pomace.

TABLE 6

Fecal weight and fecal fat for 3 week old male Nile rats fed high CHO
diets with 0% or 10% various fiber types for 10 weeks (NR Study 130)

| | Diet | | | | | |
|---|---|---|---|---|---|---|
| | 133 | 151 | 153 | 152 | 152A | 152B |
| | | | INGREDIENT | | | |
| | 0 fiber | 10% cellulose | 10% inulin | 10% carrot fiber, 60 mesh | 10% carrot fiber, 120 mesh | 10% hydrobind |
| CHO:Fat:Prot % E | 60:20:20 | 60:20:20 | 60:20:20 | 60:20:20 | 60:20:20 | 60:20:20 |
| (Fat/Prot % E ratio) | (1.0) | (1.0) | (1.0) | (1.0) | (1.0) | (1.0) |
| kcal/g | 4.2 | 3.8 | 3.8 | 3.7 | 3.7 | 3.8 |
| GL/2000 kcal | 224 | 200 | 200 | 208 | 208 | 201 |
| Fecal output | | | | | | |
| dry wt (g/day) | $0.61 \pm 41^a$ | $1.15 \pm 0.38^{abcde}$ | $0.40 \pm 0.10^b$ | $0.50 \pm 0.15^c$ | $0.63 \pm 0.18^d$ | $0.52 \pm 0.26^e$ |
| dry feces/g food intake (%) | $6.6 \pm 4.0^a$ | $13.5 \pm 3.3^{abcde}$ | $6.5 \pm 1.7^b$ | $5.4 \pm 1.3^c$ | $7.4 \pm 2.0^d$ | $5.6 \pm 2.1^e$ |
| fecal fat (mg/g dry feces/day) | 24 ± 2 | 10 ± 2 | 20 ± 6 | 23 ± 4 | 18 ± 6 | 22 ± 0 |
| total fecal fat (mg/day) | 15 ± 1 | 12 ± 2 | 8 + 2 | 12 ± 2 | 11 ± 4 | 11 ± 0 |
| % total fecal fat/fat intake | 1.8 ± 0.2 | 1.7 ± 0.3 | 1.4 ± 0.4 | 1.8 ± 0.3 | 1.7 ± 0.5 | 1.5 ± 0.0 |

Values are mean ± SD (n = 9-10; fecal fat n = 2 based on combined fecal samples)
$^{a,b,c}$Means in a row sharing a common superscript differ (p < 0.05) by by one-way ANOVA and Fisher's PLSD test

Example 5. Effect of Carrot Fiber Diet on Progression of Type 2 Diabetes

CPP was again tested as a food ingredient for its ability to either prevent the progression or mitigate the effects of type 2 diabetes in progress, but only after the Nile rat had reached an adult age of 6 mo. After the previous 10 week studies had been completed (Studies 122 and 130, Table 4), 15 of the prediabetic Nile rats were placed on a standard rat chow diet until 24 wks old to further their diabetes. The diabetic status was then defined by applying the Nile rat blood glucose level criteria: RBG>75 mg/dl and 30 min-OGTT>150 mg/dl, i.e. where blood glucose was measured 30 minutes after glucose administration. This coupling of RBG and OGTT measurements is especially diagnostic for the diabetic condition in the Nile rat. After reaching a more advanced adult age of 23-24 wks, the animals were then assigned equally to two groups (Diets 133 and 152, Table 3). Fasting body weights and RBG and OGTT measurements were obtained, and no statistically significant differences were apparent between animals in the two groups (see Table 8 "Initial" values). Then, the dietary regimens were imposed for a 4 week interval in which 8 animals were fed the previous high CHO diabetes-inducing diet (Diet 133 without any fiber as in Study 122) while seven animals were fed Diet 152 (high CHO diabetes-inducing diet with 10% carrot fiber added (also fed in Study 122). After the 4 week dietary interval, RBG and OGTT measurements were again made and the animals were sacrificed. Body measurements, organ and tissue weights and plasma lipids and cholesterol were all determined (see Table 7).

While some parameters remained constant after 4 weeks, many significant differences emerged during this short dietary intervention in which some of the animals consumed a high CHO diet while others consumed the same high CHO diet supplemented with 10% carrot fiber. More specifically, fasting body weights did not differ between groups while food intake (kcal/d) measurably decreased for the fiber group. Fiber functions to dilute a high calorie food and helps promote satiety rather than hunger, especially if the fiber is soluble and fermented in the large bowel to generate short chain fatty acids that suppress appetite. As evident in Table 7, RBG levels approximately doubled for the high CHO control diet while remarkably remaining unchanged for the carrot fiber group. Similarly the 4 week OGTT blood glucose values measured 30 minutes after glucose administration for the high CHO diet almost doubled (to 356 mg/dl from 209 mg/dl) while remaining essentially unchanged for the fiber group (223 vs. 209 mg/dl). Differences in body organ weight as a percentage of body weight were consistent with progressive type 2 diabetes for the animals in the high CHO group while livers from the carrot fiber group animals were significantly smaller and healthier. Accordingly, increased liver and kidney size which are diagnostic for diabetes were greater for the high CHO control group compared to the carrot fiber group. In addition, with advanced disease and ketosis induction, the amount of adipose tissue around visceral organs generally diminishes, and this was found to be the case with the high CHO control group. Thus, the % total body fat measured 5.5 g for the high CHO control group and 7.2 g for the carrot fiber group. It was remarkable how short a time interval (4 weeks) was required for prediabetic adult Nile rats to suffer adverse physiological consequences consistent with advanced type 2 diabetes when consuming a high carbohydrate diet lacking dietary CPP fiber. Finally, plasma total cholesterol values (TC) were consistently and statistically lower for the carrot fiber group than for the control group (142 mg/dl vs. 207 mg/dl).

TABLE 7

Body weights, random and fasting blood glucose of adult male Nile rats fed high CHO diets without (control), or with 10% carrot fiber for 4 wks (NR St. 131)

| | Diet | |
|---|---|---|
| | 133 Control | 152 10% carrot fiber |
| | CHO:Fat:Protein (% en) | |
| | 60:20:20 | 60:20:20 |
| | Kcal/g | |
| | 4.2 (n = 8) | 3.7 (n = 7) |
| OGTT 30 min <150> 4 wk T2DM (%) | 0/8 (100%) | 0/7 (100%) |
| RBG <75> 4 wk T2DM (%) | 1/7 (88%) | 2/5 (71%) |
| FBG <60> 4 wk T2DM (%) | 5/3 (38%) | 6/1 (14%) |
| Starting age (wks) | 23 ± 3 | 24 ± 3 |
| Fasting Body weight (g) | | |
| Initial | 116 ± 9 | 115 ± 9 |
| After 4 wks | 114 ± 5 | 119 ± 8 |
| Food intake (4 wk avg.) | | |
| g/d (dry) | 8.8 ± 1.3 | 7.8 ± 1.0 |
| kcal/d | 37 ± 5 | 29 ± 4* |
| Random blood glucose (mg/dl) | | |
| Initial | 184 ± 120$^a$ | 213 ± 143 |
| After 4 wks | 379 ± 168$^a$ | 196 ± 119 |
| OGTT (BG mg/dl) | | |
| Initial | | |
| Fasting blood glucose, 0 min | 64 ± 20$^b$ | 61 ± 25 |
| 30 min | 209 ± 68$^b$ | 209 ± 60 |
| After 4 wks | | |
| Fasting blood glucose, 0 min | 70 ± 52$^c$ | 49 ± 11 |
| 30 min | 356 ± 127$^c$ | 223 ± 43* |
| Organ weight (% BW) | | |
| Liver | 4.55 ± 0.89 | 3.99 ± 0.79 |
| Kidney | 0.94 ± 0.21 | 0.71 ± 0.09* |
| Cecum | 1.66 ± 0.48 | 2.08 ± 0.37 |
| Adipose | | |
| Epididymal | 2.79 ± 1.03 | 2.93 ± 0.56 |
| Perirenal | 1.10 ± 0.74 | 1.89 ± 0.48* |
| Brown fat | 1.61 ± 0.70 | 2.36 ± 0.59* |
| Total fat | 5.50 ± 2.31 | 7.19 ± 0.74 |
| Carcass | 70 ± 2 | 69 ± 2 |
| Body length (cm) | 14.5 ± 0.6 | 14.7 ± 0.5 |
| Plasma lipids, terminal (mg/dL) | | |
| TC | 207 ± 49 | 142 ± 25* |
| TG | 75 ± 20 | 58 ± 21 |

Values are mean ± SD (n = 7-8)
*Significantly different (P < 0.05) than control
$^{a,b}$Means in the column sharing common superscripts are significantly different (P < 0.05) by paired t-test Example 6. Effects of Dietary Plant Fiber on Development of Diabetes Results from comparative studies revealed the effect of dietary fiber on metabolic health, specifically related to developing chronic disease in the form of type 2 diabetes mellitus (T2DM). First, carrot pomace powder (CPP) consistently outperformed all other fiber types tested. Identical diet designs in the first two experiments (Studies 122 & 130) allowed pooling of a total of 112 male Nile rats (*Arvicanthis niloticus*) from 4 basic diet groups (n=28 per group) that set the stage for all subsequent studies: Diet 133 (60:20:20 as % calories as CHO:Fat:PROT) was the Control diabetogenic diet with 0% fiber; Diet 133+10% cellulose (insoluble fiber); Diet 133+10% inulin (soluble fiber); and Diet 133+10% CPP (50-50% soluble fiber-insoluble fiber). See Table 3 for description of diets.

When all 3 blood glucose values are considered, the 30 min OGTT (oral glucose tolerance test) glucose value was most sensitive across all diet groups, revealing the highest % incidence of T2DM based on >150 mg/dl glucose as the cutoff for defining diabetes in the Nile rat. The RBG (random blood glucose) value was next most sensitive with >75 mg/dl as the cutoff; and FBG (fasting blood glucose) value was a poor third with FBG>60 mg/dl as the cutoff, 'poor' because the latter typically did not predict the dietary impact on diabetes observed at necropsy after 10 wks on diet. In essence, FBG rises too late in the diabetes progression to provide advanced warning of imminent disease, but indicates severe diabetes when it is elevated. For example, note how the FBG was only useful diagnostically in control (0% fiber) Nile rats susceptible to diabetes, being slightly elevated in that subgroup relative to the resistant subgroup, and with weak associations in other diet groups containing fiber because the fiber was protective to varying degrees. See Table 8. All things considered, the OGTT value was most reliable, but the technique is somewhat cumbersome and labor intensive. On the other hand, the RBG value generated from a single drop of tail blood was slightly less sensitive, but just as valuable for predicting endpoint diabetes at necropsy. Thus, the most practical index was RBG with >75 mg/dl as the cutoff index; not overly sensitive like the 30 min OGTT value, but much more sensitive than FBG for predicting actual diabetes at necropsy. With this model one can use the RBG as a proxy at any time during the dietary challenge to assess the effect of a given diet modification on diabetes progression (the current "resistant" or "susceptible" diabetes status of rats, i.e., whether or not diabetes has started (susceptible rat) and how aggressively it is progressing (i.e., how elevated is RGB?) as a function of a dietary intervention such as a specific fiber.

Fibers that were associated with slower weight gain with or without reduced caloric intake (growth rate as gain/day) produced the least diabetes. This was complicated somewhat by advanced diabetes late in the challenge (last 3 weeks), which causes extreme hyperphagia coupled with terminal weight loss when body fat is consumed during ketosis (e.g., compare susceptible versus resistant rats in 0% fiber group). Also note that citrus pectin in Study 132 clogged the digestive track and reduced caloric intake, resulting in less weight gain and less T2DM, but stunted growth detected as reduced body length (bone growth). By contrast, CPP reduced weight gain slightly without compromising body length. Greater body weight gain during diabetes development as a function of diet (10% cellulose, 10% inulin) was often linked to modest adipose tissue accumulation (Controls) compared to nondiabetic rats (CPP and pectin). SeeTables 8, 10, and 11.

Food efficiency. Weight gain per calorie consumed tended to be less with fibers that protect against T2DM, i.e., calories from some carbohydrates in certain fibers can be diverted to bacterial fermentation in the large bowel and produce short chain fatty acids, etc. Such fibers have been linked to reduced hunger, less food consumption, and lower adipose accumulation, as well as less diabetes (Arora and Backhed, 2016). Fermentable fibers also appear to reduce fecal volume and lower cecum pH See Tables 9 and 10. CPP (half-soluble and half-insoluble fiber) seemed the best in this regard. Inulin (soluble) and cellulose (insoluble) resulted in higher food efficiency (i.e. greater weight gain per calorie), which is a general finding during diabetes induction before it is reversed later on as weight loss during ketosis associated with more advanced diabetes.

In the expanded study (Table 10, unsplit; Table 11, split data), again only CPP (30-mesh) was totally protective (0% incidence of T2DM, based on the RBG<75 mg/dl) compared to the 60% diabetes incidence seen in the controls. None of the other fibers came close to the 0% T2DM incidence associated with CPP, including surprisingly citrus fiber (also half-soluble, half-insoluble fiber), citrus pectin (soluble), and Fibersol2 (soluble resistant starch).

Studies 130 and 132 also added at least two other dimensions. First, when Hydrobind fiber, a chemically modified derivative of carrot pomace (stripped of its pectin, rendering it a highly absorbent insoluble fiber), was tested it no longer protected against diabetes. This suggests the binary combination of soluble and insoluble fibers found in underivatized carrot pomace (60-mesh CPP) was important. Interestingly, finely milling CPP to generate a more readily dispersible 120-mesh CPP also caused CPP to lose effectiveness against diabetes, suggesting that excessive grinding can damage the effective structure found in the larger (30 and 60-mesh) CPP particles. Less effective also were citrus pectin (soluble fiber), Fibersol2 (digestion-resistant modified soluble starch fiber) and citrus fiber (Citri-Fi 100), a half soluble-half insoluble fiber derived from orange pulp [ADM Table 6]. Interestingly, while the dual soluble and insoluble components of natural CPP fiber may have major biological importance in diabetes deterrence, Citri-Fi is also a fiber with equal amounts of soluble and insoluble components that was less effective.

Necropsy confirmed earlier findings about T2DM in this species that diabetes-associated liver enlargement as fatty liver (nonalcoholic fatty liver disease, NAFLD) was increased in susceptible rats compared to the resistant rats (Table 10). The cecum was also enlarged in susceptible Control rats (in keeping with their more adverse gut flora profile), but was also enlarged in resistant rats fed CPP (expressing a preferred gut flora profile), suggesting that overgrowth of either "good" or "bad" flora can occur with an opposite impact on diabetes. Plasma total cholesterol and triglycerides were typically lower with the CPP diet, as well, enhancing the anti-metabolic syndrome nature of this fiber. The cecum in CPP-fed rats had the lowest pH, suggesting fermentation by their gut flora was generating beneficial short chain fatty acids relative to the susceptible Control rats.

Concurrent studies of hepatic mitochondria from Nile rats have revealed that the mitochondrial DNA mutational load increases with diabetes, or more likely vice versa, i.e. the diabetes begins when mtDNA is damaged by glucose overload and the stress of reactive oxygen species (ROS) on mitochondrial DNA point mutations causes respiratory dysfunction and reduced glucose utilization (data not shown). It appears that certain fibers can deter this mtDNA damage, presumably linked to their beneficial impact on gut flora.

Although the primary effect of fiber may be to protect against or delay T2DM induction in young Nile rats, the CPP was found to benefit adult male rats with moderately severe diabetes as well (Table 7). Fifteen 6 month old males with RBG of approximately 200 mg/dl were separated into 2 groups based on equal body weights (115 g) and identical 30 min OGTT values (209 mg/dl) with each Nile rat housed individually. The control group was fed the high carbohydrate Diet 133 (60:20:20 CHO:Fat:Protein), while the test diet had 10% 60-mesh CPP added. After 4 weeks the control group had started losing weight due to ketosis, while CPP Nile rats gained slightly despite the fact that the former group ate 27% more calories (p<0.05). The RBG increased 106% in controls (to 379±168 mg/dL), while the RBG in the CPP group remained unchanged (at 196±119 mg/dl). A similar response was seen in the 30 min OGTT in Controls (increasing 70%, but only 7% in the CPP group). At necropsy the percent fat was lower in Controls (ketosis with adipose loss) while adipose was normal in the CPP group. In addition, the kidneys were enlarged and total cholesterol was elevated by 46% in Controls, but not in the CPP group, consistent with a protective effect of CPP against diabetes progression in adults already expressing T2DM. Remarkably, the beneficial CPP fiber effect in preventing diabetes or its progression occurs in both young and adult rats, which in turn mimic the signs and symptoms of T2DM in humans consuming a Western diet presenting a high glycemic load.

Example 7. Effect of Plant-Supplemented Diets on Gut Microbiome in Rats

In a first set of experiments, Nile rats were fed four different diets that produced different degrees of T2DM. The diets were 73MBS (70:10:20, a high carbohydrate diet that induces metabolic syndrome), 133 (60:20:20, a high carbohydrate diabetogenic diet), 133+Lentils (500 g lentils/kg diet), and normal rat chow. See Table 3 for composition of diets. The rats were sacrificed after 8 weeks on diet, except for Diet 133, which were combined from two studies; one study was conducted with the rats fed Diet 133 for 10 weeks, and other for at least 15 weeks. Diet 73MBS was a control diabetic diet. Samples were taken from diabetic rats. Diet 73MBS+PFJ was the test diet, and Lentil samples were taken from rats fed Diet 133 supplemented with 500 g lentils/kg diet for 8 weeks. None of these rats had diabetes. Rats fed the Chow Diet were retired male breeders. They were very diabetic.

Cecum samples from the rats were analyzed by sequencing of 16S V4 rRNA genes to identify the bacterial phyla and families present. At necropsy the cecum was removed and opened and 1 cc of luminal content was scraped into a 1 cc plastic vial, sealed with a screw-cap, and frozen at −80° C. for shipment to Second Genome, Inc. for analysis. Second Genome performed nucleic acid isolation with the MoBio PowerMag® Microbiome kit (Carlsbad, CA) according to manufacturer's guidelines and optimized for high-throughput processing. All samples were quantified via the Qubit® Quant-iT dsDNA High Sensitivity Kit (Invitrogen, Life Technologies, Grand Island, NY) to ensure that they met minimum concentration and mass of DNA.

To enrich the sample for bacterial 16S V4 rDNA region, DNA was amplified utilizing fusion primers designed against the surrounding conserved regions which are tailed with sequences to incorporate Illumina (San Diego, CA) adapters and indexing barcodes. Each sample was PCR amplified with two differently bar coded V4 fusion primers. Samples that met the post-PCR quantification minimum were advanced for pooling and sequencing. For each sample, amplified products were concentrated using a solid-phase reversible immobilization method for the purification of PCR products and quantified by qPCR. A pool containing 16S V4 enriched, amplified, barcoded samples was loaded into a MiSeq® reagent cartridge, and then onto the instrument along with the flow cell. After cluster formation on the MiSeq instrument, the amplicons were sequenced for 250 cycles with custom primers designed for paired-end sequencing.

The full data analysis pipeline for Second Genome's Microbial Profiling Service incorporated several separate stages: pre-processing, summarization, normalization, alpha-diversity metrics (within sample diversity), beta diversity metrics (sample-to-sample similarity), ordination/clustering, sample classification, and significance testing. Second Genome's analysis software package was used for statistical analysis.

OTU Selection. Sequenced paired-end reads were merged using USEARCH and the resulting sequences were compared to an in-house strains database using USEARCH (usearch_global). All sequences hitting a unique strain with an identity ≥99% were assigned a strain Operation Taxonomic Unit (OTU). To ensure specificity of the strain hits, a difference of ≥0.25% between the identity of the best hit and the second best hit was required (e.g. 99.75 versus 99.5). For each strain OTU one of the matching reads was selected as representative and all sequences were mapped by USEARCH (usearch_global) against the strain OTU representatives to calculate strain abundances. The remaining non-strain sequences were quality filtered and dereplicated with USEARCH. Resulting unique sequences were then clustered at 97% by UPARSE (de novo OTU clustering) and a representative consensus sequence per de novo OTU was determined. The UPARSE clustering algorithm comprises a chimera filtering and discards likely chimeric OTUs. All non-strain sequences that passed the quality filtering were mapped to the representative consensus sequences to generate an abundance table for de novo OTUs.

Representative OTU sequences were assigned taxonomic classification via mothur's bayesian classifier, trained against the Greengenes reference database of 16S rRNA gene sequences clustered at 99%.

Summarization. After the taxa are identified for inclusion in the analysis, the values used for each taxa-sample intersection were populated with the abundance of reads assigned to each OTU in an OTU table. A corresponding table of OTU Greengenes classification was generated as well.

Alpha-diversity metrics. Observed diversity was simply the sum of unique OTUs found in each sample, also known as sample richness. Chao1 calculated the estimated sample richness (number of OTUs) based on sequencing depth and taking into account rare taxa that may be present in a sample. Shannon diversity utilized the richness of a sample along with the relative abundance of the present OTUs to calculate a diversity index.

Beta-diversity metrics. All profiles were inter-compared in a pair-wise fashion to determine a dissimilarity score and store it in a distance dissimilarity matrix. Distance functions produce low dissimilarity scores when comparing similar samples. Abundance-weighted sample pair-wise differences were calculated using the Bray-Curtis dissimilarity. Bray Curtis dissimilarity is calculated by the ratio of the summed absolute differences in counts to the sum of abundances in the two samples (Bray and Curtis 1957). The binary dissimilarity values were calculated with the Jaccard index. This metric compares the number of mismatches (OTUs present in one but absent in the other) in two samples relative to the number of OTUs present in at least one of the samples (Jaccard 1912).

Ordination, Clustering, and Classification Methods. Two-dimensional ordinations and hierarchical clustering maps of the samples in the form of dendrograms were created to graphically summarize the inter-sample relationships. Principal Coordinate Analysis (PCoA) is a method of two-dimensional ordination plotting that is used to help visualize complex relationships between samples. PCoA uses the sample-to-sample dissimilarity values to position the points relative to each other by maximizing the linear correlation between the dissimilarity values and the plot distances. To create dendrograms, the samples from the distance matrix were clustered hierarchically using the Ward method.

The results are shown in FIGS. 1A-1B, 2A-2B, 3A-3B, and 4A-4B.

The results showed that the gut microbiomes of rats fed two semi-purified diabetes-inducing diets, Diets 73MBS and 133 (extended time on diet), contained about 80% Firmicutes. See FIGS. 1A-1B (73MBS) and 2A-2B (133). On the other hand, the gut microbiomes of rats fed two plant-based diets, Diet 133+lentils (FIGS. 3A-3B) and Chow Diet (FIGS. 4A-4B), contained 45-60% Firmicutes.

In another set of experiments, the effect of dietary supplementation with various plant fiber sources on the gut microbiome was investigated. Samples from Nile rats were obtained after 10 weeks on the diets. The control diabetogenic diet was Diet 133, and the test diets (Diets 151-153) were 133 supplemented with 10% by weight of various fiber materials.

The results from the controls are shown in FIGS. 5A-5B for resistant, nondiabetic rats (133A) and in FIGS. 6A-6B for susceptible, diabetic rats (133B). The results for the fiber supplemented diets are shown for Diet 151 (10% cellulose) in FIGS. 7A-7B), for Diet 152 (10% carrot pomace) in FIGS. 8A-8B, and for Diet 153 (10% inulin) in FIGS. 9A-9B. A surprising result was the dramatic increase in Erysipelotrichaceae with the diet containing 10% by weight of carrot pomace, and to a lesser extent with the diet containing 10% by weight of inulin. Rats fed the standard Chow Diet had about 100-fold less Erysipelotrichaceae bacteria in their intestinal flora than rats fed Diet 152.

The gut microbiota data provide additional support for the finding that one of the main effects of CPP is to shift the flora profile from bad (controls) to good (CPP) in terms of the operational taxonomic units (OTUs) based on phylum and families associated with the fiber consumed. Within a fiber type or in the 0% fiber group (controls, Diets 133A and B), the flora profile was rather constant, and no major differences were observed between resistant and susceptible rats fed the same diet (fiber). This suggests that genetic differences have a major impact, while the diet can modify the severity of disease outcome when the dietary glucose burden is severe.

Figures 11A, 11B:
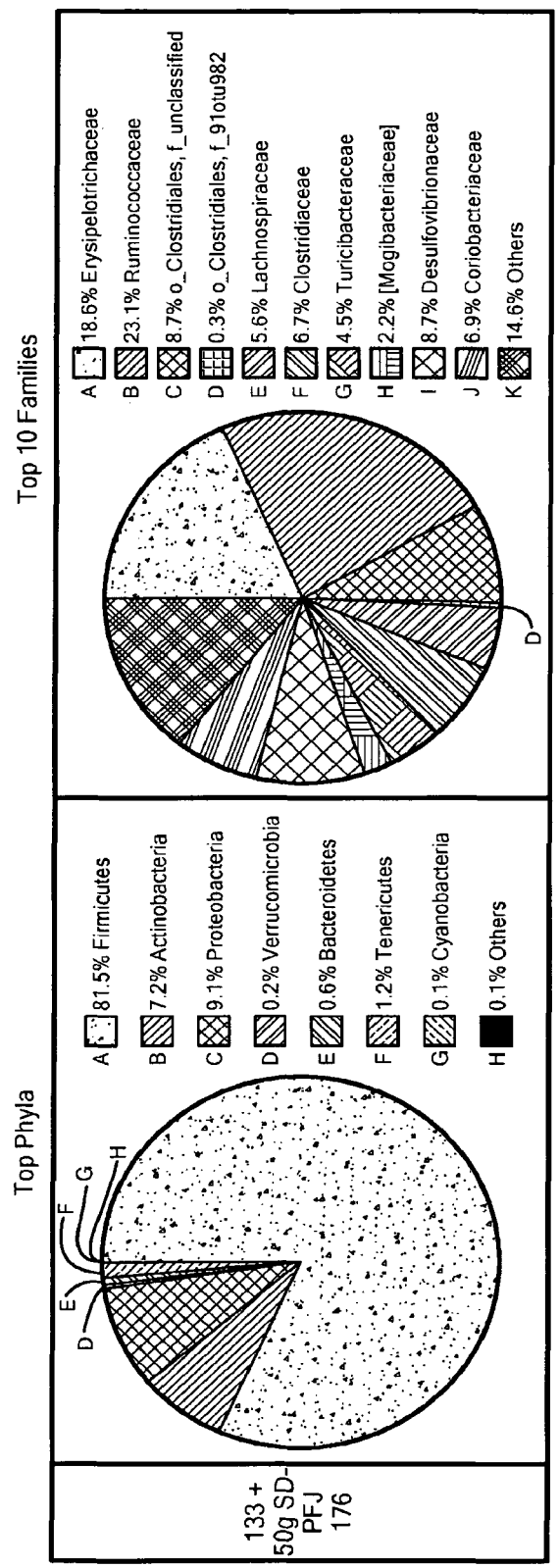
FIGS. 11A and 11B show the top phyla (FIG. 11A) and top 10 families (FIG. 11B) of bacteria found in Nile rat feces after consumption of Diet 133+50 g SD-PFJ 176.

Two additional diets were administered for 8 weeks, after which the gut microbiome was analyzed. Both were control (i.e., diabetogenic) diets supplemented with palm fruit juice (PFJ), which is a rich source of plant polyphenols. The diets were Diet 73MBS+PFJ (results shown in FIGS. 10A and 10B) and Diet 133+50 g SD-PFJ (results shown in FIGS. 11A and 11B).

Tables 13 and 14 show the development of diabetes, or resistance thereto, using different diets. For each diet, the breakdown of bacterial phyla and families from the gut microbiome analysis is shown, as well as the statistical significance of differences in microbiota among the diets.

Figure 12:
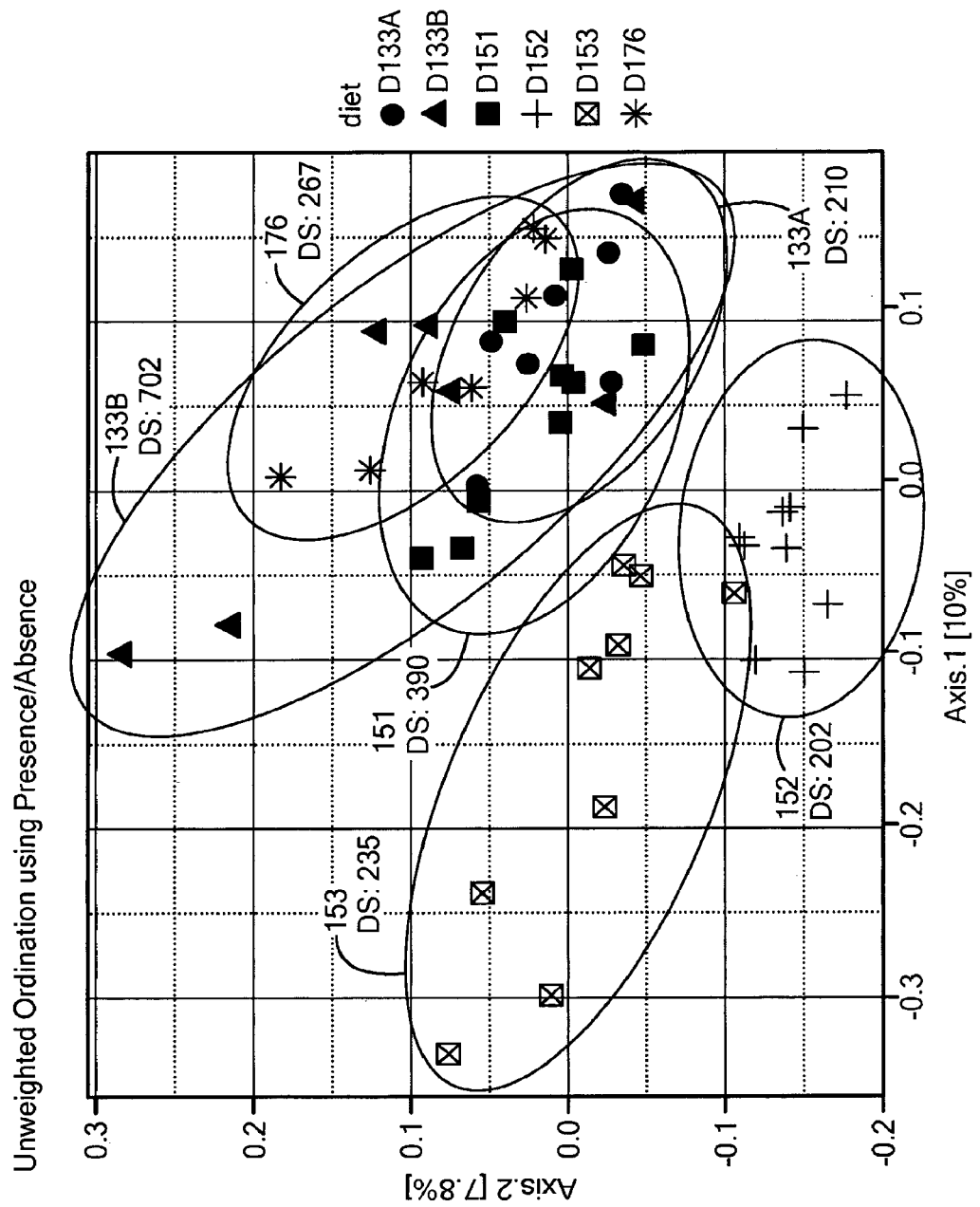
FIG. 12 shows the results of unweighted principle co-ordinate analysis of the microbiota of Nile rats fed the indicated diets.

Tables 13 and 14 show the development of diabetes, or resistance thereto, using different diets. For each diet, the breakdown of bacterial phyla and families from the gut microbiome analysis is shown, as well as the statistical significance of differences in microbiota among the diets. FIG. 12 shows the results of unweighted principle co-ordinate analysis, which shows how similar the microbiome of a sample is to other like samples based on the presence or absences of operational taxonomic units (OTUs). Similar OTU samples are clustered together in the figure, and samples from the animals fed the same diet tended to form their own clusters. Diets 133A (nondiabetic), 133B (diabetic), 176 (PFJ supplemented Diet 133), and 151 (cellulose) all clustered in the same area. By contrast, Diets 153 (10% inulin supplemented) and 152 (10% carrot pomace supplemented) formed their own distinct clusters, emphasizing the uniqueness of the latter diets on the microbiome.

TABLE 8

Diabetic in 3 wk old male Nile rats fed hiCHO diets with 0% or 10% of various fiber types for 10 wks, split by RBG <75 mg/dl> into 'resist' vs 'suscept' (NR Studies 122 + 130: pooled)

| | Diet | | | | |
|---|---|---|---|---|---|
| | 133<br>0% Fiber | | 151<br>10% cellulose<br>(insol fiber) | | 153<br>10% inulin<br>(soluble fiber) |
| CHO:Fat:Protein (% en) | 60:20:20 | | 60:20:20 | | 60:20:20 |
| Kcal/g | 4.2 | | 3.8 | | 3.8 |
| | (n = 28) | | (n = 28) | | (n = 27) |
| 30'OGTT as T2DM (% incidence)** | 10/18 (64%) | | 8/20 (71%) | | 15/12 (44%) |
| RBG as T2DM (% incidence)*** | 16/12 (43%) | | 16/12 (43%) | | 19/8 (30%) |
| FBG as T2DM (% incidence)* | 22/6 (21%) | | 24/4 (14%) | | 23/4 (15%) |
| OR (95% CI, RBG)**** | 1.00 | | 1.00 (0.54, 1.83) ns | | 0.70 (0.34, 1.44) ns |
| average % incidence (3 glucose) | 43% | | 43% | | 30% |
| T2DM based on RBG < 75 mg/dl | resist | suscept | resist | suscept | resist |
| | (n = 16) | (n = 12) | (n = 16) | (n = 12) | (n = 19) |
| Body weight (g) | | | | | |
| Initial (3 wks of age) | 32 ± 4 | 30 ± 6 | 28 ± 6 | 32 ± 4 | 29 ± 7 |
| After 6 wks diet | 84 ± 8 | 83 ± 8$^a$ | 81 ± 10 | 94 ± 4$^{ab,x}$ | 77 ± 11 |
| After 10 wks diet | 96 ± 10 | 93 ± 13 | 95 ± 13 | 105 ± 6$^x$ | 91 ± 13 |
| Body weight gain per day (g/d) | 0.81 ± 0.13 | 0.80 ± 0.20$^{ab}$ | 0.85 ± 0.15 | 0.96 ± 0.12$^{a,x}$ | 0.80 ± 0.15 |
| Food intake (10 wks on diet) | | | | | |
| g/d | 8.2 ± 1.0 | 10.1 ± 2.2 | 9.5 ± 1.4 | 9.8 ± 1.0 | 8.7 ± 1.1 |
| kcal/d | 34 ± 4 | 43 ± 9$^{a,x}$ | 36 ± 5 | 37 ± 4 | 33 ± 4 |
| Food efficiency (g BW gained/1000 kcal) | 23 ± 2 | 20 ± 7$^{ab}$ | 24 ± 3 | 26 ± 3$^a$ | 24 ± 4 |
| Random blood glucose (mg/dl) | | | | | |
| After 6 wks$^x$ | 63 ± 11 | 313 ± 228$^{ab}$ | 65 ± 16 | 118 ± 89$^a$ | 59 ± 11 |
| After 10 wks$^x$ | 58 ± 9 | 393 ± 233$^{ab}$ | 61 ± 9 | 221 ± 163$^{ac}$ | 55 ± 8 |
| OGTT (BG mg/dl) After 10 wks | | | | | |
| Fasting blood glucose, 0 min | 46 ± 9 | 73 ± 57$^{a,x}$ | 44 ± 10 | 57 ± 23 | 46 ± 14 |
| 30 min$^x$ | 139 ± 48 | 364 ± 178$^{ab}$ | 153 ± 41 | 314 ± 95$^{bc}$ | 149 ± 52 |

| | Diet | | |
|---|---|---|---|
| | 153<br>10% inulin<br>(soluble fiber) | 152<br>10% carrot fiber<br>(sol + insol fiber) | |
| CHO:Fat:Protein (% en) | 60:20:20 | 60:20:20 | |
| Kcal/g | 3.8 | 3.7 | |
| | (n = 27) | (n = 28) | |
| 30'OGTT as T2DM (% incidence)** | 15/12 (44%) | 19/9 (32%) | |
| RBG as T2DM (% incidence)*** | 19/8 (30%) | 28/0 (0%) | |
| FBG as T2DM (% incidence)* | 23/4 (15%) | 28/0 (0%) | |
| OR (95% CI, RBG)**** | 0.70 (0.34, 1.44) ns | 0.00 (0.01, 0.04) p < 0.05 | |
| average % incidence (3 glucose) | 30% | 11% | |
| T2DM based on RBG < 75 mg/dl | suscept | resist | suscept |
| | (n = 8) | (n = 28) | (n = 0) |
| Body weight (g) | | | |
| Initial (3 wks of age) | 30 ± 4 | 31 ± 6 | na |
| After 6 wks diet | 83 ± 7$^b$ | 75 ± 9$^z$ | na |
| After 10 wks diet | 102 ± 13$^x$ | 86 ± 11$^y$ | na |
| Body weight gain per day (g/d) | 0.92 ± 0.21$^{b,x}$ | 0.69 ± 0.12$^y$ | na |
| Food intake (10 wks on diet) | | | |
| g/d | 8.8 ± 1.5 | 9.4 ± 1.7 | na |
| kcal/d | 33 ± 6$^a$ | 35 ± 6 | na |
| Food efficiency (g BW gained/1000 kcal) | 28 ± 6$^b$ | 20 ± 4 | na |
| Random blood glucose (mg/dl) | | | |
| After 6 wks$^x$ | 63 ± 12$^b$ | 66 ± 12 | na |
| After 10 wks$^x$ | 94 ± 29$^{ac}$ | 56 ± 7 | na |

TABLE 8-continued

Diabetic in 3 wk old male Nile rats fed hiCHO diets with 0% or 10% of various fiber types for 10 wks, split by RBG <75 mg/dl> into 'resist' vs 'suscept' (NR Studies 122 + 130: pooled)

| OGTT (BG mg/dl) After 10 wks | | | |
|---|---|---|---|
| Fasting blood glucose, 0 min | 47 ± 13$^a$ | 44 ± 8 | na |
| 30 min$^x$ | 196 ± 111$^{ac}$ | 135 ± 57 | na |

Values are mean ± SD (n = 27-28)
$^{a,b,c}$'suscept' means in a row sharing a common superscript differ (p < 0.05) by 2-way ANOVA and Fisher's PLSD.
*Incidence T2DM based on FBG <60 mg/dl> after 10 wk on diet.
**Incidence T2DM based on OGTT 30' <150 mg/dl> after 10 wk on diet.
***Incidence T2DM based on RBG <75 mg/dl> afer 10 wk on diet.
****Odds Ratio using percent incidence based on RBG after 10 wk on diet.
$^x$= suscept > resist by 2-way ANOVA, p < 0.05
$^y$= 'resist' less than other 'resist' by 2-way ANOVA, p < 0.05
$^z$= 'resist' less than 0% fiber 'resist' by 2-way ANOVA, p < 0.05

TABLE 9

Fecal weight, fecal fat, and fecal total cholesterol (TC) in 3 wk old male Nile rats fed hiCHO diet with 0% or 10% of various types of fiber for 10 wks (NR Study 130)

| | Diet | | | | | |
|---|---|---|---|---|---|---|
| | 133 | 151 | 153 | 152 | 152A | 152B |
| | | | INGREDIENT | | | |
| | 0% fiber | 10% cellulose | 10% inulin | 10% carrot fiber-60 mesh | 10% carrot fiber-120 mesh | 10% Hydrobind |
| CHO:Fat:Prot % E | 60:20:20 | 60:20:20 | 60:20:20 | 60:20:20 | 60:20:20 | 60:20:20 |
| (Fat/Prot % E ratio) | (1.0) | (1.0) | (1.0) | (1.0) | (1.0) | (1.0) |
| kcal/g | 4.2 | 3.8 | 3.8 | 3.7 | 3.7 | 3.8 |
| GL/2000 kcal | 224 | 200 | 200 | 208 | 208 | 201 |
| Fecal output | | | | | | |
| dry weight (g/day) | 0.61 ± 41$^a$ | 1.15 ± 0.38$^{abcde}$ | 0.40 ± 0.10$^b$ | 0.50 ± 0.15$^c$ | 0.63 ± 0.18$^d$ | 0.52 ± 0.26$^e$ |
| fecal fat (mg/g dry feces) | 24 ± 2 | 10 ± 2 | 20 ± 6 | 23 ± 4 | 18 ± 6 | 22 ± 0 |
| fecal fat (mg/day) | 15 ± 1 | 12 ± 2 | 8 + 2 | 12 ± 2 | 11 ± 4 | 11 ± 0 |
| total fecal fat/fat intake, % | 1.8 ± 0.2 | 1.7 ± 0.3 | 1.4 ± 0.4 | 1.8 ± 0.3 | 1.7 ± 0.5 | 1.5 ± 0.0 |
| fecal TC (mg/g dry feces) | 2.00 ± 0.94$^{abcde}$ | 0.67 ± 0.05$^a$ | 0.70 ± 0.07$^b$ | 1.01 ± 0.32$^c$ | 0.73 ± 0.13$^d$ | 0.86 ± 0.15$^e$ |
| fecal TC (mg/day) | 0.93 ± 0.19$^{abcd}$ | 0.80 ± 0.13$^{efgh}$ | 0.28 ± 0.01$^{ae}$ | 0.50 ± 0.12$^{bf}$ | 0.47 ± 0.14$^{cg}$ | 0.49 ± 0.22$^{dh}$ |
| fecal TC/TC intake, % | 18 ± 5$^{abcd}$ | 16 ± 1$^{efg}$ | 6 ± 0.4$^{ae}$ | 11 ± 3$^b$ | 9 ± 2$^{cf}$ | 8 ± 2$^{dg}$ |

Values are mean ± SD (n = 9-10; for fecal fat (n = 2) and for fecal TC (n = 3-4) of combined fecal samples)
$^{a,b,c}$Means in a row sharing a common superscript differ (p < 0.05) by by one-way ANOVA and Fisher's PLSD test

TABLE 10

Diabetes in 3 wk-old male Nile rats fed hiCHO diets with 0% or 10% fiber for 10 wks (NR Study 132, unsplit)

| | Diet | | | | |
|---|---|---|---|---|---|
| | 133 | 152D | 168 | 169 | 178 |
| | | | INGREDIENT | | |
| | 0% fiber | 10 % carrot fiber, 30 mesh | 10% Citri Fi | 10% Citrus pectin | 10% Fibersol2 |
| | CHO:Fat:Prot % E (Fat/Prot % E ratio) | | | | |
| | 60:20:20 (1.0) | 60:20:20 (1.0) | 60:20:20 (1.0) | 60:20:20 (1.0) | 60:20:20 (1.0) |
| | kcal/g | | | | |
| | 4.2 | 3.7 | 3.7 | 3.7 | 3.9 |
| | GL/2000 kcal | | | | |
| | 224 | 208 | 208 | 208 | 200 |
| | n = 15 | n = 10 | n = 10 | n = 10 | n = 10 |
| OGTT <150> T2DM (% incidence) | 0/15 (100%) | 6/4 (40%) | 4/6 (60%) | 8/2 (20%) | 3/7 (70%) |
| RBG <75> T2DM (% incidence) | 6/9 (60%) | 10/0 (0%) | 7/3 (30%) | 8/2 (20%) | 7/3 (30%) |
| FBG <60> T2DM (% incidence) | 13/2 (13%) | 9/1 (10%) | 7/3 (30%) | 8/2 (20%) | 7/3 (30%) |

TABLE 10-continued

Diabetes in 3 wk-old male Nile rats fed hiCHO diets with 0% or 10% fiber for 10 wks (NR Study 132, unsplit)

| | Diet | | | | |
|---|---|---|---|---|---|
| | 133 | 152D | 168 | 169 | 178 |
| | | | INGREDIENT | | |
| | 0% fiber | 10 % carrot fiber, 30 mesh | 10% Citri Fi | 10% Citrus pectin | 10% Fibersol2 |
| | CHO:Fat:Prot % E (Fat/Prot % E ratio) | | | | |
| | 60:20:20 (1.0) | 60:20:20 (1.0) | 60:20:20 (1.0) | 60:20:20 (1.0) | 60:20:20 (1.0) |
| | kcal/g | | | | |
| | 4.2 | 3.7 | 3.7 | 3.7 | 3.9 |
| | GL/2000 kcal | | | | |
| | 224 n = 15 | 208 n = 10 | 208 n = 10 | 208 n = 10 | 200 n = 10 |
| RR (95% CI), RBG | 1.00 | 0, $p < 0.001$ | 0.50 (0.25, 0.99) $p < 0.05$ | 0.33 (0.18, 0.62) $p < 0.05$ | 0.50 (0.25, 0.99) $p < 0.05$) |
| Average % incidence | 58% | 17% | 40% | 20% | 43% |
| Body weight (g) | | | | | |
| Initial (3 wk of age) | 31 ± 6 | 31 ± 6 | 32 ± 5 | 32 ± 4 | 32 ± 6 |
| After 6 wks | 88 ± 7$^{ab}$ | 80 ± 7$^{ac}$ | 84 ± 8$^d$ | 73 ± 5$^{bcde}$ | 85 ± 8$^e$ |
| After 10 wks | 102 ± 5$^{abc}$ | 93 ± 7$^{ad}$ | 96 ± 7$^{be}$ | 85 ± 7$^{cdef}$ | 98 ± 11$^f$ |
| Food intake | | | | | |
| g/d | 8.4 ± 0.5$^a$ | 8.9 ± 0.4$^{bc}$ | 8.8 ± 0.9$^{de}$ | 7.9 ± 0.3$^{abd}$ | 8.0 ± 0.5$^{ce}$ |
| kcal/d | 35 ± 2$^{abcd}$ | 33 ± 1$^{ae}$ | 33 ± 3$^{bf}$ | 29 ± 1$^{cef}$ | 31 ± 2$^d$ |
| Food efficiency (g BW gained/1000 kcal) | 26 ± 3$^a$ | 24 ± 3$^b$ | 25 ± 2 | 22 ± 4$^{ac}$ | 27 ± 4$^{bc}$ |
| Body weight gain per day (g/d) | 0.90 ± 0.10$^{ab}$ | 0.78 ± 0.12$^{ac}$ | 0.81 ± 0.08$^d$ | 0.65 ± 0.12$^{bcde}$ | 0.84 ± 0.15$^e$ |
| Water Intake (mL/d) | 56 ± 57 | 33 ± 12 | 55 ± 59 | 43 ± 26 | 28 ± 6 |
| Fecal weight (g/24 hr) | | | | | |
| wet | 0.40 ± 0.17$^{ab}$ | 0.54 ± 0.08$^a$ | 0.51 ± 0.18$^b$ | 0.46 ± 0.05 | 0.46 ± 0.07 |
| dry | 0.37 ± 0.15$^{ab}$ | 0.51 ± 0.08$^a$ | 0.46 ± 0.13$^b$ | 0.43 ± 0.05 | 0.44 ± 0.07 |
| % change | −6 ± 4 | −5 ± 1 | −7 ± 5 | −7 ± 4 | −4 ± 1 |
| % dry feces/food intake | 4.4 ± 1.5$^{abc}$ | 5.7 ± 0.9$^a$ | 5.1 ± 0.8 | 5.5 ± 0.6$^b$ | 5.5 ± 0.8$^c$ |
| Random blood glucose (mg/dl) | | | | | |
| After 6 wks | 115 ± 110 | 63 ± 14 | 102 ± 108 | 63 ± 12 | 65 ± 13 |
| After 10 wks | 162 ± 130$^{ab}$ | 61 ± 8$^a$ | 104 ± 124 | 60 ± 15$^b$ | 95 ± 95 |
| OGTT (BG mg/dl) | | | | | |
| After 6 wks | | | | | |
| Fasting blood glucose, 0 min | 53 ± 12 | 53 ± 15 | 48 ± 13$^a$ | 43 ± 9$^b$ | 63 ± 30$^{ab}$ |
| 30 min | 249 ± 89$^{abcd}$ | 159 ± 41$^a$ | 168 ± 75$^b$ | 139 ± 26$^c$ | 176 ± 50$^d$ |
| After 10 wks | | | | | |
| Fasting blood glucose, 0 min | 50 ± 12 | 43 ± 13 | 55 ± 20 | 47 ± 12 | 54 ± 13 |
| 30 min | 281 ± 93$^{abcd}$ | 144 ± 45$^a$ | 183 ± 78$^b$ | 132 ± 31$^c$ | 180 ± 51$^d$ |
| 60 min | 227 ± 85$^{abcd}$ | 96 ± 54$^a$ | 131 ± 91$^b$ | 88 ± 42$^c$ | 123 ± 56$^d$ |
| Organ weight (% BW) | | | | | |
| Liver | 3.76 ± 0.58$^{abcd}$ | 3.28 ± 0.24$^{ae}$ | 3.24 ± 0.34$^{bf}$ | 2.80 ± 0.23$^{cef}$ | 3.15 ± 0.45$^d$ |
| Kidney | 0.75 ± 0.13$^{abc}$ | 0.66 ± 0.04$^a$ | 0.67 ± 0.09$^b$ | 0.67 ± 0.05 | 0.66 ± 0.06$^c$ |
| Cecum | 1.24 ± 0.30$^{abcd}$ | 2.14 ± 0.36$^{aef}$ | 1.80 ± 0.34$^{beg}$ | 2.27 ± 0.39$^{cgh}$ | 1.81 ± 0.40$^{dfh}$ |
| Adipose | | | | | |
| Epididymal | 3.33 ± 0.51 | 2.92 ± 0.42 | 3.27 ± 0.65 | 3.06 ± 0.32 | 2.98 ± 0.64 |
| Peri renal | 1.83 ± 0.37$^{ab}$ | 1.17 ± 0.50$^{ac}$ | 1.49 ± 0.41 | 1.36 ± 0.47$^b$ | 1.73 ± 0.79$^c$ |
| Brown fat | 2.35 ± 0.60$^{ab}$ | 1.71 ± 0.47$^a$ | 2.05 ± 0.32 | 1.62 ± 0.33$^b$ | 2.04 ± 0.60 |
| Total fat | 6.39 ± 1.69$^{ab}$ | 4.57 ± 1.73$^a$ | 5.28 ± 1.78 | 4.74 ± 1.40$^b$ | 5.46 ± 1.43 |
| Carcass | 73 ± 2$^a$ | 74 ± 1$^b$ | 73 ± 1$^c$ | 76 ± 3$^{abcd}$ | 73 ± 2$^d$ |
| Body length (cm) | 13.7 ± 0.4$^a$ | 13.5 ± 0.3 | 13.7 ± 0.7$^b$ | 13.1 ± 0.5$^{abc}$ | 13.7 ± 0.4$^c$ |
| Cecum pH | 7.4 ± 0.2$^a$ | 7.2 ± 0.1$^{ab}$ | 7.3 ± 0.2$^c$ | 7.5 ± 0.2$^{bcd}$ | 7.3 ± 0.2$^d$ |
| Plasma | | | | | |
| TC (mg/dl) | 130 ± 23$^a$ | 112 ± 11 | 109 ± 17$^a$ | 122 ± 19 | 126 ± 34 |
| TG (mg/dl) | 90 ± 24$^{abc}$ | 62 ± 20$^{ad}$ | 72 ± 15$^b$ | 68 ± 12$^c$ | 79 ± 16$^d$ |

Values are mean ± SD (n = 10, 15)

$^{a,b,c}$Means in a row sharing a common superscript differ ($p < 0.05$) by by one-way ANOVA and Fisher's PLSD test

TABLE 11

Diabetic assessment of 3 wk old male Nile rats fed hiCHO diets with 0% or 10% of various types of fiber for 10 wks split by 10 wk random blood glucose (NR Study 132)

| INGREDIENT | 133<br>0% fiber | | 152D<br>10% carrot fiber, 30 mesh | 168<br>10% Citri Fi | |
|---|---|---|---|---|---|
| CHO:Fat:Prot % E | 60:20:20 | | 60:20:20 | 60:20:20 | |
| (Fat/Prot % E ratio) | (1.0) | | (1.0) | (1.0) | |
| kcal/g | 4.2 | | 3.7 | 3.7 | |
| GL/2000 kcal | 224 | | 208 | | |
| OGTT <150> T2DM (% incidence) | 0/15 (100%) | | 6/4 (40%) | 4/6 (60%) | |
| RBG <75> T2DM (% incidence) | 6/9 (60%) | | 10/0 (0%) | 7/3 (30%) | |
| FBG <60> T2DM (% incidence) | 13/2 (13%) | | 9/1 (10%) | 7/3 (30%) | |
| RR (95% CI), RBG | 1.00 | | 0 [p < 0.001] | 0.50 (0.25, 0.99) [p < 0.05] | |
| Average % incidence | 58% | | 17% | 40% | |
| T2DM based on RBG < 75 mg/dl | resist | suscept | resist | resist | suscept |
|  | n = 6 | n = 9 | n = 10 | n = 7 | n = 3 |
| Body weight (g) | | | | | |
| Initial (3 wk of age) | 30 ± 7 | 32 ± 5 | 31 ± 6 | 31 ± 6 | 33 ± 3 |
| After 6 wks | 85 ± 3 | 91 ± 7$^{ab}$ | 80 ± 7$^{acd}$ | 81 ± 6 | 90 ± 9$^{ce}$ |
| After 10 wks | 100 ± 6 | 104 ± 4$^{ab}$ | 93 ± 7$^{ac}$ | 94 ± 8 | 101 ± 5 |
| Food intake | | | | | |
| g/d | 8.2 ± 0.3 | 8.6 ± 0.6$^{a}$ | 8.9 ± 0.4$^{bc}$ | 8.5 ± 0.4 | 9.6 ± 1.4$^{abde}$ |
| kcal/d | 34 ± 1 | 36 ± 2$^{abc}$ | 33 ± 1$^{ade}$ | 31 ± 1 | 36 ± 5$^{dfg}$ |
| Food efficiency (g BW gained/1000 kcal) | 26 ± 4 | 26 ± 3 | 24 ± 3$^{a}$ | 25 ± 2 | 24 ± 2 |
| Body weight gain per day (g/d) | 0.88 ± 0.13 | 0.92 ± 0.09$^{a}$ | 0.78 ± 0.12$^{a}$ | 0.79 ± 0.07 | 0.86 ± 0.10 |
| Water intake (mL/d) | 33 ± 5 | 72 ± 71$^{a}$ | 33 ± 11$^{ab}$ | 36 ± 25 | 100 ± 97$^{bc}$ |
| Fecal weight (g/24 hr) | | | | | |
| wet | 0.33 ± 0.10 | 0.44 ± 0.20$^{a}$ | 0.54 ± 0.08 | 0.44 ± 0.03 | 0.65 ± 0.32$^{a}$ |
| dry | 0.32 ± 0.09 | 0.41 ± 0.17$^{ab}$ | 0.51 ± 0.08$^{a}$ | 0.42 ± 0.03 | 0.56 ± 0.22$^{b}$ |
| % change | −5 ± 1 | −6 ± 5$^{a}$ | −5 ± 1$^{b}$ | −5 ± 1 | −12 ± 8$^{ab}$ |
| % dry feces/food intake | 3.8 ± 1.0 | 4.7 ± 1.7$^{a}$ | 5.7 ± 0.9$^{a}$ | 4.9 ± 0.3 | 5.6 ± 1.5 |
| Random blood glucose (mg/dl) | | | | | |
| After 6 wks | 76 ± 9 | 141 ± 139$^{a}$ | 63 ± 14$^{ab}$ | 69 ± 10 | 178 ± 200$^{b}$ |
| After 10 wks | 65 ± 6 | 226 ± 134$^{ab}$ | 61 ± 8$^{acd}$ | 58 ± 7 | 212 ± 209 |
| OGTT (BG mg/dl) | | | | | |
| After 6 wks | | | | | |
| Fasting blood glucose, 0 min | 48 ± 12 | 56 ± 11 | 53 ± 15 | 49 ± 16 | 45 ± 1 |
| 30 min | 229 ± 86 | 263 ± 92$^{a}$ | 159 ± 41$^{a}$ | 157 ± 58 | 196 ± 118 |
| After 10 wks | | | | | |
| Fasting blood glucose, 0 min | 50 ± 6 | 50 ± 15 | 43 ± 13$^{a}$ | 51 ± 11 | 65 ± 35$^{a}$ |
| 30 min | 242 ± 50 | 307 ± 108$^{abc}$ | 144 ± 45$^{ad}$ | 163 ± 35 | 231 ± 136$^{d}$ |
| 60 min | 208 ± 40 | 240 ± 106$^{ab}$ | 96 ± 54$^{a}$ | 116 ± 65 | 165 ± 148 |
| Organ weight (% BW) | | | | | |
| Liver | 3.56 ± 0.26 | 3.89 ± 0.70$^{ab}$ | 3.28 ± 0.24$^{a}$ | 3.10 ± 0.12 | 3.56 ± 0.50$^{c}$ |
| Kidney | 0.69 ± 0.04 | 0.79 ± 0.16$^{ab}$ | 0.66 ± 0.04$^{a}$ | 0.65 ± 0.07 | 0.72 ± 0.15 |
| Cecum | 1.25 ± 0.16 | 1.23 ± 0.37$^{abcd}$ | 2.14 ± 0.36$^{a}$ | 1.78 ± 0.37 | 1.86 ± 0.30$^{b}$ |
| Adipose | | | | | |
| Epididymal | 3.46 ± 0.30 | 3.23 ± 0.62 | 2.92 ± 0.42 | 3.22 ± 0.77 | 3.40 ± 0.34 |
| Perirenal | 2.02 ± 0.33 | 1.70 ± 0.36$^{a}$ | 1.17 ± 0.50$^{ab}$ | 1.52 ± 0.40 | 1.42 ± 0.52 |
| Brown fat | 2.58 ± 0.60 | 2.20 ± 0.58$^{a}$ | 1.71 ± 0.47$^{ab}$ | 2.18 ± 0.21 | 1.74 ± 0.33 |
| Total fat | 6.92 ± 1.32 | 6.04 ± 1.90 | 4.57 ± 1.73 | 5.21 ± 2.06 | 5.44 ± 1.23 |
| Carcass | 73 ± 2 | 73 ± 2 | 74 ± 1 | 73 ± 1 | 72 ± 3 |
| Body length (cm) | 13.5 ± 0.4 | 13.8 ± 0.3 | 13.5 ± 0.3 | 13.7 ± 0.8 | 13.5 ± 0.3 |
| Cecum pH | 7.3 ± 0.2 | 7.4 ± 0.2$^{a}$ | 7.2 ± 0.1$^{a}$ | 7.3 ± 0.2 | 7.3 ± 0.1 |
| Plasma | | | | | |
| TC (mg/dl) | 118 ± 13 | 137 ± 25$^{ab}$ | 112 ± 11$^{a}$ | 107 ± 20 | 114 ± 12 |
| TG (mg/dl) | 77 ± 15 | 100 ± 25$^{a}$ | 62 ± 20$^{abc}$ | 64 ± 9 | 90 ± 7$^{b}$ |

TABLE 11-continued

Diabetic assessment of 3 wk old male Nile rats fed hiCHO diets with 0% or 10% of various types of fiber for 10 wks split by 10 wk random blood glucose (NR Study 132)

| INGREDIENT | Diet 169 10% Citrus Pectin | | Diet 178 10% Fibersol2 | |
|---|---|---|---|---|
| CHO:Fat:Prot % E | 60:20:20 | | 60:20:20 | |
| (Fat/Prot % E ratio) | (1.0) | | (1.0) | |
| kcal/g | 3.7 | | 3.9 | |
| GL/2000 kcal | | | 200 | |
| OGTT <150> T2DM (% incidence) | 8/2 (20%) | | 3/7 (70%) | |
| RBG <75> T2DM (% incidence) | 8/2 (20%) | | 7/3 (30%) | |
| FBG <60> T2DM (% incidence) | 8/2 (20%) | | 7/3 (30%) | |
| RR (95% CI), RBG | 0.33 (0.18, 0.62) [p < 0.05] | | 0.50 (0.25, 0.99) [p, 0.05] | |
| Average % incidence | 20% | | 43% | |
| T2DM based on RBG < 75 mg/dl | resist n = 8 | suscept n = 2 | resist n = 7 | suscept n = 3 |
| Body weight (g) | | | | |
| Initial (3 wk of age) | 32 ± 4 | 31 ± 6 | 31 ± 6 | 32 ± 8 |
| After 6 wks | 72 ± 3 | 79 ± 8$^{bef}$ | 83 ± 6 | 90 ± 9$^{df}$ |
| After 10 wks | 83 ± 4 | 93 ± 14$^{b}$ | 94 ± 11 | 106 ± 9$^{c}$ |
| Food intake | | | | |
| g/d | 7.9 ± 0.3 | 8.0 ± 0.5$^{cd}$ | 7.9 ± 0.5 | 8.3 ± 0.3$^{e}$ |
| kcal/d | 29 ± 1 | 30 ± 2$^{bef}$ | 31 ± 2 | 32 ± 1$^{cg}$ |
| Food efficiency (g BW gained/1000 kcal) | 21 ± 3 | 27 ± 1 | 26 ± 4 | 29 ± 2$^{a}$ |
| Body weight gain per day (g/d) | 0.61 ± 0.10 | 0.79 ± 0.07 | 0.80 ± 0.16 | 0.93 ± 0.11 |
| Water intake (mL/d) | 44 ± 30 | 42 ± 12 | 27 ± 7 | 31 ± 4$^{c}$ |
| Fecal weight (g/24 hr) | | | | |
| wet | 0.45 ± 0.04 | 0.53 ± 0.04 | 0.46 ± 0.08 | 0.46 ± 0.07 |
| dry | 0.42 ± 0.03 | 0.49 ± 0.06 | 0.44 ± 0.08 | 0.44 ± 0.07 |
| % change | −6 ± 4 | −9 ± 4 | −4 ± 2 | −5 ± 1 |
| % dry feces/food intake | 5.3 ± 0.3 | 6.1 ± 1.1 | 5.6 ± 0.8 | 5.3 ± 0.7 |
| Random blood glucose (mg/dl) | | | | |
| After 6 wks | 61 ± 10 | 72 ± 19 | 63 ± 11 | 70 ± 17 |
| After 10 wks | 54 ± 9 | 85 ± 4$^{b}$ | 58 ± 8 | 180 ± 158$^{c}$ |
| OGTT (BG mg/dl) | | | | |
| After 6 wks | | | | |
| Fasting blood glucose, 0 min | 43 ± 10 | 42 ± 11 | 59 ± 25 | 73 ± 43 |
| 30 min | 131 ± 19 | 171 ± 30 | 169 ± 57 | 190 ± 31 |
| After 10 wks | | | | |
| Fasting blood glucose, 0 min | 45 ± 11 | 58 ± 15 | 59 ± 13 | 43 ± 3 |
| 30 min | 129 ± 30 | 146 ± 42$^{b}$ | 173 ± 61 | 194 ± 16$^{c}$ |
| 60 min | 84 ± 38 | 102 ± 72$^{b}$ | 112 ± 52 | 149 ± 66 |
| Organ weight (% BW) | | | | |
| Liver | 2.82 ± 0.26 | 2.71 ± 0.04$^{bca}$ | 3.02 ± 0.41 | 3.46 ± 0.45$^{d}$ |
| Kidney | 0.68 ± 0.04 | 0.66 ± 0.09 | 0.67 ± 0.06 | 0.65 ± 0.06$^{b}$ |
| Cecum | 2.38 ± 0.34 | 1.80 ± 0.12$^{c}$ | 1.82 ± 0.46 | 1.80 ± 0.28$^{d}$ |
| Adipose | | | | |
| Epididymal | 3.06 ± 0.24 | 3.06 ± 0.72 | 3.00 ± 0.77 | 2.94 ± 0.27 |
| Perirenal | 1.26 ± 0.25 | 1.76 ± 1.07 | 1.55 ± 0.89 | 2.14 ± 0.32$^{b}$ |
| Brown fat | 1.57 ± 0.33 | 1.80 ± 0.29 | 1.88 ± 0.65 | 2.42 ± 0.23 |
| Total fat | 4.71 ± 1.58 | 4.84 ± 0.44 | 5.43 ± 1.37 | 5.54 ± 1.89 |
| Carcass | 76 ± 3 | 74 ± 0 | 74 ± 3 | 73 ± 0 |
| Body length (cm) | 13.0 ± 0.5 | 13.5 ± 0.4 | 13.5 ± 0.3 | 14.1 ± 0.5 |
| Cecum pH | 7.5 ± 0.2 | 7.4 ± 0.3 | 7.3 ± 0.2 | 7.3 ± 0.1 |
| Plasma | | | | |
| TC (mg/dl) | 128 ± 16 | 101 ± 21$^{b}$ | 126 ± 39 | 127 ± 25 |
| TG (mg/dl) | 64 ± 9 | 84 ± 6 | 74 ± 17 | 92 ± 3$^{c}$ |

Values are mean ± SD (n = 2-8)

$^{a,b,c}$Means in a row sharing a common superscript differ (p < 0.05) by by one-way ANOVA and Fisher's PLSD test

TABLE 12

SUMMARY. Diabetes in 185 weanling male Nile rats fed hiCHO diets with 0% or 10% of various types of fiber for 10 wks (NR Study 122, 130 & 132, unsplit)

| | Diet | | | | | |
|---|---|---|---|---|---|---|
| | 133 | 151 | 153 | 152 | 152D | 152A |
| | INGREDIENT | | | | | |
| | 0% fiber | 10% cellulose | 10% inulin | 10% carrot fiber, 60 mesh | 10% carrot fiber, 30 mesh | 10% carrot fiber, 120 mesh |
| CHO:Fat:Prot % E | 60:20:20 | 60:20:20 | 60:20:20 | 60:20:20 | 60:20:20 | 60:20:20 |
| (Fat/Prot % E ratio) | (1.0) | (1.0) | (1.0) | (1.0) | (1.0) | (1.0) |
| kcal/q | 4.2 | 3.8 | 3.8 | 3.7 | 3.7 | 3.7 |
| GL/2000 kcal | 224 | 200 | 200 | 208 | 208 | 208 |
| | n = 43 | n = 28 | n = 27 | n = 28 | n = 10 | n = 10 |
| OGTT <150> T2DM (% incidence) | 10/33 (77%) | 8/20 (71%) | 15/12 (44%) | 19/9 (32%) | 6/4 (40%) | 6/4 (40%) |
| RBG <75> T2DM (% incidence) | 22/21 (49%) | 16/12 (43%) | 19/8 (30%) | 28/0 (0%) | 10/0 (0%) | 8/2 (20%) |
| FBG <60> T2DM (% incidence) | 35/8 (19%) | 24/4 (14%) | 23/4 (15%) | 28/0 (0%) | 9/1 (10%) | 9/1 (10%) |
| RR (95% CI), RBG* | 1.00 | 0.88 (0.52, 1.49) | 0.61 (0.32, 1.18) | 0, p < 0.01 | 0, p < 0.01 | 0.41 (0.11, 1.46) |
| Average % incidence | 48% | 43% | 30% | 11% | 17% | 23% |
| Body weight (g) | | | | | | |
| Initial (3 wk of age) | 31 ± 5 | 30 ± 5 | 29 ± 6 | 31 ± 6 | 31 ± 6 | 31 ± 5 |
| After 6 wks | 85 ± 8 | 87 ± 10 | 79 ± 10 | 75 ± 9 | 80 ± 7 | 81 ± 6 |
| After 10 wks | 97 ± 10 | 99 ± 11 | 94 ± 14 | 86 ± 11 | 93 ± 7 | 93 ± 8 |
| Food intake | | | | | | |
| g/d | 8.8 ± 1.5 | 9.6 ± 1.2 | 8.8 ± 1.2 | 9.4 ± 1.7 | 8.9 ± 0.4 | 8.5 ± 0.8 |
| kcal/d | 37 ± 6 | 37 ± 5 | 33 ± 5 | 35 ± 6 | 33 ± 1 | 32 ± 3 |
| Food efficiency (g BW gained/1000 kcal) | 23 ± 5 | 25 ± 3 | 26 ± 5 | 21 ± 5 | 24 ± 3 | 25 ± 4 |
| Body weight gain per day (g/d) | 0.85 ± 0.15 | 0.90 ± 0.14 | 0.85 ± 0.18 | 0.70 ± 0.12 | 0.78 ± 0.12 | 0.79 ± 0.14 |
| Fecal weight (g/24 hr) | (n = 25) | (n = 10) | (n = 9) | (n = 10) | | |
| wet | 0.57 ± 0.48 | 1.33 ± 0.53 | 0.45 ± 0.12 | 0.54 ± 0.15 | 0.54 ± 0.08 | 0.73 ± 0.27 |
| dry | 0.47 ± 0.30 | 1.15 ± 0.38 | 0.40 ± 0.10 | 0.50 ± 0.15 | 0.51 ± 0.08 | 0.63 ± 0.18 |
| % change | −4 ± 14 | −12 ± 6 | −9 ± 3 | −8 ± 3 | −5 ± 1 | −12 ± 9 |
| % dry feces/food intake | | 13.5 ± 3.3 | 6.5 ± 1.7 | 5.4 ± 1.3 | 5.7 ± 0.9 | 7.4 ± 2.0 |
| Random blood glucose (mg/dl) | (n = 43) | (n = 28) | (n = 27) | (n = 28) | | |
| After 6 wks | 151 ± 169 | 88 ± 64 | 60 + 11 | 66 ± 12 | 63 ± 14 | 111 ± 143 |
| After 10 wks | 188 ± 196 | 130 ± 132 | 67 ± 24 | 56 ± 7 | 61 ± 8 | 134 ± 176 |
| OGTT (BG mg/dl) | | | | | | |
| After 6 wks | (n = 25) | (n = 10) | (n = 9) | (n = 10) | | |
| Fasting blood glucose, 0 min | 52 ± 14 | 57 ± 15 | 51 ± 18 | 49 ± 18 | 53 ± 15 | 61 ± 20 |
| 30 min | 251 ± 115 | 214 ± 116 | 150 ± 57 | 130 + 59 | 159 ± 41 | 206 ± 124 |
| After 10 wks | (n = 43) | (n = 28) | (n = 27) | (n = 28) | | |
| Fasting blood glucose, 0 min | 55 ± 33 | 50 ± 18 | 46 ± 13 | 44 ± 8 | 43 ± 13 | 44 ± 12 |
| 30 min | 251 ± 144 | 222 ± 105 | 163 ± 75 | 135 ± 57 | 144 ± 45 | 230 ± 178 |
| Organ weight (% BW) | (n = 25) | (n = 10) | (n = 9) | (n = 10) | | |
| Liver | 4.37 ± 1.17 | 3.84 ± 0.73 | 3.21 ± 0.28 | 3.18 ± 0.25 | 3.28 ± 0.24 | 3.61 ± 0.78 |
| Kidney | 0.83 ± 0.26 | 0.77 ± 0.14 | 0.64 ± 0.05 | 0.66 ± 0.09 | 0.66 ± 0.04 | 0.71 ± 0.14 |
| Cecum | 1.40 ± 0.67 | 1.27 ± 0.28 | 2.25 ± 0.55 | 2.42 ± 0.30 | 2.14 ± 0.36 | 2.40 ± 0.27 |
| Adipose | | | | | | |
| Epididymal | 2.98 ± 0.90 | 3.33 ± 0.53 | 2.83 ± 0.70 | 2.67 ± 0.46 | 2.92 ± 0.42 | 2.92 ± 0.68 |
| Perirenal | 1.46 ± 0.63 | 1.38 ± 0.47 | 1.30 ± 0.32 | 1.01 ± 0.52 | 1.17 ± 0.50 | 1.04 ± 0.47 |
| Brown fat | 1.99 ± 0.75 | 1.80 ± 0.57 | 1.94 ± 0.46 | 1.45 ± 0.45 | 1.71 ± 0.47 | 1.57 ± 0.50 |
| Total fat | 5.76 ± 1.99 | 6.52 ± 1.12 | 6.07 ± 1.33 | 5.14 ± 1.25 | 4.57 ± 1.73 | 5.52 ± 1.37 |
| Carcass | 73 ± 2 | 73 ± 2 | 74 ± 2 | 74 ± 2 | 74 ± 1 | 73 ± 1 |
| Body length (cm) | 13.7 ± 0.6 | 13.8 ± 0.5 | 13.9 ± 0.7 | 13.5 ± 0.5 | 13.5 ± 0.3 | 13.5 ± 0.7 |
| Cecum pH | 7.4 ± 0.19 | 7.2 ± 0.6 | 7.2 ± 0.0 | 7.1 ± 0.1 | 7.2 ± 0.1 | 7.2 ± 0.1 |
| | (n = 19) | (n = 4) | (n = 4) | (n = 2) | | (n = 8) |
| Plasma | (n = 25) | (n = 10) | (n = 9) | (n = 10) | | |
| TC (mg/dl) | 171 ± 128 | 127 ± 42 | 134 + 26 | 116 ± 18 | 112 ± 11 | 140 ± 45 |
| TG (mg/dl) | 107 ± 114 | 76 ± 24 | 54 ± 17 | 52 ± 21 | 62 ± 20 | 50 ± 21 |

TABLE 12-continued

SUMMARY. Diabetes in 185 weanling male Nile rats fed hiCHO diets with 0% or 10% of various types of fiber for 10 wks (NR Study 122, 130 & 132, unsplit)

| | Diet | | | |
|---|---|---|---|---|
| | 152B | 168 | 169 | 178 |
| | INGREDIENT | | | |
| | 10% hydrobind | 10% Citri Fi | 10% Citrus Pectin | 10% Fibersol-2 |
| CHO:Fat:Prot % E | 60:20:20 | 60:20:20 | 60:20:20 | 60:20:20 |
| (Fat/Prot % E ratio) | (1.0) | (1.0) | (1.0) | (1.0) |
| kcal/q | 3.8 | 3.7 | 3.7 | 3.9 |
| GL/2000 kcal | 201 | | | 200 |
| | n = 9 | n = 10 | n = 10 | n = 10 |
| OGTT <150> T2DM (% incidence) | 3/6 (67%) | 4/6 (60%) | 8/2 (20%) | 3/7 (70%) |
| RBG <75> T2DM (% incidence) | 6/3 (33%) | 7/3 (30%) | 8/2 (20%) | 7/3 (30%) |
| FBG <60> T2DM (% incidence) | 7/2 (22%) | 7/3 (30%) | 8/2 (20%) | 7/3 (30%) |
| RR (95% CI), RBG* | 0.67 (0.254, 1.78) | 0.61 (0.23, 1.66) | 0.41 (0.11, 1.46) | 0.61 (0.23, 1.66) |
| Average % incidence | 41% | 40% | 20% | 43% |
| Body weight (g) | | | | |
| Initial (3 wk of age) | 31 ± 5 | 32 ± 5 | 32 ± 4 | 32 ± 6 |
| After 6 wks | 84 ± 9 | 84 ± 8 | 73 ± 5 | 85 ± 8 |
| After 10 wks | 97 + 15 | 96 ± 7 | 85 ± 7 | 98 ± 11 |
| Food intake | | | | |
| g/d | 9.1 ± 1.8 | 8.8 ± 0.9 | 7.9 ± 0.3 | 8.0 ± 0.5 |
| kcal/d | 34 ± 7 | 33 ± 3 | 29 ± 1 | 31 ± 2 |
| Food efficiency (g BW gained/1000 kcal) | 25 ± 7 | 25 ± 2 | 22 ± 4 | 27 ± 4 |
| Body weight gain per day (g/d) | 0.84 ± 0.22 | 0.81 ± 0.08 | 0.65 ± 0.12 | 0.84 ± 0.15 |
| Fecal weight (g/24 hr) | | | | |
| wet | 0.66 ± 0.43 | 0.51 ± 0.18 | 0.46 ± 0.05 | 0.46 ± 0.07 |
| dry | 0.52 ± 0.26 | 0.46 ± 0.13 | 0.43 ± 0.05 | 0.44 ± 0.07 |
| % change | −16 ± 12 | −7 ± 5 | −7 ± 4 | −4 ± 1 |
| % dry feces/food intake | 5.6 ± 2.1 | 5.1 ± 0.8 | 5.5 ± 0.6 | 5.5 ± 0.8 |
| Random blood glucose (mg/dl) | | | | |
| After 6 wks | 159 ± 179 | 102 + 108 | 63 ± 12 | 65 ± 13 |
| After 10 wks | 181 ± 234 | 104 ± 124 | 60 ± 15 | 65 ± 14* |
| OGTT (BG mg/dl) | | | | |
| After 6 wks | | | | |
| Fasting blood glucose, 0 min | 60 ± 23 | 48 ± 13 | 43 ± 9 | 63 ± 30 |
| 30 min | 252 ± 145 | 168 ± 75 | 139 ± 26 | 176 ± 50 |
| After 10 wks | | | | |
| Fasting blood glucose, 0 min | 81 ± 71 | 55 ± 20 | 47 ± 12 | 54 ± 13 |
| 30 min | 267 ± 196 | 183 ± 78 | 132 ± 31 | 180 ± 51 |
| Organ weight (% BW) | | | | |
| Liver | 3.99 ± 1.53 | 3.24 ± 0.34 | 2.80 ± 0.23 | 3.15 ± 0.45 |
| Kidney | 0.79 ± 0.34 | 0.67 ± 0.09 | 0.67 ± 0.05 | 0.66 ± 0.06 |
| Cecum | 2.08 ± 0.91 | 1.80 ± 0.34 | 2.27 ± 0.39 | 1.81 ± 0.40 |
| Adipose | | | | |
| Epididymal | 2.76 ± 1.08 | 3.27 ± 0.65 | 3.06 ± 0.32 | 2.98 ± 0.64 |
| Perirenal | 1.54 ± 0.53 | 1.49 ± 0.41 | 1.36 ± 0.47 | 1.73 ± 0.79 |
| Brown fat | 2.00 ± 0.67 | 2.05 ± 0.32 | 1.62 ± 0.33 | 2.04 ± 0.60 |
| Total fat | 6.30 ± 1.99 | 5.28 ± 1.78 | 4.74 ± 1.40 | 5.46 ± 1.43 |
| Carcass | 71 ± 2 | 73 ± 1 | 76 ± 3 | 73 ± 2 |
| Body length (cm) | 13.5 ± 0.9 | 13.7 ± 0.7 | 13.1 ± 0.5 | 13.7 ± 0.4 |
| Cecum pH | 7.4 ± 0.2 (n = 9) | 7.3 ± 0.2 | 7.5 ± 0.2 | 7.3 ± 0.2 |
| Plasma | | | | |
| TC (mg/dl) | 156 ± 53 (n = 8) | 109 ± 17 | 122 ± 19 | 126 ± 34 |
| TG (mg/dl) | 58 ± 19 (n = 8) | 72 ± 15 | 68 ± 12 | 79 ± 16 |

Values are mean ± SD (n = 9-43)
*RR based on RBG <75>
not statisically analyzyzed as a total group (see previous tables)

TABLE 13

Microbiome assessment of male Nile Rats fed various
test diets selected for microbiome analysis (batch 1)

| | Diet: | | | | |
|---|---|---|---|---|---|
| | 73MBS | 165/164 PFJ | 133 | 161 lentils | 5008 chow |
| CHO:Fat:Prot % en | | | | | |
| | 70:10:20 | 70:10:20 | 60:20:20 | 60:20:20 | 57:17:26 |
| GL/2000 kcal | | | | | |
| | 259 | 259 | 224 | 159 | |
| kcal/g | | | | | |
| | 4.0 | 4.0 | 4.2 | 3.4 | 3.2 |
| | n = 5 | n = 7 | n = 5 | n = 5 | n = 5 |
| % incidence (RBG > 75 mg/dl) | | | | | |
| | 100% | 0% | 100% | 0% | 100% |
| Phylum | | | | | |
| Firmicutes | 85.6$^a$ | 68.9 | 75.9$^b$ | 44.6$^{a,b}$ | 57.6 |
| Actinobacteria | 2.1 | 3.3 | 1.6 | 1.0 | 3.2 |
| Proteobacteria | 6.0 | 18.5 | 10.6 | 15.9 | 6.1 |
| Verrucomicrobia | 1.9 | 0.0 | 0.4 | 1.4 | 0.3 |
| Bacteroidetes | 1.9$^{a,d}$ | 5.7$^{b,e}$ | 8.6$^c$ | 36$^{a,b,c}$ | 26.1$^{d,e}$ |
| Tenericutes | 1.9 | 1.7 | 1.6 | 0.2 | 0.9 |
| Cyanobacteria | 0.4 | 1.4 | 1.0 | 0.1 | 0.2 |
| Others | 0.3 | 0.6 | 0.3 | 0.8 | 5.5 |
| Family | | | | | |
| Erysipelotrichaceae | 14.9$^a$ | 9.5 | 16$^b$ | 1$^{a,b}$ | 0.4 |
| Ruminococcaceae | 25.5$^a$ | 20.2 | 20.1 | 7.6$^a$ | 16.2 |
| o_Clostridiales, f_unclassified | 9.3 | 4.9 | 10.4 | 4.2 | 7.1 |
| Lachnospiraceae | 6.1 | 17.5 | 5.7 | 15.6 | 4.4 |
| Clostridiaceae | 14.4$^{a,b}$ | 1.2$^a$ | 2.5 | 0.1$^b$ | 0.5 |
| o_Clostridiales, f_91otu7553 | 3.0 | 3.2 | 1.6 | 3.8 | 6.5 |
| Lactobacillaceae | 0.6$^{a,c}$ | 0.2$^{b,d}$ | 2.4 | 5$^{a,b}$ | 5.2$^{c,d}$ |
| o_Clostridiales, f_91otu10234 | 2.3 | 1.6 | 4.3 | 0.0 | 0.0 |
| Desulfovibrionaceae | 5.7 | 15$^a$ | 7.6 | 13.7 | 3.9$^a$ |
| S24-7 | 1.3$^a$ | 3.3 | 3.9 | 10.6 | 16$^a$ |
| Other | 17.0 | 23.4 | 25.6 | 38.4 | 39.9 |

Values are mean (n = 5)
$^{a,b,c}$ means with similar superscripts differ p < 0.05 by 1-way ANOVA

TABLE 14

Microbiome assessment of male Nile Rats fed various test diets selected for microbiome analysis

| | Diet: | | | | | |
|---|---|---|---|---|---|---|
| | 133A | 133B | 151 | 152 | 153 | 176 |
| | Control 0% fiber | | 10% Cellulose | 10% CPP #60 | 10% Inulin | 5% SD-PFJ |
| CHO:Fat:Prot % en | 60:20:20 | | 60:20:20 | 60:20:20 | 60:20:20 | 60:20:20 |
| GL/2000 kcal | 224 | | 200 | 208 | 200 | 224 |
| kcal/g | 4.2 | | 3.8 | 3.7 | 3.8 | 4.2 |
| | n = 7 | n = 7 | n = 9 | n = 10 | n = 9 | n = 8 |
| | RBG < 75 mg/dl | RBG > 75 mg/dl | | | | |
| % incidence (RBG > 75 mg/dl) | 50%$^a$ | | 56%$^b$ | 0%$^{a,b,c}$ | 33%$^c$ | 11% |
| Phylum | | | | | | |
| Firmicutes | 87.7 ± 8.8 | 93.5 ± 4.6 | 89.8 ± 4.0 | 82.2 ± 13.8 | 87.2 ± 8.82 | 81.5 ± 11.1 |
| Actinobacteria | 2.07 ± 1.44 | 1.93 ± 1.65$^{ab}$ | 2.90 ± 2.30 | 7.53 ± 5.13$^a$ | 4.51 ± 4.76 | 7.17 ± 3.75$^b$ |
| Proteobacteria | 4.25 ± 8.72 | 2.20 ± 3.66 | 3.19 ± 1.72 | 5.87 ± 9.87 | 1.16 ± 1.21$^a$ | 9.14 ± 9.35$^a$ |
| Verrucomicrobia | 2.64 ± 3.38 | 0.68 ± 0.97 | 2.29 ± 2.68 | 1.68 ± 3.02 | 3.27 ± 3.87 | 0.22 ± 0.60 |
| Bacteroidetes | 1.26 ± 1.04 | 0.52 ± 0.39 | 1.15 ± 1.53 | 1.34 ± 1.70 | 3.02 ± 5.01 | 0.56 ± 0.34 |
| Tenericutes | 1.77 ± 1.67 | 0.86 ± 0.46 | 0.49 ± 0.40 | 0.98 ± 0.39 | 0.46 ± 0.34 | 1.18 ± 1.23 |
| Cyanobacteria | 0.22 ± 0.20 | 0.21 ± 0.27 | 0.11 ± 0.08 | 0.28 ± 0.22 | 0.25 ± 0.24 | 0.11 ± 0.10 |
| TM7 | 0.045 ± 0.038 | 0.016 ± 0.021$^a$ | 0.052 ± 0.038 | 0.090 ± 0.053$^a$ | 0.057 ± 0.042 | 0.036 ± 0.039 |
| Others | 0.065 ± 0.062 | 0.052 ± 0.020 | 0.046 ± 0.012 | 0.052 ± 0.013 | 0.047 ± 0.12 | 0.055 ± 0.021 |

TABLE 14-continued

Microbiome assessment of male Nile Rats fed various test diets selected for microbiome analysis

| | Diet: | | | | | |
|---|---|---|---|---|---|---|
| | 133A Control 0% fiber | 133B | 151 10% Cellulose | 152 10% CPP #60 | 153 10% Inulin | 176 5% SD-PFJ |
| Family | | | | | | |
| Erysipelotrichaceae | 23.5 ± 18.2 | 20.0 ± 12.0 | 6.33 ± 6.74$^{ab}$ | 49.3 ± 19.9$^a$ | 40.9 ± 21.7$^b$ | 18.6 ± 6.5 |
| Ruminococcaceae | 23.8 ± 6.47 | 24.2 ± 8.4 | 14.0 ± 10.0 | 13.2 ± 6.2 | 11.5 ± 4.8 | 23.1 ± 11.8 |
| o_Clostridiales, f_unclassified | 7.09 ± 3.81 | 5.93 ± 4.83 | 12.8 ± 11.2 | 6.15 ± 2.60 | 10.9 ± 6.75 | 8.69 ± 4.21 |
| o_Clostridiales, f_91otu982 | 2.60 ± 4.07 | 4.68 ± 7.22 | 30.4 ± 30.0$^{ab}$ | 1.15 ± 1.53 | 0.39 ± 0.43$^a$ | 0.35 ± 0.24$^b$ |
| Lachnospiraceae | 6.21 ± 2.74 | 5.40 ± 2.27 | 8.82 ± 9.23 | 4.30 ± 2.45 | 8.66 ± 6.53 | 5.62 ± 2.49 |
| Desulfovibrionaceae | 3.93 ± 8.65 | 1.97 ± 3.61 | 2.79 ± 1.66 | 5.45 ± 9.82 | 0.88 ± 1.25$^a$ | 8.74 ± 9.14$^a$ |
| Coriobacteriaceae | 1.85 ± 1.23 | 1.34 ± 1.56$^a$ | 2.56 ± 2.18 | 6.60 ± 5.11$^a$ | 3.06 ± 4.33 | 6.87 ± 3.57 |
| Clostridiaceae | 6.14 ± 4.96$^{ab}$ | 12.4 ± 13.3$^{cde}$ | 0.41 ± 0.88$^c$ | 0.046 ± 0.042$^{adf}$ | 0.30 ± 0.67$^{beg}$ | 6.74 ± 10.1$^{fg}$ |
| Others | 24.9 ± 10.5 | 24.0 ± 7.5 | 21.9 ± 16.5 | 13.8 ± 6.5 | 23.4 ± 13.8 | 21.3 ± 9.2 |

Values are mean ± SD (n = 7-10)
$^{a,b}$Means in a row sharing common superscripts are significantly different (P < 0.05) by one-way ANOVA and Fisher's PLSD test.

TABLE 15

Relative abundance (%) for taxa of interest in relation to diet-induced diabetes in Nile rats

| | CHOW | LENTIL | Diet 133B | Diet 133A | Diet 151 | Diet 153 | Diet 152 |
|---|---|---|---|---|---|---|---|
| | | | % energy as CHO:FAT:PROT | | | | |
| | 57:17:26 | 60:20:20 | 60:20:20 | 60:20:20 | 60:20:20 | 60:20:20 | 60:20:20 |
| | | | | n= | | | |
| | 5 Chow | 5 Green Lentils | 7 hiCHO (diabetic) | 7 hiCHO (nondiabetic) | 9 hiCHO + Cellulose | 9 hiCHO + Inulin | 10 hiCHO + CPP |
| Random Blood Glucose (mg/dl) | 569 ± 65$^{abcdef}$ | 56 ± 6$^{agh}$ | 445 ± 160$^{bgijkl}$ | 57 ± 7$^{cim}$ | 220 ± 196$^{dhjmno}$ | 68 ± 13$^{ekn}$ | 54 ± 10$^{flo}$ |
| % Incidence T2DM, RBG > 75 mg/dl | 100% | 0% | 100% | 0% | 56% | 33% | 0% |
| PHYLA | | | % distribution | | | | |
| Firmicutes | 60 ± 20$^{abcde}$ | 52 ± 30$^{fghij}$ | 93 ± 5$^{af}$ | 88 ± 9$^{bg}$ | 90 ± 4$^{ch}$ | 89 ± 9$^{di}$ | 83 ± 14$^{ej}$ |
| Bacteroidetes | 24 ± 18$^{abcde}$ | 28 ± 32$^{fghij}$ | 0.5 ± 0.4$^{af}$ | 1.2 ± 1.0$^{bg}$ | 1.2 ± 1.6$^{ch}$ | 3.0 ± 5.0$^{di}$ | 1.4 ± 1.9$^{ej}$ |
| Firmicutes/Bacteroidetes ratio | 4 ± 3$^{ab}$ | 20 ± 26$^{cd}$ | 327 ± 301$^{ac}$ | 162 ± 161 | 192 ± 180 | 170 ± 180 | 235 ± 184$^{bd}$ |
| FAMILIES (phylum Firmicutes) | | | | | | | |
| Erysipelotrichaceae | 0.4 ± 0.3$^{abcd}$ | 1.4 ± 2.7$^{efgh}$ | 20 ± 12$^{aeij}$ | 24 ± 18$^{bklm}$ | 6.3 ± 6.7$^{kno}$ | 42 ± 22$^{cgiln}$ | 50 ± 20$^{dhjmo}$ |
| Clostridiaceae | 0.8 ± 1.4$^a$ | 0.1 ± 0.1$^b$ | 12 ± 13$^{abcdef}$ | 6 ± 5$^{cghi}$ | 0.4 ± 0.9$^{dg}$ | 0.3 ± 0.7$^{eh}$ | 0.05 ± 0.04$^{fi}$ |
| GENERA (phylum Bacteroidetes) | | | | | | | |
| *Prevotella* | 5.0 ± 5.7$^{abcde}$ | 2.4 ± 5.3 | 0.003 ± 0.003$^a$ | 0.01 ± 0.01$^b$ | 0.009 ± 0.02$^c$ | 0.07 ± 0.1$^d$ | 0.01 ± 0.009$^e$ |
| *Bacteroides* | 0.06 ± 0.05$^a$ | 11.5 ± 15.7$^{abcdef}$ | 0.05 ± 0.09$^b$ | 0.09 ± 0.1$^c$ | 0.02 ± 0.02$^d$ | 0.1 ± 0.3$^e$ | 0.02 ± 0.03$^f$ |
| *Prevotella/Bacteroides* ratio | 88.5 ± 91.5$^{abcdef}$ | 6.24 ± 10.6$^a$ | 0.3 ± 0.3$^b$ | 0.3 ± 0.4$^c$ | 1.8 ± 3.8$^d$ | 2.7 ± 5.5$^e$ | 2.5 ± 3.8$^e$ |
| *Lactobacillus* | 5.8 ± 5.6$^{abc}$ | 6.4 ± 8.5$^{def}$ | 6.4 ± 6.1$^{ghi}$ | 5.1 ± 5.4$^{jk}$ | 0.7 ± 1.6$^{adg}$ | 0.2 ± 0.5$^{behj}$ | 0.1 ± 0.1$^{cfik}$ |

$^{a,b}$Means in a row sharing common superscripts are significantly different (P < 0.05) by one-way ANOVA and Fisher's PLSD test.

Table 15 and FIGS. 13A-13C show the relative abundance in Nile rat gut microbiomes of several bacterial families and genera of interest for their potential influence on glucose metabolism in humans. In Table 15, which is divided into plant-based Chow and Lentils versus the 4 semipurified hiCHO diets. First, it needs to be understood that that the two plant-based diets are much less diabetic (lentils) and somewhat less (Chow) diabetogenic than the specially constituted semi-purified diet. The latter was constructed for the specific purpose of amplifying the diabetes induction in this susceptible mode, the Nile rat, so test substances could be compared for their antidiabetic properties. Thus the low abundance of Firmictues and relative increase in Bacteridetes phyla and their low F/B ratio, and the low Erysipoleltrich, and high abundance of *Prevotella* in these plant-based diets relative to the semi-puified diet is to be expected in the model. By contrast, what is even more impressive when reviewing the seriously diabetogenic semipurified diets is the evidence that addition of CPP or inulin to that high CHO diet causes several important changes, including: the aforementioned increase in Erysipelotrichaseae, a decrease in Clostridiacae, and decrease in *Lactobacillus*, the latter two having a favorable connotation based on the literature for humans with diabetes.

Furthermore, while not intending to limit the invention to any particular mechanism, it appears that at least one mechanism by which certain dietary plant fibers promote healthy glucose levels and the avoidance of diabetes and related conditions is by promoting the growth of *Prevotella* bacteria within the intestinal microflora, with subsequent beneficial effects on glucose metabolism and/or uptake. Specifically, FIG. 13A shows the relative abundance of *Prevotella* species, FIG. 13B shows the relative abundance of *Bacteroides* species, and FIG. 13C shows the ratio of the two as a function of diet. *Prevotella* bacteria (a genera of bacteria specifically associated with protection against diabetes; Arora and Backhed, 2016) were significantly reduced in the hiCHO (diabetic) group compared to nondiabetic rats fed the hiCHO diet supplemented with CPP. The changes in abundance for *Bacteroides* species was less remarkable, but was reduced on the fiber-supplemented diets. The *Prevotella/Bacteroides* ratio was highest for Nile rats fed the 10% fermentable root fibers and having the least diabetes (CPP and inulin). Specifically, the ratio for the CPP-fed rats was significantly greater (p<0.05) than rats fed the same diet containing a polyphenol supplement (palm fruit juice).

Example 8. Effect of Dietary Carrot Fiber on Blood Sugar in Humans

T2DM is characterized by having an elevated blood glucose concentration for prolonged periods, typically several years in humans. The onset of the diabetes can be tracked by following the blood glucose concentration, typically as the fasting (FBG) or random (RBG) glucose values. However, a more sensitive and more laborious assay procedure is the oral glucose tolerance test (OGTT) that measures the blood glucose excursion postprandially after consuming a set amount of glucose (50-75 g dose), either as the glucose in solution or delivered in food as a standardized breakfast meal (Tschritter et al, 2003). It has been determined that one could modify the daily blood glucose value by choosing foods with a low glucose concentration (e.g., rich in fat and protein) or by providing glucose contained in foods that release the glucose slowly after ingestion (so-called "slow carbohydrates"). Much attention has been devoted to refining this concept, especially with the awareness that diets high in certain fibers typically fall into the class of slow carbohydrates. Exactly how that works is still being resolved, but evidence strongly supports the notion that fiber can alter the gut flora, which in turn modifies whole body energy metabolism, including blood glucose and lipids, such as triglycerides and cholesterol (Esfahani et al, 2009).

The objective of the current human study was to examine specific dietary fibers for their ability to reduce the blood glucose concentration and minimize risk of developing diabetes. The approach was to modulate the postprandial blood glucose excursion when 50 g glucose was delivered by a standard breakfast meal (i.e., by applying an OGTT). The acute OGTT results were then compared with the corresponding preclinical results in animals fed the same fiber in longer term studies of T2DM outcome in the Nile rat, an animal model of diet-induced T2DM that mimics the diabetes found in humans (JB 13).

The human study recruited participants to take part in either of two dietary regimens to determine the best method for eliciting a positive blood glucose response to dietary carrot fiber, provided as carrot pomace powder, CPP. The standard or "classical" postprandial blood glucose response curve (the oral glucose tolerance test (OGTT)), involved measuring the level of blood glucose for 2 hours following consumption of a standard glucose load of 50-75 g in water. Alternatively, that glucose load was provided by a meal of white bread along with water to provide an equivalent 50 g amount of available carbohydrate in a modified OGTT (modOGTT) (Jenkins et al, 1981). In the present study this modOGTT was utilized the morning after a quantity of dietary carrot fiber had been consumed, either once in the evening 12 hr prior to the test or six times over 72 hr before the subjects consumed the standard meal of white bread (and their blood glucose followed for 2 hours). That is, subjects were exposed to the carrot fiber either a single time (Method 1, 12 hr prior to OGTT testing) or repeatedly over 3 days (Method 2, twice daily for 72 hr), the latter to allow the large bowel flora more time to be altered by fiber consumption. Both methods employed the modOGTT with white bread, but for each individual, blood glucose testing occurred before and after exposure to fiber provided by a 60-mesh carrot pomace powder (CPP).

Nilsson et al, 2006; and Kovatcheva-Datchary et al, 2015 previously showed that human subjects consuming an evening meal with either spaghetti or white wheat bread supplemented with barley or oat fiber (to reduce the glycemic index of the food) exhibited improved (reduced) blood glucose responses. These responses were evaluated by 2 hr OGTT the next morning, immediately following consumption of the standard test white wheat bread (VWVB providing 50 g available carbohydrate). The maximum reduction Nilsson et al. report for blood glucose (area under the curve (AUC) glucose measurement) attributable to dietary fiber (measured by 2 hr OGTT) was 27% on the morning following the evening meal prepared using 67 g uncooked spaghetti supplemented with nearly 20 g barley dietary fiber.

For comparison with the previous results described above, both of the presently described Methods 1 and 2 (using the morning modOGTT test) were standardized by eating a slice of the specially baked white bread (the control white bread was baked in a Cuisinart 2-lb Bread Maker Machine—CBK-100 FR (2-lb loaf=450 g all-purpose white flour, 300 ml water, 4 g yeast, 7 g salt, 4 g sugar, and 14 g canola oil, without CPP) containing exactly 50 g available carbohydrates (approximately 100 g slice) following a 12 hr overnight fast. During the modOGTT the bread was consumed with water in 10 min without other sources of calories, immediately after the 0-time blood glucose had been assessed. Subsequent blood glucose values were obtained at 15', 30', 60', 90', and 120' after the bread was consumed. Differences in the total blood glucose response were determined by assessing the area under the glucose curve (AUC) using the 0-point baseline method (Tschritter et al, 2003). Physical activity (walking, sitting, etc.) was kept consistent during the two OGTTs for each subject.

Method 1, Carrot pomace bread, single dose CPP in males: The evening before each of two morning scheduled modOGTTs (at approximately 8 p.m. and at least 3 hr after eating a light dinner) the participant consumed one of two meals. The Control meal consisted of 8 oz water and a slice of white bread which provided 50 g available carbohydrates. By contrast, the evening Test meal was provided by white bread that contained 1.5 Tbs CPP (10 g fiber) (test bread made with CPP: 20% replacement of all-purpose flour with CPP (90 g CPP, 360 g all-purpose white flour, 360 ml water, 4 g yeast, 7 g salt, 4 g sugar, and 14 g canola oil); 1 serving=50 g available carb and contains 15.8 g CPP (10 g fiber, i.e., equivalent to 1% Tbs CPP) and the 8 oz of water also contained 1 Tbs CPP (6.5 g fiber) so the total evening meal contained approximately 16.5 g fiber. The next morning, the modOGTT was conducted with the same 50 g available carbohydrates provided by the standard white bread meal (about 270 calories) containing no CPP. The concept being tested was that CPP consumed 12 h prior to the morning modOGTT with standardized white bread might have a positive effect on glucose metabolism overnight, i.e., that the postprandial OGTT curve in the morning after consuming a single dose of CPP might be improved. This finding could support the observation that CPP exerts a beneficial metabolic effect in humans consistent with the diabetes reduction observed in the long-term experiments with the Nile rat (see related examples herein).

Figure 14A:
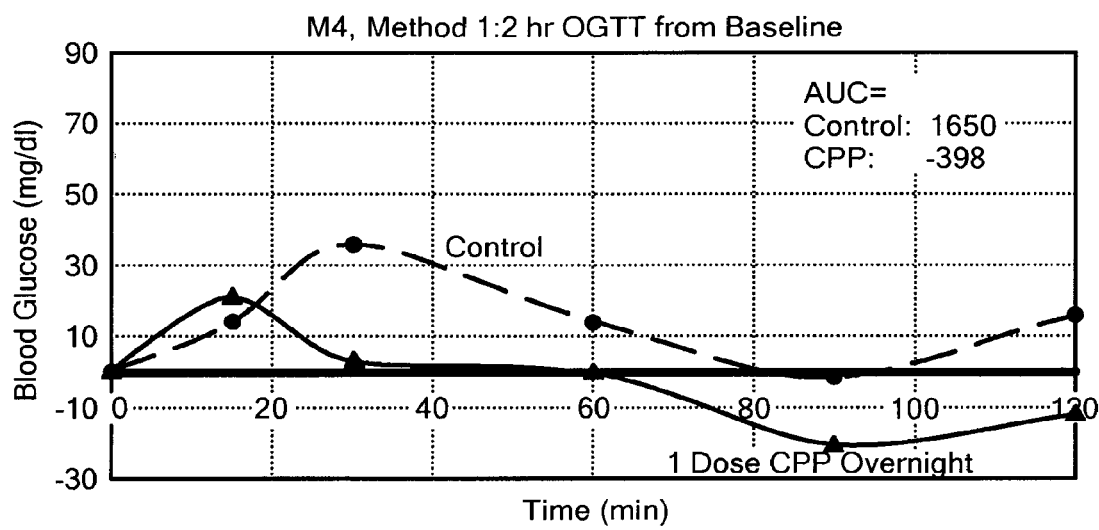
FIGS. 14A-14E show the results of oral glucose tolerance tests on human subjects as described in Example 8.
Figure 14B:
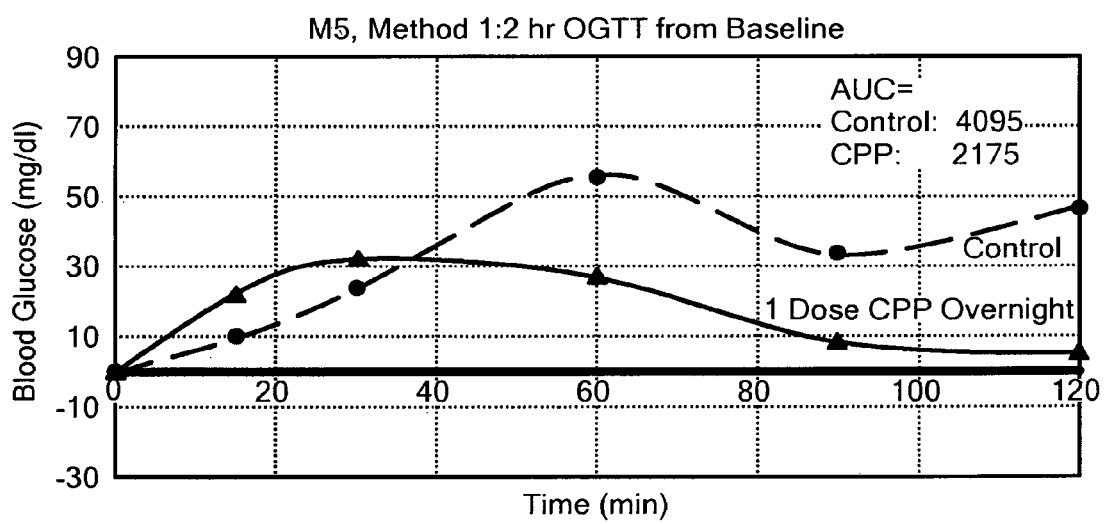

Male Results. For all subjects the data are plotted as the blood glucose excursion (in mg/dl) above or below the 0-time point (fasting baseline value established at the start of the 2 h modOGTT). Two young males M4 and M5 (20-24 yrs old) in normal health, without medications, were among the test subjects responding to Method 1. Both subjects responded favorably following exposure to CPP 12 h prior to the modOGTT based on a slice of white bread providing available carbohydrate equivalent to 50 g glucose. The results are shown in FIGS. 14A (M4) and 14B (M5). The Control profile for M4 described a preferred, normal biphasic curve (Tschritter et al, 2003) that returned to baseline at 90' before executing a slight rebound at 120'. The modOGTT curve after CPP was also weakly biphasic, but the overall blood glucose burden (AUC) was reduced by more than 100%; this result is a highly desirable postprandial response to an oral glucose load, which is associated with reduced risk of T2DM (Jenkins et al, 1981; Tschritter et al, 2003; Esfahani et al, 2009). In the case of M5, although the Control curve was biphasic, it failed to return to baseline at 90' before rising again at 120'. On the other hand, the curve following 12 h exposure to CPP was monophasic, but it did return the glucose excursion back to baseline at 90'-120', while the total AUC was reduced about 50%, again a highly desirable response.

Method 2, Carrot pomace powder for 3 days: A modOGTT using the standard white bread providing 50 g available carbohydrate was conducted on two different occasions one week apart. Both times the modOGTT was conducted without regard to the composition of the previous evening meal (subjects never having consumed CPP prior to the first/Control OGTT). However, the second modOGTT was conducted after subjects consumed CPP for 3 days (1 Tbs twice a day with meals mixed in a glass of water for a total of 2 Tbs per day providing approximately 13 g fiber/d). After the third day, each subject again fasted 12 h overnight and then consumed 50 g available carbohydrate in the standard white bread (no CPP) for breakfast to initiate the modOGTT. The hypothesis being tested was that 3 days of CPP supplementation would increase the probability of altering the gut flora sufficiently to improve the modOGTT response (Nilsson et al, 2003; Kovatcheva-Datchary et al, 2015) when compared to the shorter 12 h overnight exposure to CPP in Method 1.

Figure 14C:
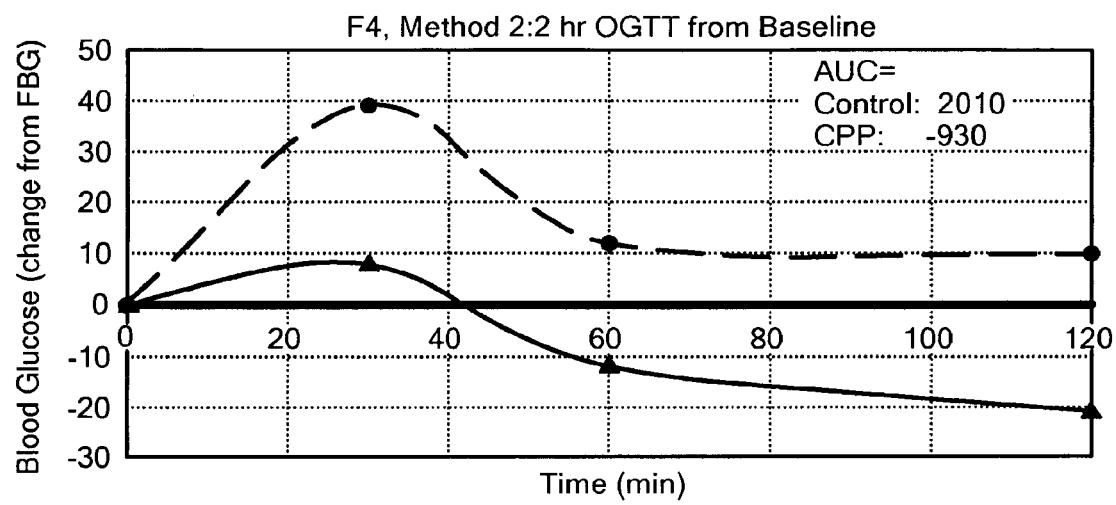
Figure 14D:
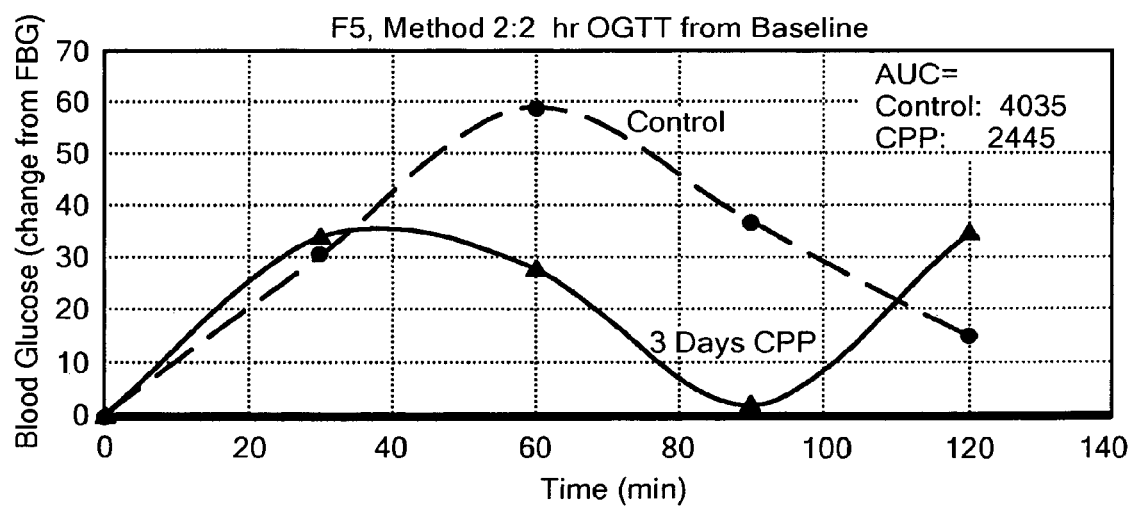

Female Results. Two women F4 and F5 (45-47 yrs old) in normal health, without medications, and having normal fasting blood glucose <90 mg/dl were among the test subjects, both providing a positive response to this approach. The results are shown in FIGS. 14C (F4) and 14D (F5). The OGTT response by F4 following the Control period revealed a monophasic glucose curve that did not fully return to baseline, but was still normal (a 30' or 60' glucose excursion greater than 75 mg/dl would suggest abnormality). However, the curve following the 3 day exposure to CPP also peaked early (30'), but essentially abolished the glucose burden provided by the 50 g of available carbohydrate in white bread, reducing the overall AUC more than 100% of that observed in the control, which is highly desirable. F5 provides a slightly different set of profiles, revealing a monophasic, otherwise normal OGTT curve during the Control test. The 3 day exposure to CPP again proved positive on two counts: the curve reverted to a more desirable biphasic response that peaked at lower threshold, and the total AUC was reduced about 50% in the process.

Figure 14E:
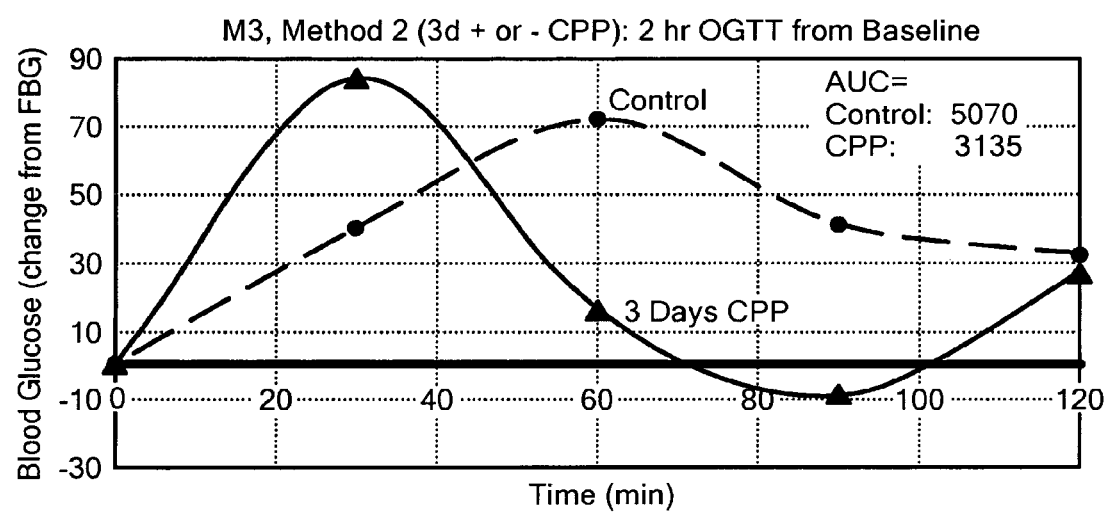

Male with prediabetes results. In another example, the testing with carrot fiber was extended to a prediabetic, otherwise healthy male (M3, 62 yr old) with an overnight FBG of 100 and 112 at baseline for Control and post-CPP supplementation periods, respectively. The results are shown in FIG. 14E. In this naïve subject the Control modOGTT revealed a monophasic curve profile that failed to return to baseline with an AUC>5000, whereas after consuming CPP for 3 days (13 g fiber/day), the AUC was reduced to 3135, and the OGTT assumed a preferred biphasic curve profile.

DISCUSSION

Both methods described above for administering dietary carrot fiber in the form of CPP were effective in modulating glucose metabolism in responsive human adult individuals of varying age and sex. In fact, the postprandial glucose response curve in these 5 adult subjects was improved on two counts in both genders. Thus, being pre-exposed to CPP tended to cause a favorable biphasic response to the modOGTT induced by a standard slice of white bread providing 50 g available carbohydrate. In addition, the resulting AUC (generated by that standard bread and resulting glucose load) was reduced substantially in all five subjects. This is noteworthy for two reasons. First, CPP supplied in modest amounts by two different approaches exerted substantial improvement in the OGTT results. Second, the results were not attributed to an altered food glycemic index of the test food, since the challenge meal used on all eight occasions for the modOGTT was the same loaf of standard white bread (lacking CPP). Thus, the effect reflected a basic shift in glucose metabolism introduced by previous exposure to the CPP, and not variation in the glycemic index of the white bread test meal that provided the altered response in all five subjects. This is a highly remarkable point because the underlying premise of the glycemic index is that the same food/meal containing the same type and amount of available CHO fed to the same individual produces a consistent blood glucose curve postprandially (Esfahani et al, 2009). The inventors have confirmed here that a dietary supplement in the form of a specific fiber can alter the host metabolic profile sufficiently to modulate the response to a standardized oral glucose load. That is, it is not just the food, but also the metabolic set point of the subject which can be a source of variation in the OGTT response.

A favorable effect of previous meals rich in barley kernel on glucose metabolism has been linked to positive changes in gut flora (Kovatcheva-Datchary et al, 2015). In the presently described human study with carrot fiber, it is surprising that a very favorable blood glucose modulating response to CPP was elicited in as little as 12 h after an overnight fast following ingestion of a single 16.5 g dose of dietary fiber ingested as CPP in bread (10 g) and water (6.5 g). Equally surprising, blood glucose control was not significantly further improved by 3 days of CPP ingested in water that provided fiber at 13 g/d.

While CPP may have longer term effects on gut microbiota and the metabolism and absorption of primary and secondary metabolites in the GI tract, it is interesting and surprising that the presence of CPP in the human GI tract appears to rather rapidly alter the microbiota profile and influence blood glucose levels. Certainly, the microbiota in Nile rat feces was substantially altered in a positive manner over a period of time by dietary CPP. Based upon the human studies herein, it would appear that CPP requires minimal time after ingestion, e.g., no more than 8-12 hours, in order to modify glucose metabolism favorably.

As used herein, "consisting essentially of" does not exclude materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

REFERENCES

1. American Diabetes Association: Standards of medical care in diabetes—2013. Diabetes Care 2013, 36(Suppl. 1): S11-S66.
2. Wang Y W, Sun G D, Sun J, Liu S J, Wang J, Xu X H, Miao L N: Spontaneous Type 2 Diabetic Rodent Models. J Diabetes Res 2013, dx.doi.org/10.1155/2013/401723.
3. Noda K, Melhorn M I, Zandi S, Frimmel S, Tayyari F, Hisatomi T, Almulki L, Pronczuk A, Hayes K C, Hafezi-Moghadam A: An animal model of spontaneous metabolic syndrome: Nile grass rat. FASEB J 2010, 24: 2443-2453.
4. Chaabo F, Pronczuk A, Maslova E, Hayes K C: Nutritional correlates and dynamics of diabetes in the Nile rat (*Arvicanthis niloticus*): a novel model for diet-induced type 2 diabetes and the metabolic syndrome. Nutr Metab 2010, 7:29.
5. Bolsinger J, Pronczuk A, Hayes K C: Dietary carbohydrate dictates development of type 2 diabetes in the Nile rat. J Nutr Biochem 2013, 24 (11): 1945-1952.
6. Bolsinger J, Pronczuk A, Sambanthamurthi R, Hayes K C: Anti-diabetic effects of palm fruit juice in the Nile rat (*Arvicanthis niloticus*). J Nutr Sci 2014, 3(e5): 1-11.
7. Lau D C W: Canada welcomes a novel class of oral glucose-lowering drugs for people with type 2 diabetes. Canadian J Diabetes 2014, 38(4): 219-220.
8. Abete I, Goyenechea E, Zulet M A, Martinez J A: Obesity and metabolic syndrome: Potential benefit from specific nutritional components. Nutr Metab Cardiovasc Dis 2011, 21(2): B1-B15.
9. Ley S H, Hamdy O, Mohan V, Hu F B: Prevention and management of type 2 diabetes: dietary components and nutritional strategies. Lancet 2014, 383: 1999-2007.
10. Bhupathiraju S N, Tobias D K, Malik V S, Pan A, Hruby A, Manson J E, Willett W C, Hu F B: Glycemic index, glycemic load, and risk of type 2 diabetes: results from 3 large U S cohorts and an updated meta-analysis. Am J Clin Nutr 2014, 100: 218-232.
11. Castro-Quezada I, Sanchez-Villegas A, Estruch R, Salas-Salvadó J, Corella D, Schröder H, Alvarez-Pérez J, Ruiz-López M D, Artacho R, Ros E, Bulló M, Covas M I, Ruiz-Gutiérrez V, Ruiz-Canela M, Buil-Cosiales P, Gómez-Gracia E, Lapetra J, Pintó X, Arós F, Fiol M, Lamuela-Raventós R M, Martínez-Gonzalez M Á, Serra-Majem L: A high dietary glycemic index increases total mortality in a Mediterranean population at high cardiovascular risk. PLoS One 2014, 9(9):e107968.
12. Bjoerck I, Granfeldt Y, Liljeberg H, Tovar J, Asp N G: Food properties affecting the digestion and absorption of carbohydrates. Am J Clin Nutr 1994, 59(Suppl.): 699S-705S.
13. Menotti A, Kromhout D, Blackburn H, Fidanza F, Buzina R, Nissinen A: Food intake patterns and 25-year mortality from coronary heart disease: Cross-cultural correlations in the Seven Countries Study. Eur J Epidemiol 1999, 15(6): 507-515.
14. Salmerón J, Ascherio A, Rimm E B, Colditz G A, Spiegelman D, Jenkins D J, Stampfer M J, Wing A L, Willett W C: Dietary fiber, glycemic load, and risk of NIDDM in men. Diabetes Care 1997, 20(4): 545-550.
15. Jones J M: CODEX-aligned dietary fiber definitions help to bridge the "fiber gap". Nutr J 2014, 13:34.
16. Sluik D, Spijkerman A M K, Tjonneland A, Tumino R, van der A D L, Weiderpass E, Orho-Melander M, Riboli E, Ricceri F, Rolandsson O, Romaguera D, Sánchez-Cantalejo E, Sluijs I, Arriola L, Barricarte A, Boeing H, Fhärm E, Franks P W, Grioni S, Johnsen N F, Kaaks R, Li K, Masala G, Mattiello A, Nilsson P M, Nöthlings U: Lifestyle factors and mortality risk in individuals with diabetes mellitus: are the associations different from those in individuals without diabetes? Diabetologia 2014, 57(1), 63-72.
17. Chou, S., Chien, P., Chau, C: Particle size reduction effectively enhances the cholesterol-lowering activities of carrot insoluble fiber and cellulose. J. Agric. Food Chem 2008, 56: 10994-98.
18. Afify, A. E. M. R., Romeilah, R. R. M., Osfor, M. M. H., Elbahnasawy, A. S. M: Evaluation of carrot pomace (*Dacucus carota* L.) as hypocholesterolemic and hypolipidemic agent on albino rats. Not Sci Biol 2013, 5(1): 7-14.
19. Kaloustian, J., Alhanout, K., Amiot-Carlin, M., Lairon, D., Portugal, H., Nicolay, A: Effect of water cooking on free phytosterol levels in beans and vegetables. Food Chem 2008, 107(4): 1379-86
20. Bahadoran Z, Mirmiran P, Azizi F: Dietary polyphenols as potential nutraceuticals in management of diabetes: a review. J Diabetes Metab Disord 2013, 12(1): 43.
21. Xiao J, Hogger P: Dietary polyphenols and type 2 diabetes: current insights and future. Curr Med Chem 2014, 22(1): 23-38.
22. Dragan S, Andrica F, Serban M C, Timar R: Polyphenols-rich natural products for treatment of diabetes. Curr Med Chem 2015, 22(1): 14-22.
23. Self Nutrition Data (nutritiondata.self.com/topics/glycemic-index).
24. Jenkins D J, Wolever T M, Taylor R H, Barker H, Fielden H, Baldwin J M,
Bowling A C, Newman H C, Jenkins A L, Goff D V: Glycemic index of foods: a physiological basis for carbohydrate exchange. Am J Clin Nutr 1981, 34(3), 362-366.
25. Willett W, Manson J, Liu S: Glycemic index, glycemic load, and risk of type 2 diabetes. Am J Clin Nutr 2002, 76(1): 274S-280S.

26. Riccardi G, Rivellese A A, Giacco R: Role of glycemic index and glycemic load in the healthy state, in prediabetes, and in diabetes. Am J Clin Nutr 2008, 87(1): 269S-274S.
27. Gellar L, Nansel T R: High and low glycemic index mixed meals and blood glucose in youth with type 2 diabetes or impaired glucose tolerance. J Pediatr 2009, 154(3): 455-458.
28. Livesey G, Taylor R, Hulshof T, Howlett J: Glycemic response and health—a systematic review and meta-analysis: relations between dietary glycemic properties and health outcomes. Am J Clin Nutr 2008, 87(suppl.), 258S-268S.
29. Feinman R D, Pogozelski W K, Astrup A, Bernstein R K, Fine E J, Westman E C, Accurso A, Frassetto L, Gower B A, McFarlane S I, Nielsen J V, Krarup T, Saslow L, Roth K S, Vernon M C, Volek J S, Wilshire G B, Dahlqvist A, Sundberg R, Childers A, Morrison K, Manninen A H, Dashti H M, Wood R J, Wortman J, Worm N: Dietary carbohydrate restriction as the first approach in diabetes management: Critical review and evidence base. Nutr J 2014, 31(1): 1-13.
30. Bao J, Atkinson F, Petocz, Willett W C, Brand-Miller J C: Prediction of postprandial glycemia and insulinemia in lean, young, healthy adults: glycemic load compared with carbohydrate content alone. Am J Clin Nutr 2011, 93: 984-996.
31. Mathew M J, Liebenberg L, Mathews E H: How do high glycemic load diets influence coronary heart disease?. Nutr. Metab. 2015, 12:6.
32. Jenkins D J, Wolever T M, Taylor R H, Barker H, Fielden H, Baldwin J M, Bowling A C, Newman H C, Jenkins A L, Goff D V. Glycemic index of foods: a physiological basis for carbohydrate exchange. Am J Clin Nutr 34(3): 362-366, 1981.
33. Esfahani A, Wong J M, Mirrahimi A, Srichaikul K, Jenkins D J, Kendall C W. The glycemic index: physiological significance. J Am Coll Nutr Suppl1:439S-445S. Review, 2009.
34. Kovatcheva-Datchary P, Nilsson A, Akrami R, Lee Y S, De Vadder F, Arora T, Hallen A, Martens E, Björckl, Bäckhed F. Dietary Fiber-Induced Improvement in Glucose Metabolism Is Associated with Increased Abundance of *Prevotella*. Cell Metab 22(6):971-82, 2015.
35. Nilsson A, Granfeldt Y, Östman E, Preston T, Bjorck I. Effects of G I and content of indigestible carbohydrates of cereal-based evening meals on glucose tolerance at a subsequent standardized breakfast. Eur J Clin Nutr 60(9): 1092-9, 2006.
36. Tschritter O, Fritsche A, Shirkavand F, Machicao F, Häring H, Stumvoll M. Assessing the shape of the glucose curve during an oral glucose tolerance test. Diabetes Care 26(4):1026-33, 2003.
37. Arora, T., Bäckhed, F. The gut microbiota and metabolic disease: current understanding and future perspectives. J Intern Med 280: 339-349, 2016

The invention claimed is:

1. A nutritional composition comprising an amount of carrot pomace, that is therapeutically effective for maintaining or improving a health-promoting intestinal microbiome in response to a diabetogenic diet in a mammalian subject in need thereof, wherein the carrot pomace comprises nondenatured soluble fiber-insoluble fiber complexes, wherein a weight ratio of soluble to insoluble fiber in the carrot pomace is from about 1:1 to about 1:3.

2. The nutritional composition of claim 1, wherein the carrot pomace comprises non-denatured pectin-cellulose type complexes.

3. The nutritional composition of claim 1, wherein the insoluble fiber is selected from the group consisting of cellulose, hemicellulose, lignin, and combinations thereof.

4. The nutritional composition of claim 1, wherein the soluble fiber comprises pectin.

5. The nutritional composition of claim 1, wherein the carrot pomace is produced from carrots by a method comprising heat treatment, juice extraction, drying, and grinding.

6. The nutritional composition of claim 5, wherein the carrot pomace is produced by a method comprising heat treatment sufficient to raise the carrot tissue to a temperature in the range from about 120° F. to about 200° F.

7. The nutritional composition of claim 5, wherein the carrot pomace is produced by a method comprising release of at least 40% of the carrot weight as juice, the juice containing at least 3.5 wt % sugar.

8. The nutritional composition of claim 5, wherein the carrot pomace is produced by a method that does not include alkaline treatment, bleach treatment, or fiber-denaturing heat treatment.

9. The nutritional composition of claim 1, wherein the nutritional composition is selected from the group consisting of foods, reduced carbohydrate foods, pet foods, beverages, reduced carbohydrate beverages, dietary supplements, nutraceuticals, dietary formulations, and reduced carbohydrate dietary formulations.

10. The nutritional composition of claim 1, wherein the subject is human.

11. The nutritional composition of claim 10, wherein the human has or is at risk of developing type 2 diabetes or obesity and/or wherein the subject has or is at risk of developing hyperlipidemia, hypercholesterolemia, and/or elevated triglycerides.

12. The nutritional composition of claim 11, wherein the human has or is at risk of developing type 2 diabetes or obesity, and wherein the nutritional composition is also suitable for use in promoting weight loss in the subject and/or also suitable for use in delaying or halting the progression or onset of diabetes in the subject.

13. The nutritional composition of claim 10, wherein the nutritional composition is also suitable for use in lowering plasma cholesterol and/or plasma triglycerides and/or also suitable for use in maintaining or achieving normal blood glucose concentration in response to a diabetogenic diet in the subject.

14. The nutritional composition of claim 1, wherein the subject is a house pet or livestock animal.

15. A nutritional composition comprising an amount of carrot pomace, that is therapeutically effective for maintaining or improving a health-promoting intestinal microbiome in response to a diabetogenic diet in a mammalian subject in need thereof, wherein the carrot pomace comprises non-denatured soluble fiber-insoluble fiber complexes, wherein the carrot pomace comprises from about 10 wt % to about 50 wt % soluble fiber.

16. The nutritional composition of claim 15, wherein the carrot pomace comprises from about 15 wt % to about 30 wt % soluble fiber.

17. The nutritional composition of claim 1, wherein the carrot pomace comprises comminuted particles from 30 to 60-mesh.

18. The nutritional composition of claim 5, wherein said grinding comprises passing the dried pomace through a grinding mill to produce comminuted particles from 30 to 60-mesh.

19. The nutritional composition of claim 5, wherein said heat treatment is sufficient to denature pectinase found in the carrot tissue.

20. The nutritional composition of claim 1, wherein the carrot pomace comprises from about 10 wt % to about 50 wt % soluble fiber.

21. The nutritional composition of claim 15, wherein a weight ratio of soluble to insoluble fiber in the carrot pomace is from about 1:1 to about 1:3.

22. The nutritional composition of claim 15, wherein the carrot pomace comprises non-denatured pectin-cellulose type complexes.

23. The nutritional composition of claim 15, wherein the insoluble fiber is selected from the group consisting of cellulose, hemicellulose, lignin, and combinations thereof.

24. The nutritional composition of claim 15, wherein the soluble fiber comprises pectin.

25. The nutritional composition of claim 15, wherein the carrot pomace is produced from carrots by a method comprising heat treatment, juice extraction, drying, and grinding.

26. The nutritional composition of claim 15, wherein the carrot pomace is produced by a method comprising heat treatment sufficient to raise the carrot tissue to a temperature in the range from about 120° F. to about 200° F.

27. The nutritional composition of claim 15, wherein the subject is human.

28. The nutritional composition of claim 27, wherein the human has or is at risk of developing type 2 diabetes or obesity and/or wherein the subject has or is at risk of developing hyperlipidemia, hypercholesterolemia, and/or elevated triglycerides.

29. The nutritional composition of claim 15, wherein the carrot pomace comprises comminuted particles from 30 to 60-mesh.

* * * * *